United States Patent
Green, II et al.

(10) Patent No.: US 6,290,644 B1
(45) Date of Patent: *Sep. 18, 2001

(54) SURGICAL INSTRUMENTS AND PROCEDURES FOR STABILIZING A LOCALIZED PORTION OF A BEATING HEART

(75) Inventors: Harry Leonard Green, II, Santa Cruz; Joshua K. Wallin, Sunnyvale; Dwight P. Morejohn, Davis; Charles S. Taylor, San Francisco; Gary B. Weller, Los Gatos; Richard M. Ferrari, Saratoga, all of CA (US)

(73) Assignee: CardioThoracic Systems, Inc., Cupertino, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/305,813

(22) Filed: May 4, 1999

Related U.S. Application Data

(63) Continuation-in-part of application No. 08/931,158, filed on Sep. 16, 1997, now Pat. No. 6,036,641, which is a continuation-in-part of application No. 08/789,751, filed on Jan. 27, 1997, which is a continuation-in-part of application No. 08/603,758, filed on Feb. 20, 1996, now Pat. No. 5,894,843.

(51) Int. Cl.$^7$ .................................................. A61B 17/02
(52) U.S. Cl. ...................... 600/235; 600/209; 600/210; 600/232
(58) Field of Search ................................... 600/201, 228, 600/232, 233, 231, 210, 209, 235, 229

(56) References Cited

U.S. PATENT DOCUMENTS

| D. 421,803 | 3/2000 | Koros et al. ................ D24/135 |
|---|---|---|
| 452,121 | 5/1891 | Haughawout . |
| 810,675 | 1/1906 | Richter . |

(List continued on next page.)

FOREIGN PATENT DOCUMENTS

| 0 283 760 A3 | 12/1988 | (DE) . |
|---|---|---|
| 0 293 760 A2 | 12/1988 | (DE) . |
| 0 293 760 B1 | 12/1988 | (DE) . |

(List continued on next page.)

OTHER PUBLICATIONS

"Long–Term Follow–up of Survivors of Postcardiotomy Circulatory Support," S.A. Ruzevich; K.R. Kantner; D.G. Pennington; M.T. Swartz; L.R. McBride; and D.T. Termuhlen *Trans. Am. Soc. Artif. Intern. Organs,* vol. XXXIV, 1988, pp. 116–124.

(List continued on next page.)

*Primary Examiner*—Paul J. Hirsch
(74) *Attorney, Agent, or Firm*—Bozicevic, Field & Francis LLP; Alan W. Cannon, Esq.

(57) ABSTRACT

In accordance with the present invention, there is disclosed surgical methods and apparatus for accessing and stabilizing the heart. The methods and apparatus facilitate access to an anastomosis site, allows various instruments or devices to be maneuvered and secured in place, and provide stabilization of the heart. The apparatus may involve a tissue stabilizer, and in particular a tissue stabilizer for use in immobilizing or stabilizing a portion of the beating heart using a compressive force delivered to the heart via the tissue stabilizer. The stabilizer may include a stabilizer base and a shaft. The shaft may be secured within an appropriate instrument mount preferably fixed to a retractor or other stable platform as disclosed herein. The stabilizers of the present invention provide improved access to a surgical site at a target vessel on the surface of the heart and may include features which facilitate optimal presentation of the target vessel.

20 Claims, 34 Drawing Sheets

U.S. PATENT DOCUMENTS

| | | | | |
|---|---|---|---|---|
| 1,706,500 | * | 3/1929 | Smith | 600/232 |
| 2,296,793 | | 9/1942 | Kirschbaum | 600/210 |
| 2,590,527 | | 9/1952 | Fluck . | |
| 2,693,795 | | 11/1954 | Grieshaber . | |
| 2,863,444 | | 12/1958 | Winsten . | |
| 3,392,722 | | 7/1968 | Jorgensen . | |
| 3,683,926 | | 8/1972 | Suzuki . | |
| 3,720,433 | | 3/1973 | Rosfelder | 294/64 |
| 3,783,373 | | 1/1974 | Jacobs . | |
| 3,858,926 | | 1/1975 | Ottenhues | 294/64 |
| 3,882,885 | | 5/1975 | Schulte et al. . | |
| 3,983,863 | | 10/1976 | Janke et al. . | |
| 4,047,532 | | 9/1977 | Phillips et al. . | |
| 4,048,987 | | 9/1977 | Hurson . | |
| 4,049,000 | | 9/1977 | Williams . | |
| 4,049,002 | | 9/1977 | Kletschka et al. . | |
| 4,052,980 | | 10/1977 | Grams . | |
| 4,226,228 | | 10/1980 | Shin et al. . | |
| 4,230,119 | | 10/1980 | Blum . | |
| 4,306,561 | | 12/1981 | de Medinaceli . | |
| 4,366,819 | | 1/1983 | Kaster . | |
| 4,368,736 | | 1/1983 | Kaster . | |
| 4,421,107 | | 12/1983 | Estes et al. . | |
| 4,428,368 | | 1/1984 | Torii . | |
| 4,434,791 | | 3/1984 | Darnell . | |
| 4,461,284 | | 7/1984 | Frackler | 128/20 |
| 4,492,229 | | 1/1985 | Grunwald . | |
| 4,637,377 | | 1/1987 | Loop . | |
| 4,646,747 | | 3/1987 | Lundback . | |
| 4,688,570 | | 8/1987 | Kramer et al. . | |
| 4,702,230 | | 10/1987 | Pelta . | |
| 4,718,418 | | 1/1988 | L'Esperance, Jr. . | |
| 4,726,356 | | 2/1988 | Santilli et al. . | |
| 4,726,358 | | 2/1988 | Brady . | |
| 4,736,749 | | 4/1988 | Lundback . | |
| 4,747,395 | | 5/1988 | Brief . | |
| 4,754,746 | | 7/1988 | Cox . | |
| 4,803,984 | | 2/1989 | Narayanan et al. . | |
| 4,808,163 | | 2/1989 | Laub | 604/105 |
| 4,829,985 | | 5/1989 | Couetil . | |
| 4,852,552 | * | 8/1989 | Chaux | 600/232 |
| 4,854,318 | | 8/1989 | Solem et al. . | |
| 4,863,133 | | 9/1989 | Bonnell | 248/278 |
| 4,865,019 | | 9/1989 | Philips . | |
| 4,884,559 | | 12/1989 | Collins . | |
| 4,925,443 | | 5/1990 | Heilman et al. . | |
| 4,949,707 | | 8/1990 | Le Vahn et al. . | |
| 4,955,896 | | 9/1990 | Freeman | 606/210 |
| 4,962,758 | | 10/1990 | Lasner et al. . | |
| 4,973,300 | | 11/1990 | Wright . | |
| 4,989,587 | | 2/1991 | Farley . | |
| 4,991,578 | | 2/1991 | Cohen . | |
| 4,993,862 | | 2/1991 | Pelta | 403/59 |
| 5,009,660 | | 4/1991 | Clapham | 606/166 |
| 5,011,469 | | 4/1991 | Buckberg et al. | 604/4 |
| 5,036,868 | | 8/1991 | Berggren et al. | 128/898 |
| 5,037,428 | | 8/1991 | Picha et al. | 606/155 |
| 5,052,373 | | 10/1991 | Michelson . | |
| 5,053,041 | | 10/1991 | Ansari et al. | 606/148 |
| 5,080,088 | | 1/1992 | LeVahn . | |
| 5,098,369 | | 3/1992 | Heilman et al. . | |
| 5,119,804 | | 6/1992 | Anstadt . | |
| 5,131,905 | | 7/1992 | Grooters . | |
| 5,133,724 | | 7/1992 | Wilson Jr., et al. | 606/151 |
| 5,159,921 | | 11/1992 | Hoover . | |
| 5,167,223 | | 12/1992 | Koros et al. . | |
| 5,171,254 | | 12/1992 | Sher | 606/166 |
| 5,231,974 | | 8/1993 | Giglio et al. . | |
| 5,287,861 | | 2/1994 | Wilk | 128/898 |
| 5,293,863 | | 3/1994 | Zhu et al. . | |
| 5,300,087 | | 4/1994 | Knoepfler | 606/207 |
| 5,318,013 | | 6/1994 | Wilk . | |
| 5,336,252 | | 8/1994 | Cohen | 607/119 |
| 5,382,756 | | 1/1995 | Dagan | 174/92 |
| 5,383,840 | | 1/1995 | Heilman et al. . | |
| 5,417,709 | | 5/1995 | Slater | 606/205 |
| 5,437,651 | | 8/1995 | Todd et al. | 604/313 |
| 5,452,733 | | 9/1995 | Sterman et al. . | |
| 5,467,763 | | 11/1995 | MCMahon et al. | 600/201 |
| 5,498,256 | | 3/1996 | Furnish | 606/1 |
| 5,503,617 | | 4/1996 | Jako | 600/201 |
| 5,509,890 | | 4/1996 | Kazama | 600/37 |
| 5,512,037 | | 4/1996 | Russell et al. | 600/206 |
| 5,514,075 | | 5/1996 | Moll et al. | 606/202 |
| 5,514,076 | | 5/1996 | Ley | 600/206 |
| 5,520,610 | | 5/1996 | Giglio et al. | 600/233 |
| 5,529,571 | | 6/1996 | Daniel | 600/219 |
| 5,547,458 | | 8/1996 | Ortiz et al. | 600/204 |
| 5,573,496 | | 11/1996 | McPherson et al. | 600/217 |
| 5,607,421 | | 3/1997 | Jeevanandam et al. | 606/15 |
| 5,607,446 | | 3/1997 | Beehler et al. | 606/198 |
| 5,613,937 | | 3/1997 | Garrison et al. | 600/201 |
| 5,651,378 | | 7/1997 | Matheny et al. | 128/898 |
| 5,727,569 | | 3/1998 | Benetti et al. | 128/898 |
| 5,730,757 | | 3/1998 | Benetti et al. | 606/198 |
| 5,749,892 | | 5/1998 | Vierra et al. | 600/204 |
| 5,755,660 | * | 5/1998 | Tyagi | 600/232 |
| 5,782,746 | | 7/1998 | Wright | 600/37 |
| 5,795,291 | | 8/1998 | Koros et al. | 600/232 |
| 5,799,661 | | 9/1998 | Boyd et al. | 128/898 |
| 5,807,243 | | 9/1998 | Vierra et al. | 600/204 |
| 5,813,410 | | 9/1998 | Levin | 128/897 |
| 5,836,311 | | 11/1998 | Borst et al. | 128/897 |
| 5,846,187 | | 12/1998 | Wells et al. | 600/201 |
| 5,846,193 | | 12/1998 | Wright | 600/215 |
| 5,846,194 | | 12/1998 | Wasson et al. | 600/228 |
| 5,865,730 | | 2/1999 | Fox et al. | 600/228 |
| 5,868,770 | | 2/1999 | Rygaard | 606/228 |
| 5,875,782 | | 3/1999 | Ferrari et al. | 128/898 |
| 5,876,332 | | 3/1999 | Looney | 600/227 |
| 5,879,291 | | 3/1999 | Kolata et al | 600/227 |
| 5,885,271 | | 3/1999 | Hamilton et al. | 606/1 |
| 5,888,247 | | 3/1999 | Benetti | 623/66 |
| 5,891,017 | | 4/1999 | Swindle et al. | 600/205 |
| 5,906,607 | | 5/1999 | Taylor et al. | 606/1 |
| 5,908,382 | | 6/1999 | Koros et al. | 600/232 |
| 5,913,876 | | 6/1999 | Taylor et al. | 607/2 |
| 5,927,284 | | 7/1999 | Borst et al. | 128/898 |
| 5,944,658 | | 8/1999 | Koros et al. | 600/232 |
| 5,944,736 | | 8/1999 | Taylor et al. | 606/198 |
| 5,947,125 | | 9/1999 | Benetti | 128/898 |
| 5,947,896 | * | 9/1999 | Shirts et al. | 600/233 |
| 5,957,835 | * | 9/1999 | Anderson et al. | 600/201 |
| 5,967,972 | | 10/1999 | Santilli et al. | 600/232 |
| 5,976,080 | * | 11/1999 | Farascioni | 600/231 |
| 5,976,171 | | 11/1999 | Taylor | 606/198 |
| 5,984,843 | | 4/1999 | Benetti et al. | 128/898 |
| 5,984,865 | | 11/1999 | Farley et al. | 600/213 |
| 5,984,867 | | 11/1999 | Deckman et al. | 600/232 |
| 6,007,486 | * | 12/1999 | Hunt et al. | 600/231 |
| 6,017,304 | | 1/2000 | Vierra et al. | 600/204 |
| 6,019,722 | | 2/2000 | Spence et al. | 600/210 |
| 6,030,340 | | 2/2000 | Maffei et al. | 600/233 |
| 6,032,672 | | 3/2000 | Taylor | 128/898 |
| 6,033,362 | * | 3/2000 | Cohn | 600/235 |
| 6,036,641 | * | 3/2000 | Taylor et al. | 600/232 |
| 6,050,266 | | 4/2000 | Benetti et al. | 128/898 |
| 6,063,021 | | 5/2000 | Hossain et al. | 600/37 |
| 6,071,295 | | 6/2000 | Takahashi | 606/191 |
| 6,099,468 | | 8/2000 | Santilli et al. | 600/232 |
| 6,102,854 | | 8/2000 | Carfier et al. | 600/228 |

| | | |
|---|---|---|
| 6,139,492 | 10/2000 | Vierra et al. ............................ 600/204 |

FOREIGN PATENT DOCUMENTS

| | | |
|---|---|---|
| 90 04513 | 6/1990 | (DE). |
| 0 630 629 | 5/1994 | (EP). |
| 668 058 A1 | 8/1995 | (EP). |
| 0 803 228 A1 | 10/1997 | (EP). |
| 0 993 806 A2 | 4/2000 | (EP). |
| 168216 | 9/1921 | (GB). |
| 2 233 561 | 1/1991 | (GB). |
| 2 267 827A | 12/1993 | (GB). |
| WO 87/04081 | 7/1987 | (WO). |
| WO 94/14383 | 7/1994 | (WO). |
| WO 94/18881 | 9/1994 | (WO). |
| WO 95/01757 | 1/1995 | (WO). |
| WO 95/15715 | 6/1995 | (WO). |
| WP 95/17127 | 6/1995 | (WO). |
| WO 96/00033 | 1/1996 | (WO). |
| WO 97/10753 | 3/1997 | (WO). |
| WO 97/32514 A2 | 9/1997 | (WO). |
| WO 97/32514 A3 | 9/1997 | (WO). |
| WO 97/40752 | 11/1997 | (WO). |
| WO 98/27869 | 7/1998 | (WO). |
| WO 98/48703 | 11/1998 | (WO). |
| WO 98/49947 | 11/1998 | (WO). |
| WO 99/08585 | 2/1999 | (WO). |
| WO 99/16367 | 4/1999 | (WO). |
| WO 00/06041 | 2/2000 | (WO). |
| WO 00/42920 | 7/2000 | (WO). |
| WO 00/42921 | 7/2000 | (WO). |
| WO 00/42935 | 7/2000 | (WO). |
| WO 00/42936 | 7/2000 | (WO). |
| WO 00/42937 | 7/2000 | (WO). |

OTHER PUBLICATIONS

Extended Clinical Support with an Implatnable Left Ventrical Assist Device,: M.G. McGee; S.M. Parnis; T. Nakatani; T. Myers; K. Dasse; W.D. Hare; J.M. Duncan; V.L. Poirier; and O.H. Frazier *Trans. Am. Soc. Artif. Intern. Organs,* vol. XXXV, 1989, pp. 614–616.

"Delayed Recovery of Severaly 'Stunned' Myocardium with the Support of a Left Ventricular Assist Device after Coronary Artery Bypass Graft Surgery," C.M. Ballantyne, MD; M.S. Verani, MD, FACC; H.D. Short, MD; C. Hyatt, BSN, RN; G.P. Noon, MD, FACC *Journal of the American College of Cardiology,* vol. 10, No. 3, Sep. 1987, pp. 710–712.

"Current Status of Cardiac Surgery: A 40–Year Review," W.E. Richenbacher, MD; J.L. Myers, MD, FACC; J.A. Waldhausen, MD, FACC *Journal of American College of Cardiology,* vol. 14, No. 3, pp. 535–544.

"Direct Myocardial Revascularization Without Extracorporeal Circulation," F.J. Benetti, MD; G. Naselli, MD; M. Wood, MD; and L. Geffner, MD *Chest,* vol. 100, No. 2, Aug., 1991, pp. 312–316.

"Reoperative Coronary Artery Bypass Grafting Without Cardiopulmonary Bypass," WJ Fanning, MD; G.S. Kakos, MD; nd T.E. Williams, Jr., MD, PhD. *The Annals of Thoracic Surgery,* vol. 55, No. 2, Feb. 1993, pp. 486–489.

"Coronary Artery Bypass Without Cardiopulmonary Bypass," A.J. Pfister, MD; M.S. Zaki, MD; J.M. Garcia, MD; L.A. Mispireta, MD; P.U. Corso, MD; A.G. Qazi, MD; S.W. Boyce, MD; T.R. Couglin, Jr., MD; and P. Gurny, MD *The Annals of Thoracic Surgery,* vol. 54, No. 6, Dec. 1992, pp. 1085–1092.

"To Use or Not To Use the Pump Oxygenator in Coronary Bypass Operations," Drs. W.G. Trapp and R. Bisarya *The Annals of Thoracic Surgery,* vol. 19, No. 1, Jan., 1975, pp. 108–109.

"Direct Myocardial Revascularization by Saphenous Vein Graft," R.G. Favaloro, MD; D.G. Effler, MD; L.K. Groves, MD; W.G. Sheldon, MD; and F. M. Sones, Jr., MD. *The Annals of Thoracic Surgery,* vol. 10, No. 2, Aug. 1970.

"Preservation of Interventricular Septal Function in Patients Having Coronary Artery Bypass Grafts Without Cardiopulmonary Bypass," C.W. Akins, MD; C.A. Boucher, MD; and G.M. Pohost, MD *American Heart Journal,* vol. 107, No. 2, Feb., 1984, pp. 304–309.

"Direct Myocardial Revascularization Without Cardiopulmonary Bypass," E. Buffolo; J.C.S. Andrade; J. Succi; L.E.V. Leao; and C. Gallucci *Thoac. Cardiovasc. Surgeon,* 33 (1985) pp. 26–29.

"Coronary Artery Revascularization Without Cardiopulmonary Bypass," R. Archer, DO; D.A. Ott, MD; R. Parravicini, MD; D.A. Cooley, MD; G.J. Reul, MD; O.H. Frazier, MD; J.M. Duncan, MD; J.J. Livesay, MD; and W.E. Walker, MD *Texas Heart Institute Journal,* vol. 11, No. 1, Mar. 1984, pp. 52–57.

"Mammary Artery–Coronary Artery Anastomosis as Method for Treatment for Angina Pectoris," V.I. Kolessov, MD *Thoracic and Cardiovascular Surgery,* vol. 54, No. 4, Oct., 1967, pp. 535–544.

"Direct Coronary Surgery with Saphenous Vein Bypass Without Either Cardiopulmonary Bypass or Cardiac Arrest," F.J. Benetti *The Journal of Cardiovascular Surgery,* vol. 26, No. 3, May–Jun., 1985, pp. 217–222.

"A Prospective Evaluation of the Pulsatile Assist Device," G.L. Zumbro, Jr., MD; G. Shearer, CCP; M.E. Fishback, M.E.; and R.F. Galloway, MD. *The Annals of Thoracic Surgery,* vol. 28, No. 2, Aug., 1979, pp. 269–273.

"Coronary Artery Operation Supported by the Hemopump: An Experimental Study on Pig," U. Lonn, MD; B. Peterzen, MD; H. Granfeldt, MD; and H. Casimir–Ahn, MD, PhD. *The Annals of Thoracic Surgery,* vol. 58, No. 1, Jul., 1994, pp. 516–523.

"Enhanced Preservation of Acutely Ischemic Myocardium with Transeptal Left Ventricular Assist," J.D. Fonger, MD; Y. Zhou, MD; H. Matsuura, MD; G.S. Aldea, MD; and R.J. Shemin, MD. *The Annals of Thoracic Surgery,* vol. 57, No. 3, Mar., 1994, pp. 570–575.

"Direct Mechanical entricular Actuation for Cardiac Arrest in Humans," M.P. Anstadt, MD; R.L. Bartlett, MD; J.P. Malone, MD, FCCP; and G.L. Anstadt, VMD. *Chest,* vol. 100, No. 1, Jul., 1991.

"Transfemoral Placement of the Left Ventricular Assist Device 'Hemopump' During Mechanical Resuscitation," K.H. Scholz; U. Tebbe; M. Chemnitius; H. Kruezer; T. Schroder; J.P. Hering; P. Uhlig; G. Hellige; H.J. Grone; R. Autschbach; B. Schorn; W. Ruschewski; and H. Dalichau *Thoracic and Cardiovascular Surgeon,* vol. 38 (1990) pp. 69–72.

"Heart–Mechanical Assist Device Interaction," J.Y. Kresh; P.L.M. Kerkhof; S.M. Goldman; and S.K. Brockman *Trans. Am. Soc. Artif. Intern. Organs,* vol. XXXII, 1986, pp. 437–443.

"Cardiogenic Shock Complicating Acute Myocardial Infarction: The Use of Coronary Angioplasty and hte Integraion of the New Support Device into Patient Management," G.M. Gacioch, MD; Stephen G. Ellism, MD, FACC; L. Lee, MD; E.R. Bates, MD, FACC; M. Kirsh, MD, FACC; J.A. Walton, MD, FACC; E.H. Topol, MD, FACC *Journal of the American College of Cardiology,* vol. 19, No. 3, Mar. 1, 1992.

"A Minimally Invasive Surgical Method for Coronary Revascularization—Preliminary Experience in Five Patients," MC Robinson, DR Gross, and W Zeman *Circulation,* (Oct. 15, 1995) vol. 92, No. 8, I–176.

"Regional Cardiac Wall Immobilization for Open Chest and Closed Chest Coronary Artery Bypass Grafting on the Beating Heart: The 'Octopus' Method," C Borst, EWL Jansen, PF Grundemann, JWF van Dongen, HJ Mansvel Beck, H Wesenhagen, PJ Slootweg, JJ Bredee *Circulation,* (Oct. 15, 1995) vol. 92, No. 8 supplement I, I–177.

Coronary Atery Bypass Grafting Without Cardiopulmonary Bypass and Without Interruption of Native Coronary Flow Using a Novel Anastomosis Site Restraining Device ("Octopus"), C Borst, EWL Jansen, CAF Tulleken, PF Grundeman, HJM Beck, JWF van Dongen, KC Hodde, JJ Bredee *J Am Coll Cardiol* May 1996; vol. 27, No. 6, pp. 1356–64.

"A Simple Technique and Device To Provide a Bloodless Operative Field in Coronary Artery Surgery Without Cross–Clamping the Aorta," M Riahi, RJ Schlosser, and LA Tomatis *The Journal of Thoracic and Cardiovascular Surgery,* vol. 66, No. 6, Dec. 1973, pp. 974–978.

Ancalmo, N. and J. L. Ochsner: "*A Modified Sternal Retractor,*" Ann. Thorac, Surg. 21 (1976) 174.

Angelini, G. D., M. D. et al., "A SImple, Inexpensive Method of Heart During Coronary Artery Bypass Surgey, " Ann. Thora. Surg 46:46–247, Aug. 1988.

Angelini , G, D., M. D. et al. "*A Fiber–Optic Retractor for Harvesting the Internal Mammory Artery,*" Ann. Thorac. Surg, (1990; 50:314–5).

Arom, K.V., et al., "Mini–Sternotomy for Coronary Artery Bupass Grafting," The Annals of Thoracic Surgery 1996; 61:1271–2.

Arom, K. V., et al., "Mini–Sternotomy for Coronary Artery Bypass Grafting," The Annals of Thoracic Surgery 1996; 62:1884–85.

Bedellino, M. M., et al., "*The Cardiac Rag –Simple Exposure of the Heart,*" Texas Heart Institute Journal, vol. 15, No. 2, 1988, 134–35.

Beg, R. A., et al., "*Internal Mammory Retractor,*" Ann Thorac, Surg., vol. 39, No. 1 pp. 286–287, Jan. 1985.

Bonatti, J., et al., "*Single Coronary Artery Bypass Grafting – A Comparison Between Minimally Invasive 'Off Pump ' Techniques and Conventional Procedures,*" European Journal of Cardio–Thoracic Surgery, 14 (Supp.I) (1998) S7–S12.

British Heart Journal, "Coronary Surgery Without Cardiopulonary Bypass," pp. 203–205, 1995.

Bugge, M., "*A New Internal Mammory Artery Retractor, *" Thorac.Cardiovasc Surgeon 38, pp.316–17 (1990).

Calafiore, A. M., et al., "*Minimally Invasive Coronary Artery Bypass Grafting,*" The Annals of Thoracic Surgery, 62:1545–8, 1996.

Campalani, G, MD., et al., "*A New Self–Retaining Internal Mammory Artery Retractor,*" J. Cardiovas. Surg. 28, 1987.

Cartier, R, MD., "*Triple Coronary Artery Revascularization on the Stablizied Beating Heart: Initial Experience,*" Montreal Heart Institute, CJS, vol. 41, No. 4, pp.283–288, Aug. 1998.

Chaux, A. and C, Blanche, "*A New Concept in Sternal Retraction: Applications for Internal Mammory Artery Dissection and Vavle Replacement Surgery,*" Ann.Thorac. Surg. 42, pp. 473–474, Oct. 1986.

Cooley, D. A., "*Limited Access Myocaradial Revascularization,*" Texas Heart Institue Journal, pp. 81–84, vol. 23, No. 2, 1996.

*Correspondence and Brief Communications,* Archives of Surgery –vol.115, 1136–37, Sep. 1980.

Cremer, J, MD, "*Off–Bypass Coronary Bypass Grafting Via Minithoracotomy Using Mechanical Epicardial Stabilization,*" The Annals of Thoracic Surgery, 63:S79–83, 1997.

Delacroix–Chevalier Surgical Instruments, IMA Savings Packages Brochure.

DelRossi, A J and Lemole, GM, "*A New Retractor to Aid in Coronary Artery Surgery,*" The Annals of Thoracic Surgeery, vol. 36, No.1, 101–102, Jul. 1983.

Green, GE., "*Technique of Internal Mammory–Coronary Artery Anastomsis,*" The Journal of Cardiovascular Surgery, 78:455–79, 1979.

Groopman, J., "*Heart Surgery, Unplugged; Making the Coronary Bypass Safer, Cheaper, and Easier,*" The New Yorker, Jan. 11, 1999, pp. 43–46, 50–51.

Robicsek, F., "Aortic Spoon–Jaw Clamp for Aorta–Saphenous Vein Anastomosis, " Journal of Cardiac Surgery, 10:583–585, 1995.

Rousou, J. et al., "Caardiac Retractor for Coronary Bypass Operations," The Society of Thoracic Surgeons, pp. 52:877–78, 1991.

Roux, D. Md. et al., "New Helper Instrument in Cardiac Surgery, " The Annals of Thoracic surgery, 48:595–6, 1989.

Stevens, et al., "*Closed Chest Artery Bypass With Cardioplegic Arrest in the Dog,*" 67th Scientific Session, 238, I–251.

Trapp, et al., "*Placement of Coronary Artery Bypass Graft without Pump Oxygenator,*" Journal of the Societey Thoracic Surgeons and the Southern Thoracic Surgeons Assn. vol. 19, No. 1, Jan. 1975.

USSC Cardiovascular Thora–Lift ™ , United States Surgical Corporation, Norwalk, Connecticut, Product Brochure.

Vigano, M., "Tecnica Operatoria, " Minerva Cardioangiologica, vol. 23–N. 6–7 (1975).

Vincent, J. G., "*A Compact Single Post Internal Mammory Artery Dissection Retractor,*" Eur. J. Cardio–Thor. Surg. 3 (1989) 276–277.

Westaby, S. et al., "Less Invasive Coronary Surgery: Coronary Surgery: Consensus From the Oxford Meeting," The Annals of Thoracic Surgery, 62:924–31, 1996.

60/117,333 Looney et al. (provisional) filed on Jan. 24,1999.

09/345,859 Looney et al. filed on Jun. 1, 1999.

09/438,670 Parsons, et al. filed on Nov. 12, 1999.

09/489,274 Brown et al. filed on Jan. 12, 2000.

Hasan, RI, et al., "*Technique of Dissecting the Internal Mammary After Using the Moussalli Bar,*" European Journal of Cardiothoracic Surgrey, 4:571–572, 1990.

Itoh, Toshiaki, M. D., et al., "*New Modification of a Mammory Artery Retractor,*" Ann. Thorac. Surg. 9, 1994; 57:1670–1.

Izzat, M. B., et al., "*Cardiac Stabilizer for Minimally Invasive Direct Coronary Artery Bypass,*" Ann. Thorqc. Surg. 1997.

Japanese Journal of Thoracic Surgrey, vol. 42, No. 2, 1989.

Japanese Article "*Heart Retractor*".

Kazama, S. et al., "*Fabric Heart Retractor for Coronary Artery Bypass Operations,*" The Annals of Thoracic Surgery, 55:1582–3, 1993.

Konishi, T. MD, et al., "Hybrid–Type Stabilizer for Off–Pump Direct Coronary Artery Bypass Grafting," Annals of Thoracic Surgery 66:961–2, 1998.

Lavergne, et al., "*Transcatheter Radiofrequency Ablation of Artrial Tissue Using a Suction Catheter,*" PACE, vol. 12, Jan. 1989, Part II, pp. 177–186.

Matsurra, A. MD, et al., "*A New Device for Exposing the Circumflex Coronary Artery,*" The Annals of Thoracic Surgery, 59:1249–50, 1995, pp. 1249–1250.

McKeown, P. P. et al., "*A Modified Sternal Retractor for Exposure of the Internal Mammary Artery,*" Ann. Thorac. Surg. 32 (1981) 619.

Ochsner, JL, et al., "*Surgical Management of Diseased Intracavitary Coronary Arteries,*" The Annals of Cardiovascular Surgery, vol. 68, No. 4, Jul. pp. 356–62, Oct. 1984.

Parsonnet, V. et al, MD, et al., "*Graduated probes for Coronary Bypass Surgery,*" The Journal of Thoracic and Cardiovascular Surgery, vol. 38, No. 3, 424–26 (Sep. 1974).

Parsonnet, V. MD, et al., "*Self–Retaining Epicardial Retractor for Aortocoronary Bypass Surgery,*" The Journa of Thoracic and Cardiovascular Surgery, 629–30 1979.

Perrault, L. et al., "Snaring of the Target Vessel in Less Invasive Bypass Operations Does Not cause Endthelial Dysfunction, " The Society of Thoracic Surgeons, pp. 751–755, 1997.

* cited by examiner

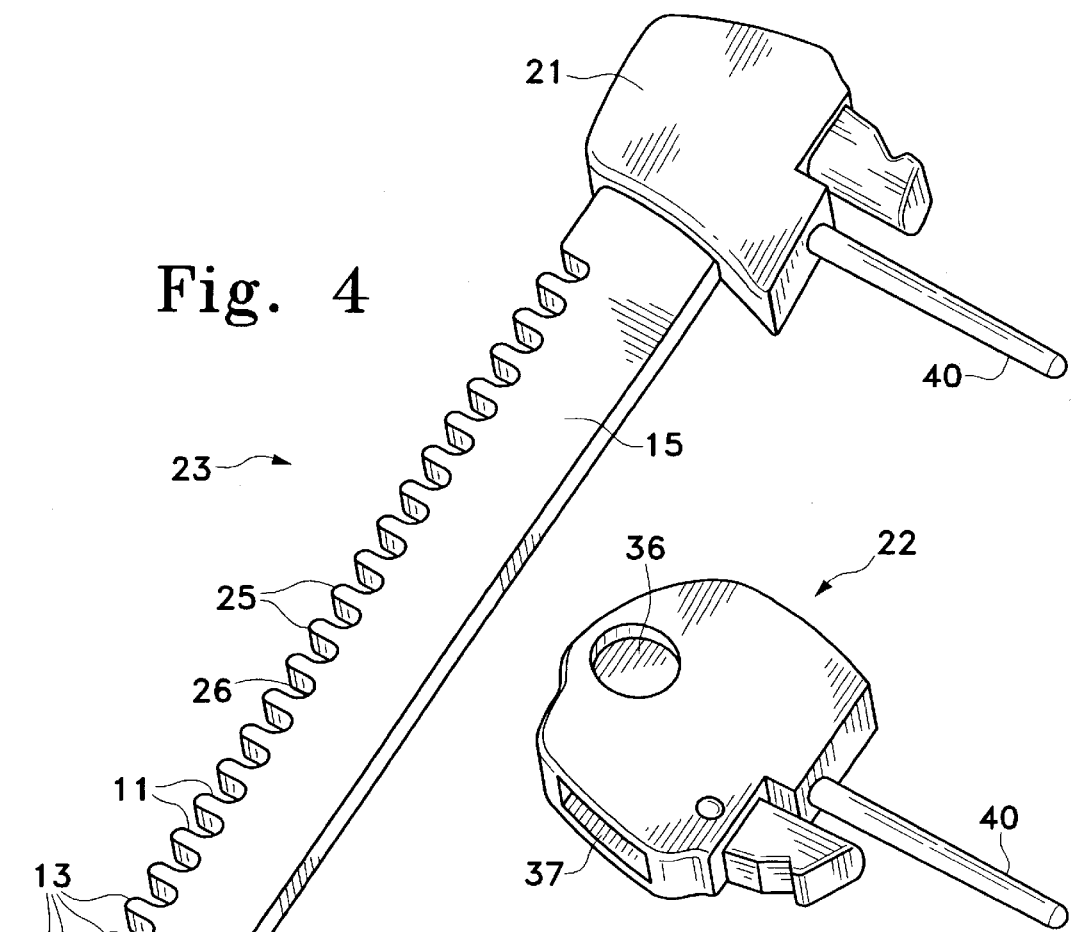
Fig. 4
Fig. 5
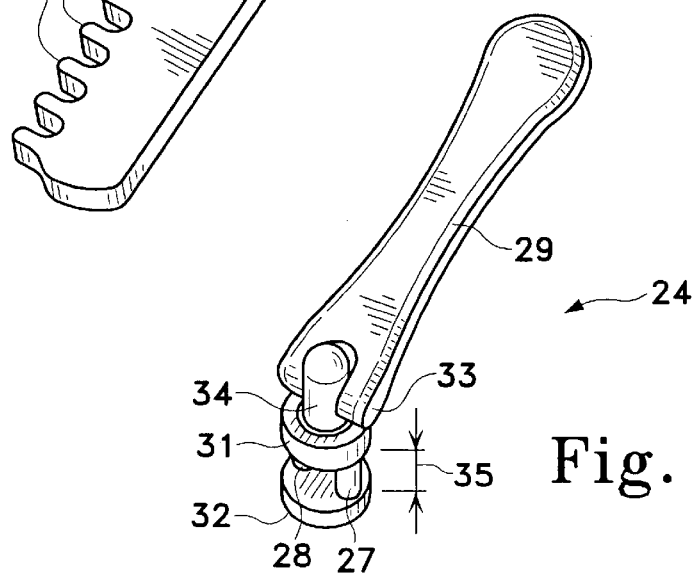
Fig. 6

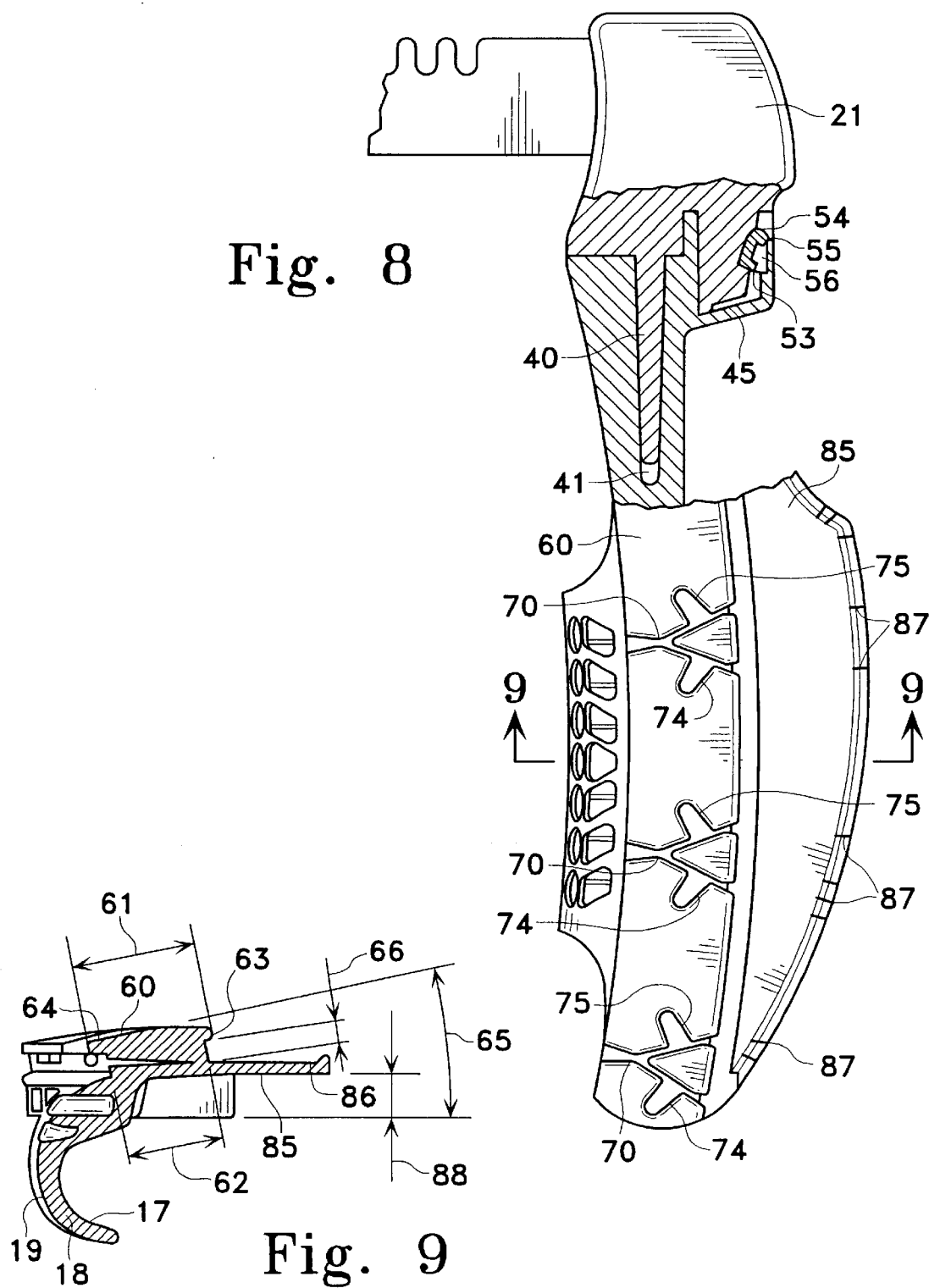

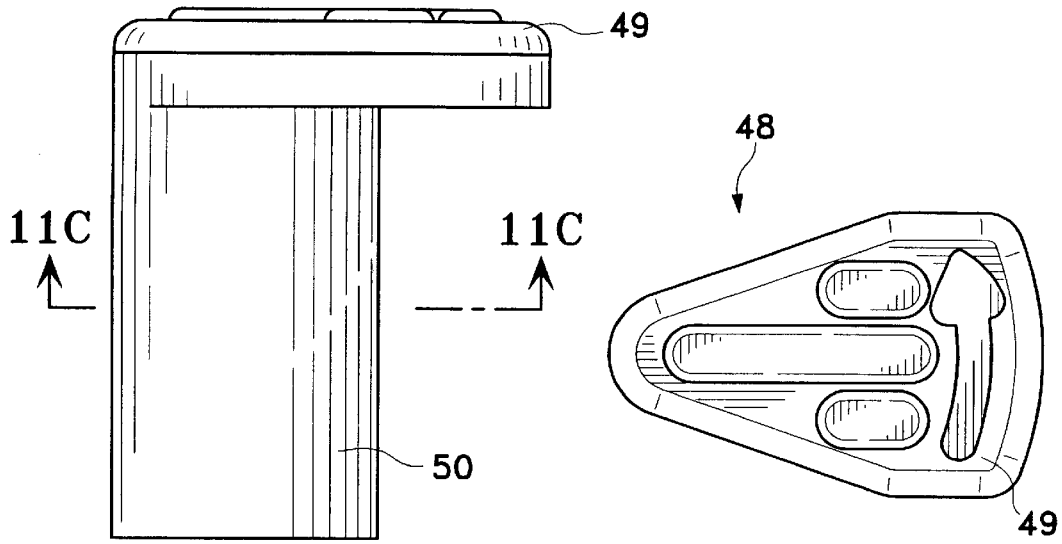
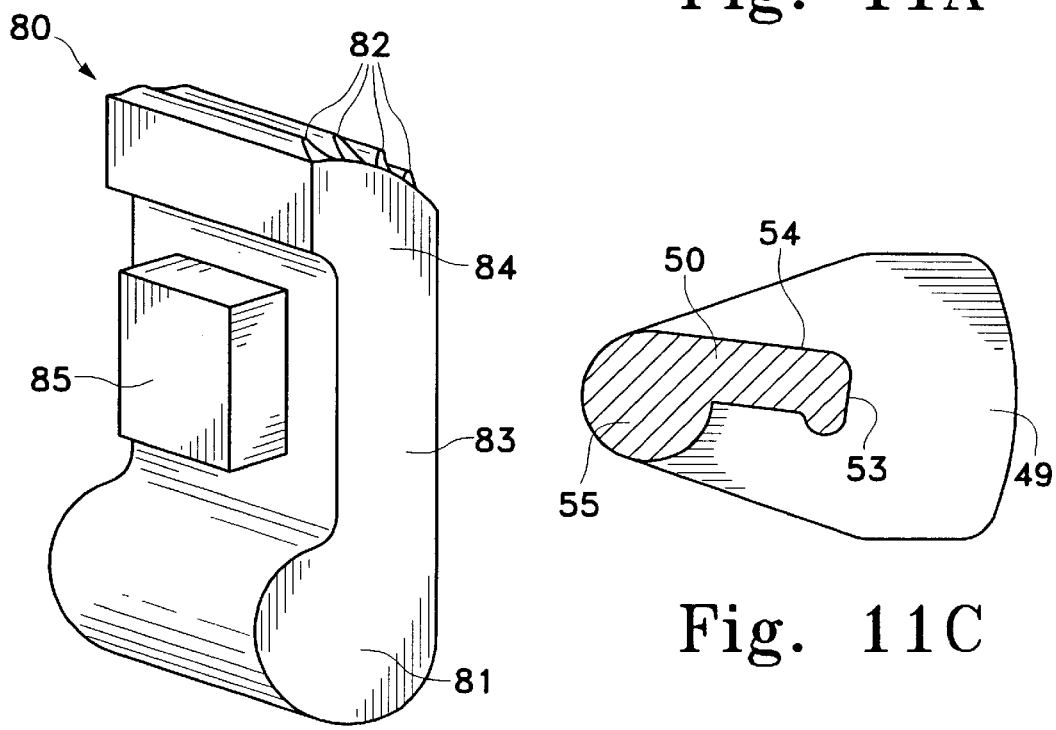

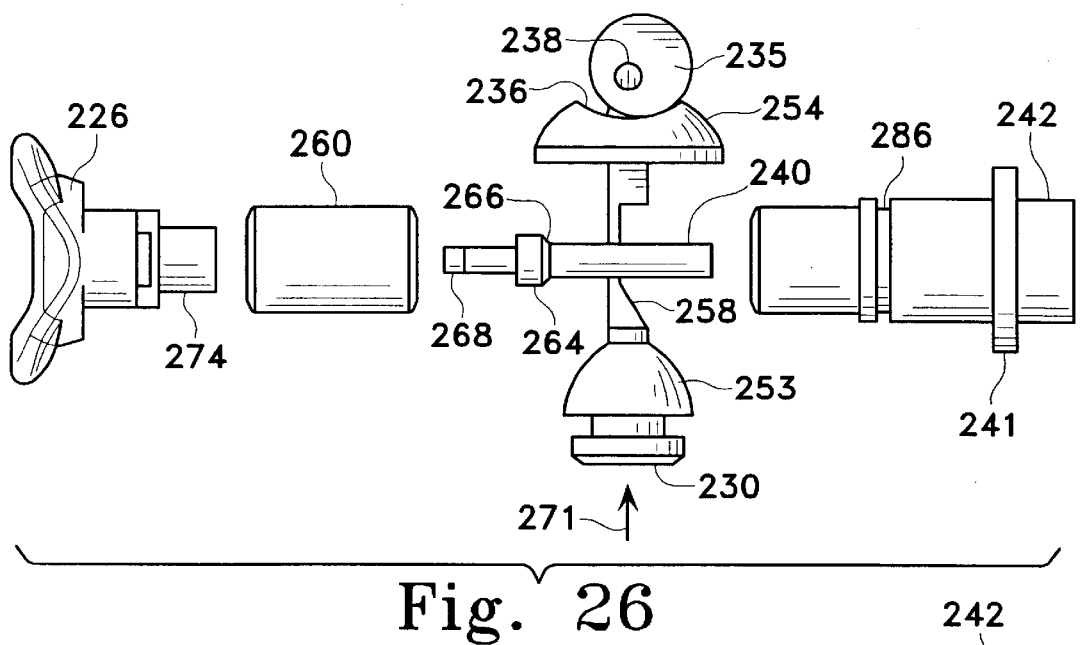
Fig. 26
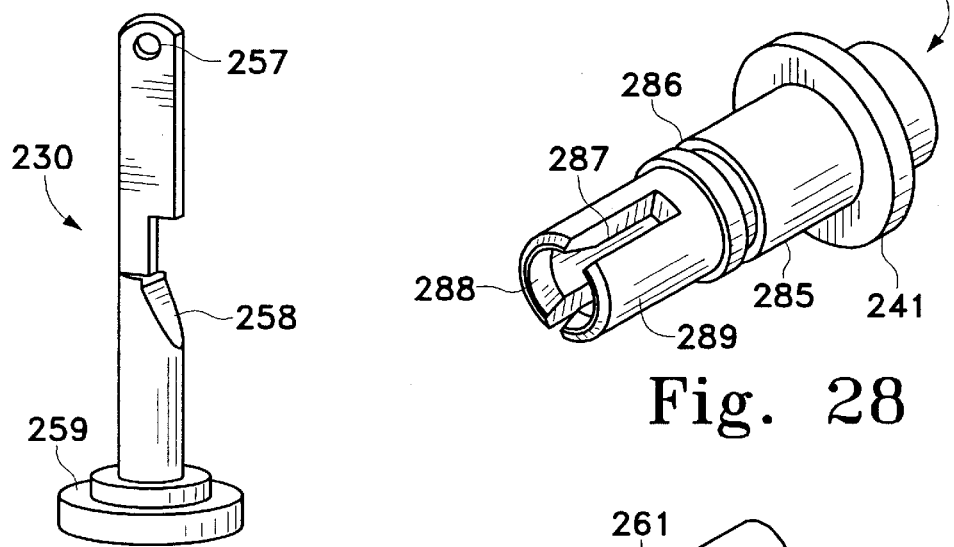
Fig. 27
Fig. 28
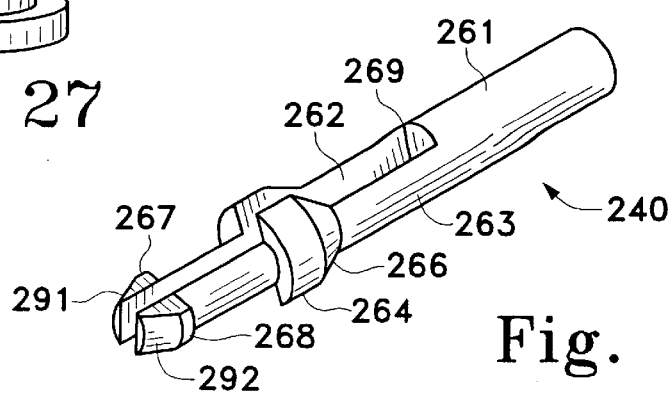
Fig. 29

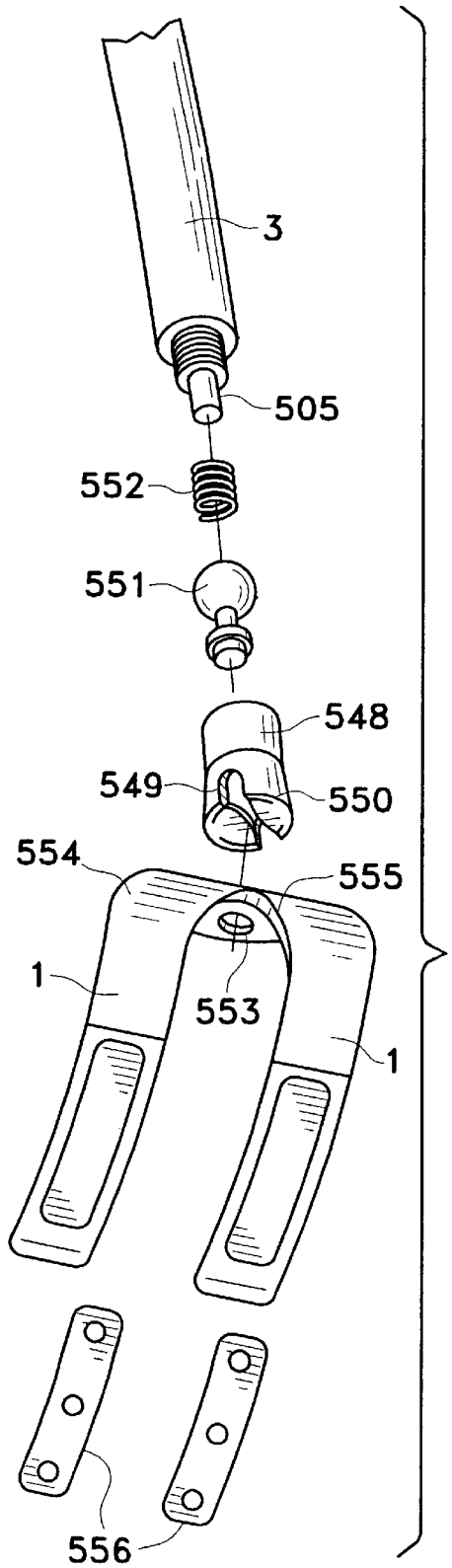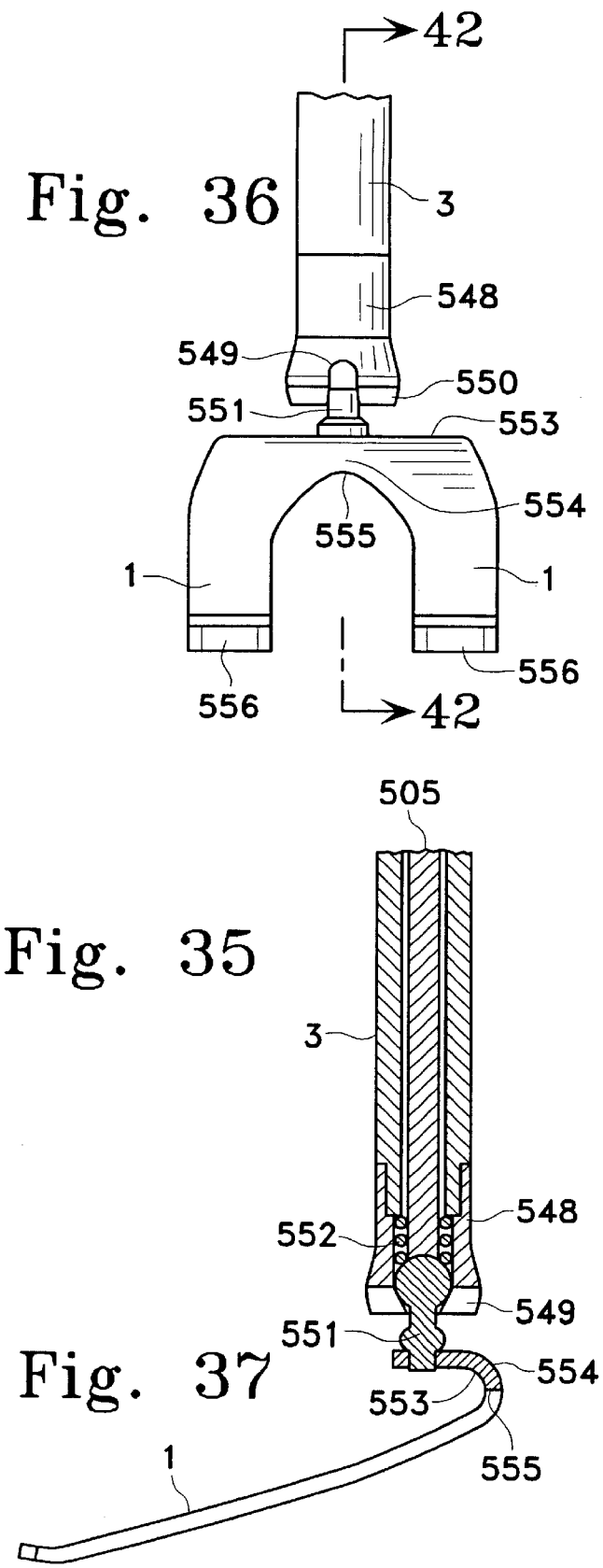

SURGICAL INSTRUMENTS AND PROCEDURES FOR STABILIZING A LOCALIZED PORTION OF A BEATING HEART

CROSS-REFERENCE TO RELATED APPLICATIONS

This application is a continuation-in-part of U.S. application Ser. No. 08/931,158 filed Sep. 16, 1997, now U.S. Pat. No. 6,036,641 which is a continuation-in-part of U.S. application Ser. No. 08/789,751 filed Jan. 27, 1997, pending which is a continuation-in-part of U.S. application Ser. No. 08/603,758 filed Feb. 20, 1996 now U.S. Pat. No. 5,894,743.

FIELD OF THE INVENTION

The present invention relates generally to surgical instruments, and more particularly to surgical retractor, instrument mount, and tissue stabilizer devices for use during coronary artery bypass graft surgery.

BACKGROUND OF THE INVENTION

Diseases of the cardiovascular system affect millions of people each year and are a leading cause of death throughout the world. The cost to society from such diseases is enormous both in terms of the number of lives lost as well as in terms of the costs associated with treating patients through traditional surgical techniques. A particularly prevalent form of cardiovascular disease is a reduction in the blood supply leading to the heart caused by atherosclerosis or other condition that creates a restriction in blood flow at a critical point in the cardiovascular system that supplies blood to the heart.

Treatment of such a blockage or restriction in the blood flow leading to the heart is, in many cases, treated by a surgical procedure known as a coronary artery bypass graft (CABG) procedure, more commonly known as a "heart bypass" operation. In the CABG procedure, the surgeon "bypasses" the obstruction to restore normal blood flow to the heart either by attaching an available source vessel to the obstructed target coronary artery or by removing a portion of a vein or artery from another part of the body, to use as a graft, and installing the graft between a point on a source vessel and a point on a target artery.

To restore the flow of blood to the heart, the CABG procedure requires that a fluid connection be established between two vessels. This procedure is known as an "anastomosis." Typically, a source vessel, such as a source artery with an unobstructed blood flow, i.e., the left internal mammary artery (LIMA), or a bypass-graft having one end sewn to an unobstructed blood source such as the aorta, is sewn to a target occluded coronary artery, such as the left anterior descending (LAD) artery or other vessel, that provides blood flow to the muscles of the heart.

Although the CABG procedure has become relatively common, the procedure itself is lengthy and traumatic and can damage the heart, the cardiovascular system, the central nervous system, and the blood supply itself. In a conventional CABG procedure, the surgeon makes an incision down the center of the chest, cuts through the sternum, performs several other procedures necessary to attach the patient to a heart-lung bypass machine, cuts off the blood flow to the heart, and then stops the heart from beating in order to complete the bypass. The most lengthy and traumatic surgical procedures are necessary, in part, to connect the patient to a cardiopulmonary bypass (CPB) machine to continue the circulation of oxygenated blood to the rest of the body while the bypass is completed.

In recent years, a growing number of surgeons have begun performing CABG procedures using surgical techniques especially developed so that the CABG procedure could be performed while the heart is still beating. In such procedures, there is no need for any form of cardiopulmonary bypass, no need to perform the extensive surgical procedures necessary to connect the patient to a cardiopulmonary bypass machine, and no need to stop the heart. As a result, these beating heart procedures are much less invasive and the entire procedure can typically be achieved through a small number, typically one or two, comparatively small incisions in the chest.

Despite the advantages, the beating-heart CABG procedure is not universally practiced, at least in part, because of the difficulty in performing the necessary surgical procedures using conventional surgical instruments. For example, it has been difficult for the surgeon to access the required areas of the heart requiring revascularization. In addition, the various surgical steps that are required to be performed on the heart itself are more difficult to perform because the heart muscle continues to move and contract to pump blood throughout the duration of the procedure.

The specific portion of the surgical procedure that creates the anastomosis in the beating-heart CABG procedure is particularly difficult. Completion of the anastomosis requires placing a series of sutures through extremely small vessels on the surface of the heart while the heart muscle continues to beat. Moreover, the sutures must be carefully placed to ensure that the source vessel or graft is firmly attached and will not leak when blood flow through the vessel is established. In cases where the target coronary artery is temporarily obstructed, for example, to improve the surgeon's visibility and avoid excessive blood loss, it is also important that the anastomosis procedure be performed rapidly to avoid ischemic damage to the heart.

Further adding to the difficulty of the procedure is the fact that the working space and visual access are often quite limited. The surgeon may be working through a small incision in the chest, for example, or may be viewing the procedure on a video monitor if the site of the surgery is viewed via surgical scope. The vessel, and particularly the arteriotomy to which a source vessel is to be anastomosed, may also be very difficult for the surgeon to see as it may be obscured more or less by layers of fat or other tissue.

The beating-heart CABG procedure could be greatly improved if the heart could be accessed and stabilized during the procedure such that the motion of the heart, particularly at the site of the anastomosis, is minimized even though the heart continues to beat and supply blood to the body. The beating-heart CABG procedure could be further improved if the target vessel, and specifically the arteriotomy was presented to the surgeon in a way that allows sutures to be easily placed.

In view of the foregoing, it would be desirable to have improved devices for accessing and effectively stabilizing the beating heart at the site of the anastomosis. It would be desirable to have a low-profile, atraumatic stabilizing device that stabilizes the beating heart at the site of the anastomosis and provides a favorable presentation of the target vessel and the arteriotomy. It would be further desirable to provide a mount for the stabilizing device, or other instruments, that allows the stabilizing device to be easily maneuvered to the desired position and orientation, fixedly secured until the procedure is completed, and then easily removed from the site of the anastomosis. It would also be desirable to have a retractor system for use in conjunction with the stabilizer that provides unobstructed and organized access to the areas of the heart requiring revascularization.

SUMMARY OF THE INVENTION

The present invention will be described for use in stabilizing the beating heart during CABG surgery, but the invention is not limited thereto, and is contemplated to be useful for other surgical procedures requiring body tissue or organs to be immobilized or stabilized.

The present invention involves various aspects of tissue stabilizer devices, and in particular a tissue stabilizer for use in immobilizing or stabilizing a portion of the beating heart using a compressive force delivered to the heart via the tissue stabilizer. The stabilizer may include a stabilizer base and a shaft. The shaft may be secured within an appropriate instrument mount preferably fixed to a retractor or other stable platform. The stabilizers of the present invention provide improved access to a surgical site at a target vessel on the surface of the heart and may include features which facilitate optimal presentation of the target vessel.

One aspect of the present invention involves an apparatus for stabilizing a localized portion of a beating heart comprising a base member having a wire frame coupled to the base member. The base member is preferably substantially rigid having at least one contact area adapted to frictionally engage the surface of the beating heart adjacent a first side of a target vessel. The wire frame may have a frame portion adapted to engage the beating heart adjacent a second side of said target vessel opposite to the first side and at least one leg portion connecting the frame to the base member. Preferably, the leg portion is substantially perpendicular to the frame portion. In a preferred embodiment, the frame portion is parallel to a central axis of the base member.

The leg portion is preferably flexible relative to the base member and may have a vertically relieved portion in the area where it would cross over the vessel between the contact area and the frame portion. In a preferred embodiment, the leg portion is formed from a unitary length of wire material. The wire material may be selected from stainless steel or titanium and may have a round or square cross-section. In one embodiment, the frame portion is vertically offset from the contact area, preferably by a distance of about 0.05 inches to about 0.2 inches. The contact area may be planar or curved to conform to the surface of the heart. The base member may have more than one contact area and most preferably two contact areas separated by an open space.

A shaft may be connected to the base member. Preferably, the base member of the stabilizer is operably connected to the distal end of the shaft. The shaft may be any configuration suitable for delivering the required compressive forces to the base member, but is preferably a substantially rigid shaft. The shaft may be straight, or more preferably, curved.

Preferably, the wire frame is moveable relative to the base member. In one embodiment, the base member includes a channel for slidably receiving at least a portion of the leg portion. The leg portion may have a plurality of detented positions with the channel. The detented positions may result from the channel having a plurality of teeth and the leg portion having a plurality of mating teeth adapted to engage the channel teeth. The position of the wire frame relative to the base member may be manually positioned between the detented positions.

The wire frame may be also be moveable using a rack and pinion arrangement, a threaded shaft and collar arrangement, or other like driving mechanism. In one embodiment, the base member includes a pinion gear having a plurality of gear teeth and the leg portion includes a rack having a plurality of mating teeth adapted to engage the gear teeth on the pinion. The wire frame can be moved in and out relative to the base member by rotating the gear. In another embodiment, the base member includes a threaded shaft rotatably coupled to the base member and the leg portion includes a collar having a threaded interior adapted to receive the threaded shaft. In that case, the wire frame can be moved in and out relative to the base member by rotating the threaded shaft causing the collar to move along the shaft.

The frame portion may have a first end and a second end each having a leg portion extending therefrom. Each leg portion may be removably attached to said base member. The base member may include a first and second channel for slidably receiving each leg portion. The wire frame may preferably be attached to from either side of the base member. When the wire frame is attached to the base member using two leg portions, the wire frame is preferably detachable from said base member to facilitate its removal from a completed anastomosis on the target vessel.

In another aspect of the present invention, an apparatus for stabilizing a localized portion of beating heart may include a base member having a post which is offset from the center of the base member. In a preferred embodiment, a substantially rigid base member is formed from a unitary piece of sheet material having a first side and second side. The base member may have a first section adapted to contact the surface of the beating heart and a second section at a fixed angle relative to the first section. The first section defines a first contact surface, a second contact surface and an open space between said first and second contact surface. A first end of the post is connected to the second section at a location which is offset from the open space between the first and second contact surfaces. A second end of the post terminates with at least a portion of a ball extending therefrom.

A shaft may be connected to the second end of the post. Preferably, the distal end of the shaft has a socket operably engaged with the portion of the ball at the end of the post. Preferably, the shaft is curved and substantially rigid.

In one embodiment, the angle between the first section and the second section may be from about 75 degrees to about 105 degrees, most preferably about 90 degrees, and the post is attached to and extends from the first side of the sheet material. In another embodiment, the angle is more than about 120 degrees and the post is attached to and extends from the second side of the sheet material.

In another aspect of the present invention, the apparatus for stabilizing a localized portion of a beating heart includes a substantially rigid base member having at least one surface adapted to contact the surface of the heart and a post having a first end moveably coupled to the base member and a second end having a ball or a ball-shaped member extending therefrom. A shaft, preferably a rigid shaft, may be provided with a distal end having a socket operably engaged with the ball.

In one embodiment, the base member has a first section having at least one surface for contacting the surface of a heart and a second section adjacent the first section. Preferably, the moveable post is attached to the second section. The second section may be at an angle relative to the first section. The second section may have a slot adapted to receive the first end of the post which is moveable within the slot from a first position to a second position.

In another embodiment, at least a portion of the base member has a curved outer profile and the post is mounted to a top member having an interior profile adapted to engage and concentrically rotate about the curved outer profile. The base member may have at least one elongate slot. The top member may have one or more extending features or tabs engaged within the slot or slots. Preferably, the interior profile of the top member is close fitting with the curved outer profile of the base member. Most preferably, the top member encircles more than 180 degrees of the base member thereby capturing the base member within the top member.

In another aspect of the present invention, the apparatus for stabilizing a localized portion of a beating heart includes a base member having a post attached to a pivotable link member. Pivoting the link to one or more different positions correspondingly moves the post to one or more different positions, including positions offset from the center area of the base member in a right or left direction. In a preferred embodiment, the base member has at least one surface adapted to contact the surface of the heart. The link member may be pivotably coupled to the base member at a predetermined pivot point and has a first link end spaced a distance away from the pivot point. A first end of the post is attached to the first link end and a second post end includes at least a portion of a ball extending therefrom. A shaft, preferably a rigid shaft, may be operably coupled to the ball. Preferably, the shaft has a socket an a distal end which engages the ball.

The link member may also have a second link end opposite the first link end. The second link end may be releasably locked to said base member to substantially prevent relative movement of the link member relative to the base member. The second link end is releasable such that the link member can be pivoted about the pivot point to allow the post to be moved from one position to another. Preferably, the link member pivots about a pivot pin extending from the base member. The base member may have a first contact surface, a second contact surface and an open space therebetween. The link member preferably provides a first position where the post is laterally offset from the open space in a first direction and second position where the post is laterally offset from the open space in a second direction. Thus, the post can be advantageously moved from a left-hand position to a right-hand position.

These and other features of the present invention will become more fully apparent from the following description and appended claims.

BRIEF DESCRIPTION OF THE DRAWINGS

FIG. 4 is a perspective view illustrating an exemplar bar assembly.

FIG. 5 is a perspective view illustrating a moveable housing associated with the retractor drive.

FIG. 6 is a perspective view illustrating a retractor drive handle assembly.

FIG. 8 is a top view in partial cross-section illustrating the platform blade and retractor drive assembly in an engaged position.

FIG. 9 is a cross-sectional view taken along line 9—9 shown in FIG. 8.

FIGS. 11A, 11B, and 11C illustrate a preferred platform blade latch. FIG. 11A and 11B are top and front plan view, respectively.

FIG. 11C is a cross-sectional view taken along line 11C—11C as shown in FIG. 11B.

FIG. 12 is a perspective view showing a preferred suture lock.

FIG. 26 is an exploded assembly view showing selected components of a preferred closing mechanism.

FIG. 27 is a perspective view illustrating a preferred instrument mount cam post.

FIG. 28 is a perspective view illustrating a preferred instrument mount release button.

FIG. 29 is a perspective view illustrating a preferred instrument mount follower post.

FIG. 35 is an exploded perspective view of a contact member of the stabilizer shown in FIGS. 33 and 34.

FIG. 36 is a rear plan view of the contact member of FIGS. 33, 34 and 35.

FIG. 37 is a cross-sectional view of the contact member of FIG. 36 taken along line 37—37.

DETAILED DESCRIPTION

Figure 1:
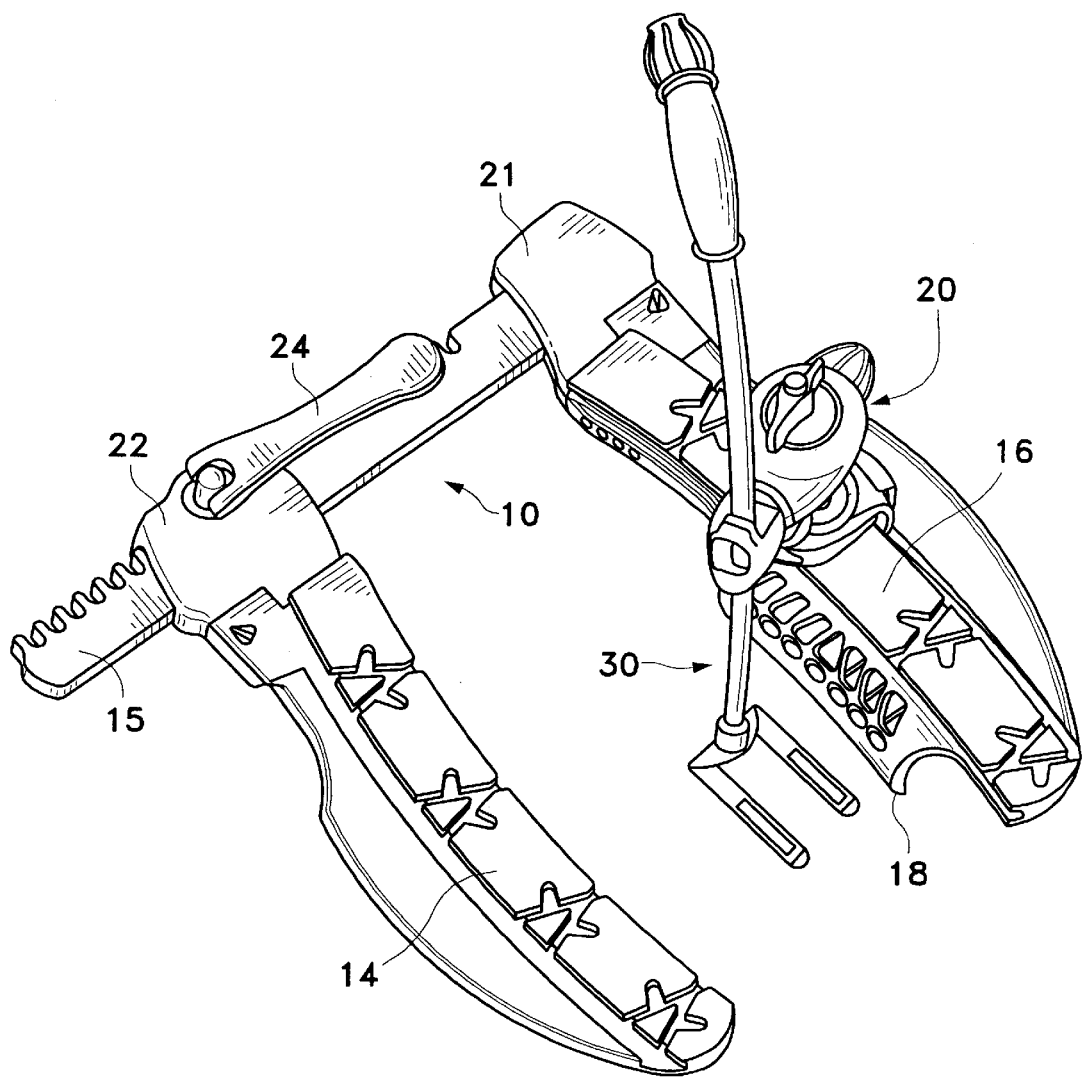
FIG. 1 is a perspective view illustrating a cardiac surgery system according to the principles of the present invention.

The present invention involves surgical instruments stabilizing the heart and methods for their use. The present invention may also include a mount that allows various instruments to be easily positioned within the surgical working space, locked or secured into a desired position for the duration of a particular surgical procedure, and then easily and safely removed from the working space. The present invention may also involve a retractor system or assembly for accessing the heart.

Although the instruments and methods of the present invention may have application in both conventional stopped-heart and beating heart procedures, they are preferably used to access and stabilize the beating heart during a minimally invasive coronary artery bypass graft (CABG) operation which has been specially developed to facilitate completion of an anastomosis, typically between a target artery and a bypass graft or source artery, without requiring cardiac arrest such as cardioplegia or fibrillation and without cardiopulmonary bypass (CPB). Further, although the instruments for accessing and stabilizing the beating heart can be applied in a number of different surgical contexts involving various incisions and surgical approaches to the heart as are known in the art, the instruments and devices described herein are most advantageously employed in a CABG procedure wherein the heart is accessed through only one or two minimally invasive incisions in the chest.

Although the particular source vessel and target artery of the anastomosis are determined clinically, a common minimally invasive bypass procedure on the beating heart includes an anastomosis which forms a connection between the left internal mammary artery (LIMA) as the source artery, and the left anterior descending artery (LAD) as the target artery. To complete the anastomosis, the surgeon must dissect a portion of the LIMA by separating it from the internal chest cavity. Once dissection of the LIMA is achieved, the surgeon may attach the dissected LIMA to the target coronary artery, i.e., the LAD by way of creating an anastomosis.

In this example, the present invention may involve a number of discreet components that facilitate access to the anastomosis site, allow various instruments or devices to be maneuvered and secured in place, and provide stabilization of the heart. The various stabilizer embodiments of the present invention may be used to stabilize the beating heart during at least the portion of the procedure during which the surgeon completes the anastomosis of the LIMA to the LAD. The mount of the present invention may be used to facilitate convenient manipulation of the stabilizer, and other instruments or devices, to their desired position and allows the devices to be secured in that desired position. The retractor of the present invention may be used to provide access to the anastomosis site of the target artery on the heart itself. Although the LIMA to LAD anastomosis is provided as one example, it is readily appreciated that the techniques and instruments described herein may be applied to other procedures depending on the clinical diagnosis and the patient's anatomy.

Although each component of the present invention may be used separately with great benefit, the components are preferably used in unison to provide a surgical system which provides an unobstructed and organized surgical field, exceptional instrument maneuverability and access to the heart facilitating total revascularization of the heart if required, and effective vessel stabilization during the anastomosis procedure. Although the present invention will have application whether access to the heart is achieved by way of a full-stemotomy, mini-stemotomy, para-sternotomy, thoracotomy or other known approach, the exemplar embodiments described below will be generally described with reference to a coronary artery bypass procedure using a mid-sternal approach.

Referring to the figures wherein like numerals indicate like elements, an exemplar surgical system for performing a mid-sternal surgical procedure on the beating heart is illustrated in FIG. 1 and includes retractor assembly 10, mount assembly 20 and stabilizer assembly 30.

Retractor assembly 10 generally includes a pair of opposing blades adapted to engage opposite sides of a sternal incision, or other incision, and a drive mechanism constructed to force the blades, and thus the sternum apart. Using the drive mechanism, the sternum may be spread to the desired opening, thus providing the desired access and direct visualization of the thoracic cavity. If desired, the heart may be positioned or oriented to best present the target vessels for anastomosis. This positioning may be established, for example, through the strategic placement and tensioning of sutures in the pericardial sac, by appropriately placing the patient in the Trendelenburg position, or by using a heart positioner in the form or a strap or pad or the like.

Once the target vessel is in the desired position, at least one component of stabilizer assembly 30 is brought into contact with the beating heart adjacent the target site of the anastomosis. The surgeon then applies a stabilizing force to the beating heart via the stabilizer assembly 30 which may then be fixed in place, preferably to the retractor assembly 10 by way of mount assembly 20. The stabilizing force supplied by the stabilizer assembly substantially eliminates movement of the heart in the area of the anastomosis so that the surgeon may accurately and efficiently perform the required anastomosis (or other surgical procedure). After the anastomosis has been completed, the stabilizing force is released and the contacting component of stabilizer assembly 30 is removed from the anastomotic site.

Figure 45:
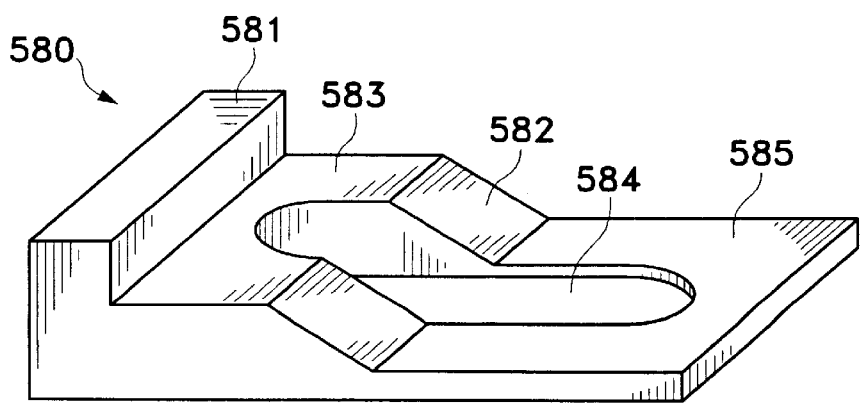
FIG. 45 is a perspective view of the locking clip of FIG. 44.

Each of the principal components, the preferred surgical system, and their methods of use are separately described in detail below. A preferred retractor is described below with reference to FIGS. 2–12. A preferred stabilizer or instrument mount according to the principles of the present invention is described below with reference to FIGS. 13–32. Preferred stabilizer embodiments according to the principles of the present invention are described below with respect to FIGS. 33–44. A preferred surgical system and methods for performing a coronary artery bypass on a beating heart according to the principles of the present invention is described below with respect to FIG. 45.

The Retractor

The preferred retractor generally involves a drive mechanism and a pair of opposing blades adapted for insertion into an incision and for engaging opposite sides of the incision. The drive mechanism functions in some manner to urge the opposing blades apart, thus forcing opposite sides of the incision open to allow surgical access through the incision. For purposes of performing a coronary artery bypass, the incision may be any suitable incision which provides the desired access to the thoracic cavity, and more specifically a desired area of the heart. For purposes of example only, the retractor of the present invention will be described with respect to a mid-sternal incision, however skilled artisans will recognize that many aspects the invention are equally applicable to other surgical approaches to the heart, for example, by way of a thoracotomy, or other suitable access approach.

When the heart is accessed by way of an incision through all or a portion of the sternum, the opposing blades are adapted to be inserted into and engage opposite sides of a sternal incision such that the severed sternum may be forced apart by the action of the opposing blades to create a working space for operating on the heart. Typically, the drive mechanism is constructed to spread the opposing blades apart in a generally parallel fashion, however, the parting motion may also have a significant curvilinear or angular component as well.

In one embodiment, the blades may be permanently, integrally, or inseparably formed with a drive mechanism. Preferably however, at least a portion of the blades are separable from the drive mechanism. That is, at least some of the features and functions associated with the retractor blades are allocated to a structural component which is separate, separable, or otherwise detachable from the drive mechanism. The separate component and the drive mechanism may be manufactured independently and then subsequently assembled at the factory or, more preferably, at the point of use.

A retractor construction having a separable component allows the features and functions of the drive mechanism to remain separate from the remainder of the retractor assembly and vice versa. This allows a greatly simplified or depopulated drive mechanism and allows the separable component to have a much more sophisticated construction with increased features and functionality. Accordingly, the simplified drive mechanism, which is typically required to be made from a hardened steel, is easier and more economical to manufacture and easier to maintain, clean and sterilize post surgically. Moreover, the separate component can be economically made from materials or processes that allow for the intricate structural features which provide superior functionality.

In a preferred embodiment, the drive mechanism is constructed to be resterilized and reused a relatively large number of times, and the feature-rich separate component is constructed to be disposable, i.e. discarded after a single surgical use. Thus, the depopulated drive mechanism, which will be used over and over, can afford to be constructed to be quite robust with a view to materials and manufacturing processes that will support the rigors of such extended surgical service. The separable component, free from the typical functional requirements of the drive mechanism and the service requirements of extended surgical re-use, may preferably be constructed from any number of engineering materials to produce an economical component having the desired features and which may be discarded after a single use if desired.

Figure 2:
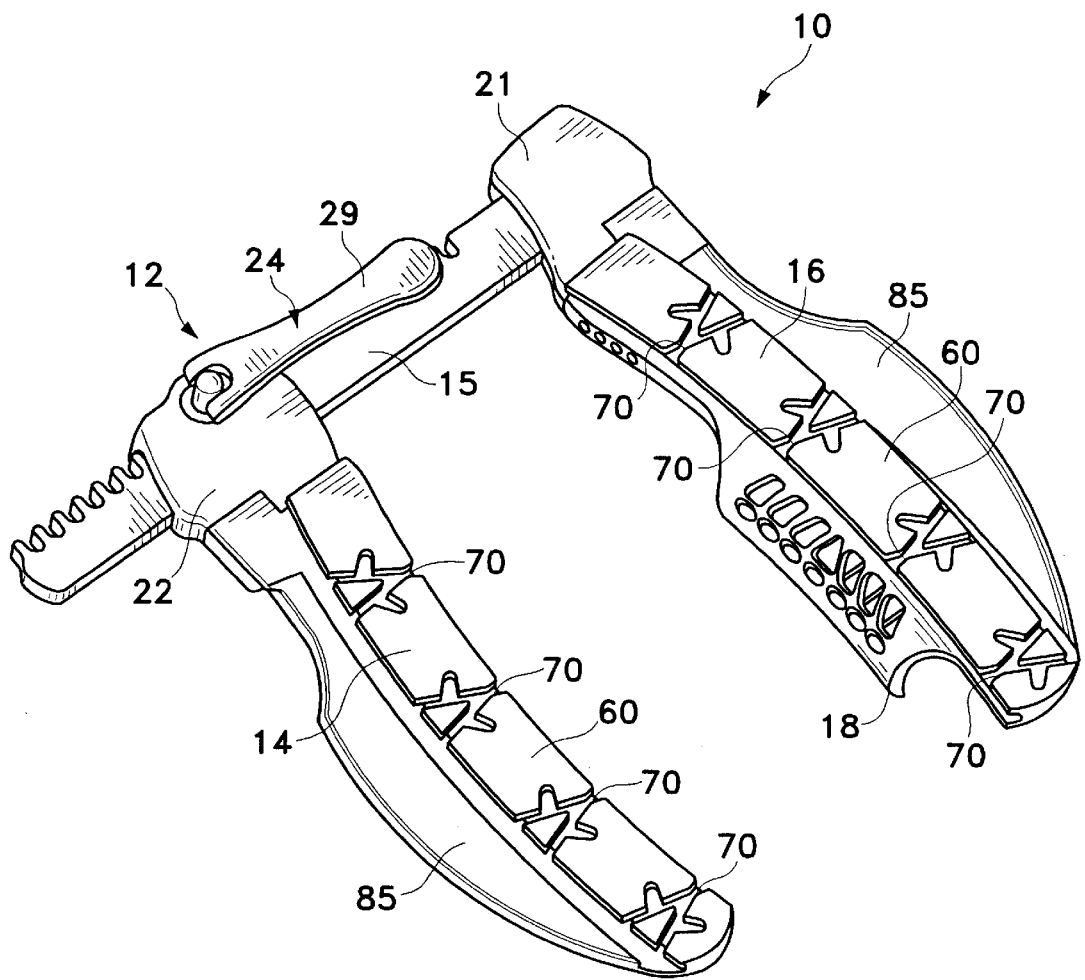
FIG. 2 is a perspective view illustrating a retractor assembly according to the principles of the present invention.

In a preferred embodiment, retractor assembly 10 comprises a drive 12 and first and second platform blades 14 and 16 detachably connected to drive 12, as illustrated in FIG. 2. Preferably first platform blade 14 and second platform blade 16 each have one or more channels or engaging members 18 adapted to engage opposite sides of an access incision. Activation of drive 12 forces apart first and second platform blades 14 and 16 thereby causing engaging members 18 to correspondingly force the incision open to provide access to the desired surgical site.

In the example of a sternal approach to the heart, engaging members 18 are adapted to engage each side of the incised sternum to reliably hold and engage the sternum as the sternum is forced open to expose the thoracic cavity and ultimately the heart. As best seen in FIG. 9, which illustrates a cross-section of second platform blade 16, engaging member 18 is generally in the form of a channel or the like, preferably having a U-shape, curved shape, or other shape suitable for engaging the incised sternum.

Preferably, engaging member 18 generally has a concave interior profile 17 for engaging and holding the sternum and a corresponding convex exterior profile 19 that is relatively smooth so as not to interfere with other surgical instruments, snag sutures or create other such difficulties. The engaging members 18 are preferably constructed to have sufficient strength to withstand the loads required to spread the sternum yet maintain a suitably low profile to facilitate easy insertion into the access incision and to require as little space within the working incision as possible.

It may be desirable to provide engaging members 18 with features to reduce trauma to the incision site, increase the traction against the sides of the incision, or both. A thin pad or layer of non-slip or atraumatic material (not shown) may be fixed, by way of an adhesive or other suitable fastening technique, to the interior profile 17 if desired to reduce slippage and trauma to the severed sternum or surrounding tissue. Alternatively, the desired features may be integrally fabricated into engaging members 18. For example, when platform blades 14 and 16 are injection molded components, traction features such as raised bumps, ribs, indentations, or the like can be molded integral into engaging members 18.

Figure 3:
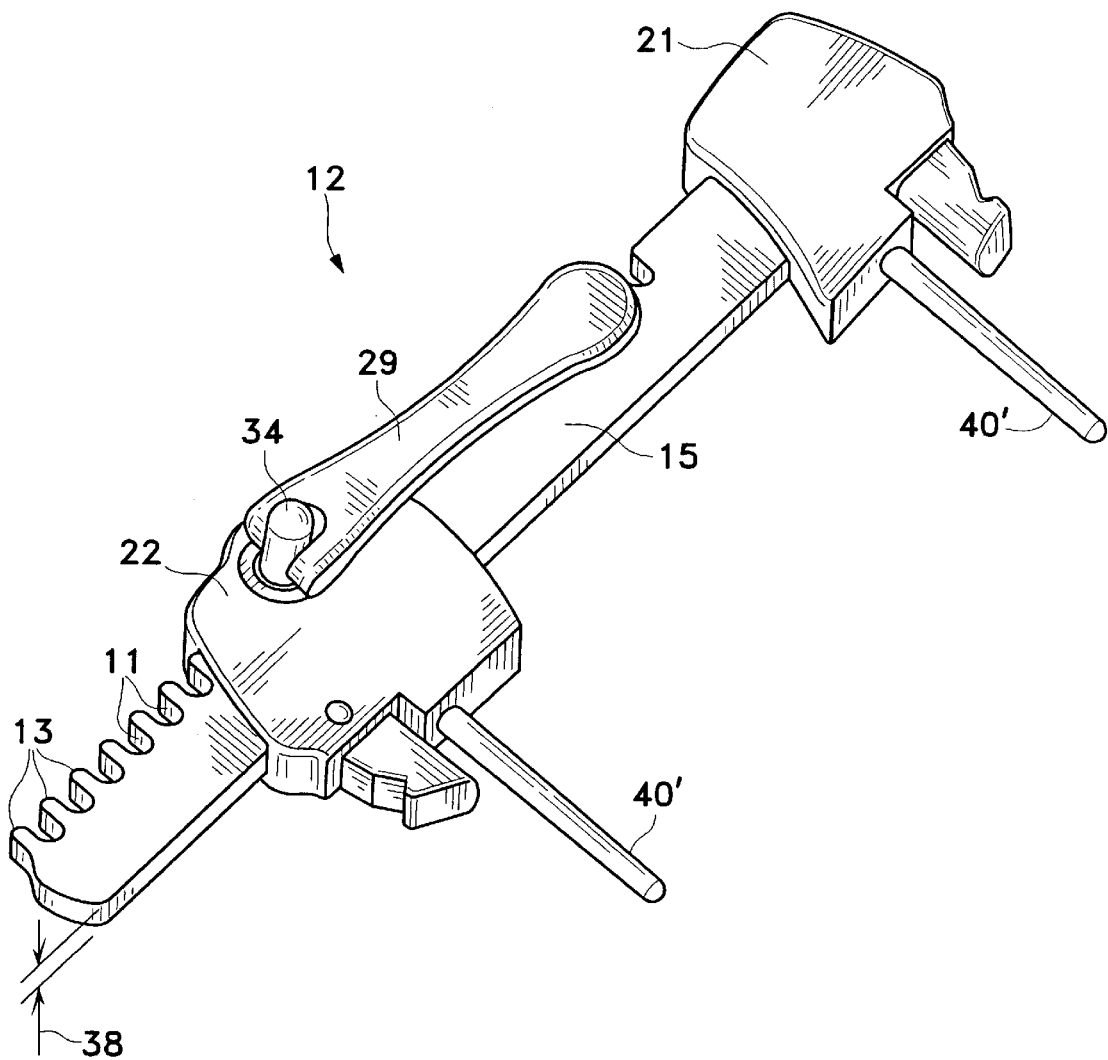
FIG. 3 is a perspective view illustrating a preferred retractor drive assembly.

Referring to FIGS. 2–6, drive 12 is preferably constructed to force the platform blades apart in generally opposite directions. Any type of drive mechanism which provides the desired separating action of the blades may be suitable. A common, substantially straight-line parting motion may be provided by a ratchet or rack arrangement as is generally known in the art. FIG. 3 illustrates a preferred drive 12 which involves a bar 15, moveable housing 22 and handle assembly 24 which facilitates movement of moveable housing 22 relative to bar 15. A first end of first blade 14 may be operably attached to moveable housing 22 and second blade 16 to bar 15.

In a preferred embodiment, bar 15 is a substantially rigid bar having a stationary or fixed housing 21 assembled thereto and thus forming bar assembly 23. Fixed housing 21 may be fastened to one end of bar 15 using one or more mechanical fasteners, an interference fit, suitable adhesive or bonding compounds, welding, or any other suitable fastening technique. A first end of second blade 16 is preferably operably attached to fixed housing 21. As with moveable housing 22, fixed housing 21 may be of any configuration which provides for the structural attachment of first and second platform blades 14 and 16.

Bar 15 preferably includes a number of teeth 13 evenly spaced along at least a portion of its length. Teeth 13 may have substantially parallel side portions 11 and may have radiused tops 25. The exterior edges of teeth 13 may be broken or radiused or have a chamfer 26 as shown. Handle assembly 24 preferably includes a means for engaging teeth 13 so as to drive moveable housing 22 relative to bar 15 to any desired position under load where it remains so positioned against the load without need for any applied input or holding force. The means for engaging teeth 13 could be any suitable gear, ratchet, cog or like mechanism. Bar 15 may also be adapted and used for receiving an instrument mount, such as those described in detail below.

In a preferred embodiment, moveable housing 22 is driven using one or more drive pins which may successively engage teeth 13 in a cogging manner. Handle assembly 24 includes drive handle 29 connected to first and second cylindrical drive bearings 31 and 32. Drive bearing 31 preferably has a raised boss 34 extending from one end to which drive handle 29 may be pivotally connected by way of pin 33. At the opposite end, drive bearing 31 has first drive pin 27 and second drive pin 28 extending therefrom and terminating at second drive bearing 32. First and second drive bearings 31 and 32 are spaced apart a distance 35 which is selected to be slightly greater than the thickness 38 of bar 15 such that a portion of bar 15 may be received between first and second drive bearings 31 and 32. The outside diameters of drive bearings 31 and 32 are selected so as to fit within guide holes provided in moveable housing 22. For example, the outside diameter of second drive bearing 32 is sized to accurately rotate within guide hole 36.

Moveable housing 22 has a bore 37 extending therethrough for receiving bar 15. Bore 37 generally has a shape corresponding to the dimensions of the cross-section of the portion of the bar 15 which is to pass through bore 36. With handle assembly 24 properly positioned within the guide holes provided in moveable housing 22, it may be assembled to bar 15 by placing the end of bar 15 within bore 36 and turning handle 29 such that first and second drive pins 27 and 28 become engaged with teeth 13. Once assembled in this manner, moveable housing 22 may be forced one way or the other along the length of bar 15 by turning handle 29, and thus drive bearings 31 and 32, to cause first and second drive pins 27 and 28 to progressively engage teeth 13 along bar 15.

As mentioned above, first and second platform blades 14 and 16 may be removably assembled to moveable housing 22 and fixed housing 21, respectively. Platform blades 14 and 16 may be attached in any suitable fashion including, for example, threaded connections or other mating features on the platform blades and housings themselves, ordinary or specialized mechanical fasteners, and cam or latching mechanisms adapted to secure the platform blades to the housings. In a preferred embodiment, both moveable housing 22 and fixed housing 21 are constructed with features that engage, secure and support first and second platform blades 14 and 16 in an operable position on drive 12, thus providing an assembled retractor 10 which is ready for surgical use.

Figure 7:
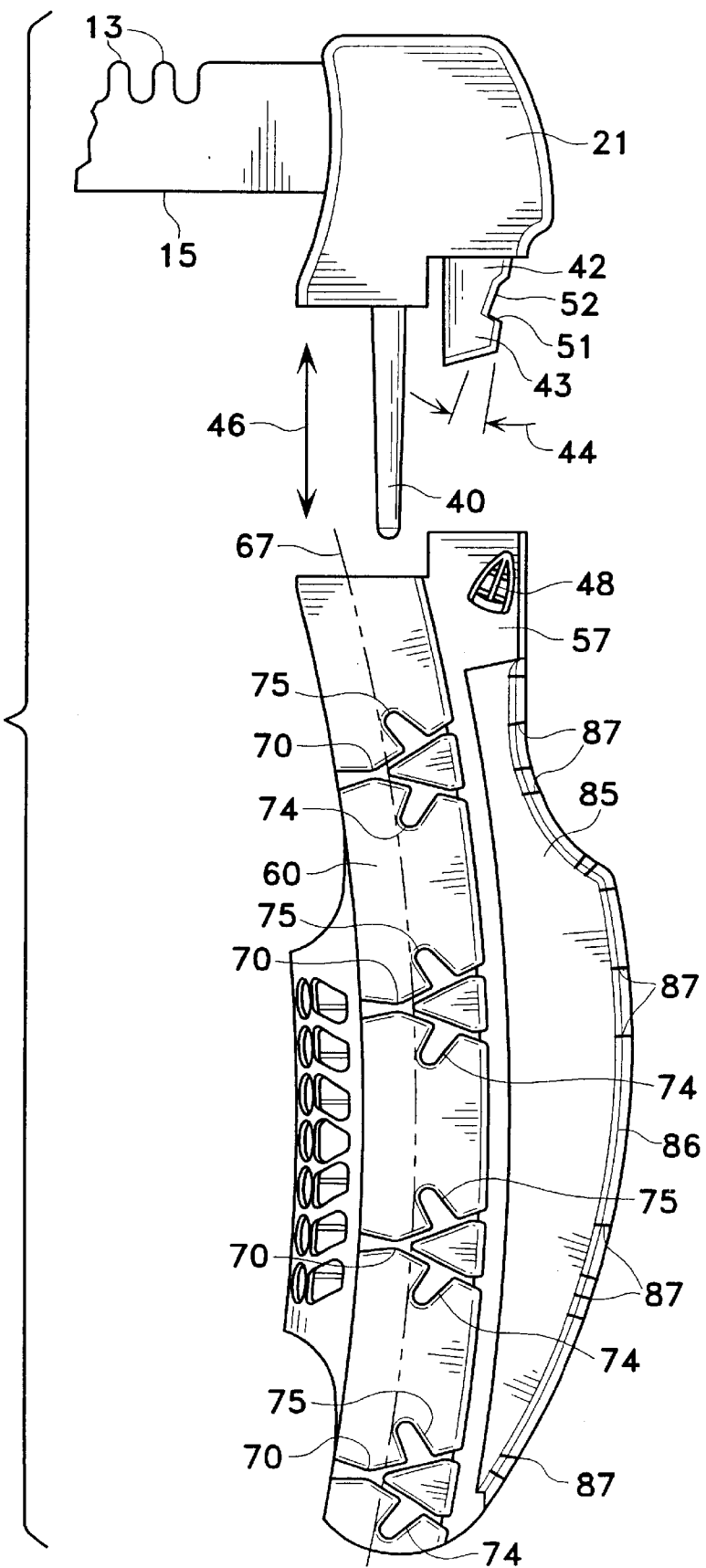
FIG. 7 is a top plan view illustrating a preferred platform blade and retractor drive assembly in an unengaged position.

Referring to FIGS. 7 and 8, second platform blade 16 is shown before and after assembly onto fixed housing 21. Preferably, at least one of the platform blade 16 or the fixed housing 21 has an extending protuberance, post or like feature which can be receivably engaged by the other of the platform blade or housing. In a preferred embodiment, fixed housing 21 is preferably constructed to have a latch post 42 adapted to be received within latch post cavity 45 provided in platform blade 16. Latch post 42 may have a hole, notch, protuberance, or other feature formed therein which may be engaged in any convenient manner by the platform blade 16 so that platform blade 16 becomes releasably locked in place for use.

In a preferred embodiment, latch post 16 has a notch which defines latch surface 51 and stop surface 52. Platform blade 16 has a latch member 48, best seen in FIGS. 11A–11C, having a latch body 50 constructed with surfaces 53 and 54 for engaging latch surface 51 and stop surface 52 respectively. Generally transverse to latch post cavity 45, platform blade 16 has a latch body cavity 56 having an opening towards upper surface 57 of platform blade 16 for receiving latch body 50 of latch 48.

Latch 48 is preferably constructed to engage and disengage latch post 42 by manual rotation of latch knob 49. Latch body 50 includes cylindrical portion 55 which provides for controlled rotation within latch body cavity 56. Latch body 50 may be biased towards the engaged position shown in FIG. 8 by way of any suitable spring element. Preferably, latch post 42 is provided with an angled tip 43 having a lead-in angle 44 which allows angled tip 43 to slide against second engaging surface 54 as latch post 42 begins to be received within latch post cavity 45. As latch post 42 is advanced further within latch post cavity 45, angled tip 43 causes latch 48 to rotate out of the way about cylindrical portion 55. Near the end of the advancement of latch post 42 within latch post cavity 45, the angled tip is advanced beyond latch body 50, and latch 48 (which is biased towards an engaged position) rotates into the engaged position with second engaging surface 54 biased against stop surface 52.

With latch 48 and latch body 50 snapped into the engaged position, any separating force encountered between platform blade 16 and fixed housing 21 is resisted by action of first engaging surface 53 against latch surface 51. With this configuration, the reaction force at first engaging surface 53 is advantageously borne by latch body 50 primarily in compression. Thus, since the loading is primarily compressive in nature, a high strength material is not required, and latch 48 can be made from standard engineering polymers, for example, such as polycarbonate.

When it is desired to remove platform blade 16 from drive 12, the operator simply turns latch knob 49, causing latch body 50 to be placed in a disengaged position relative to latch post 42. With latch 48 disengaged, latch post 42 of fixed housing 21 is free to be removed from latch post cavity 45 of platform blade 16. As is apparent from the Figures, a mirror image of the latch assembly described with reference to platform blade 16 and fixed housing 21 is provided to releasably attach platform blade 14 to moveable housing 22.

When the retractor assembly is used to gain access to the thoracic cavity, a good deal of force must be generated to create the desired opening. For example, a separating force in excess of 100 pounds may be required to be generated at each engaging member 18 to achieve the desired separation of a particular sternum. Such loads must be carried by the engaging members and transmitted to drive 12 by way of platform blades 14 and 16. Since platform blades are preferably made from a suitable engineering polymer (for example, a glass filled thermoplastic polyurethane resin), it may be desirable to provide a reinforcing member for each of platform blades 14 and 16 to ensure that platform blades 14 and 16 will not break or otherwise rendered inoperable as a result of the loads encountered during use.

Although the reinforcing members may be a permanent or removable members within the platform blades themselves, the reinforcing members are preferably one or more substantially rigid members extending from each of the fixed housing 21 and the moveable housing 22. In a preferred embodiment, fixed and moveable housings 21 and 22 have a pin extending therefrom which may be received within a mating cavity within first and second platform blades 14 and 16. The pin operates to spread the load developed in the mechanism over a larger internal area within the platform blades 14 and 16 and reduces the effective beam length of unreinforced platform blade material subjected to the operating loads. The pin may be straight pin 40' illustrated in FIG. 3. More preferably, fixed and moveable housings 21 and 22 have tapered pins 40 and platform blades 14 and 16 have mating tapered cavities 41 for receiving tapered pins 40. The tapered construction tends to allow the user to easily align pin 40 with cavity 41 and allows the pins 40 to fit relatively snugly within cavities 41 without significant binding during insertion that could otherwise occur between elongate pins and mating cavities which are designed to be very close fitting.

To provide sufficient load bearing reinforcement, the reinforcing pins 40 are preferably constructed of a substantially rigid material, such as steel, and are preferably at least about 0.75 inches long, more preferably at least about 1.125 inches long, and most preferably between about 1.25 inches to about 2.25 inches long. In a preferred embodiment, reinforcing pins 40 are made from AISI 420 stainless steel having a length of about 1.5 inches, an outside diameter near the housing of about 0.25 inches, and a 2 degree taper angle decreasing towards the free end of the reinforcing pins 40.

In the preferred embodiments just discussed, platform blade 16 can be removed from drive 12 with a substantially straight-line relative motion as indicated by arrow 46. This engagement action not only provides for simple and intuitive assembly in the operating room, but also represents a significant safety feature. Under certain rare circumstances, for example where the drive through neglect or misuse has become sufficiently damaged during use that it is unable to close and disengage from the sternum, an extremely dangerous situation can be created for the patient. In such exigent circumstances, the configuration described above may allow the drive to be separated from the in situ platform blades by releasing the latches and applying a sufficient amount of force in the direction indicated by arrow 46. Once the drive has been removed, the detached platform blades may be easily removed from the patient.

In addition to engaging members 18, detachable platform blades 14 and 16 may incorporate a wide variety of additional features which enhance the performance of the retractor system. For example, one or both of platform blades 14 and 16 may have mounting features to which various instruments used during the procedure can be secured. In the case where a stabilizer is to be secured to a retractor for operating on a beating heart, it is critical to minimize or substantially eliminate the amount of flex and motion attributable to each component and each connection between each component, from the component engaging the beating heart to the component which provides the sternal attachment. To this end, the engaging features 18 which engage the sternum are preferably part of a unitary platform blade structure which also includes mounting features to which a stabilizer and other instruments can be mounted. Since the mounting features and the sternal engaging features are part of the same component, and therefore there is no mechanical connection between the two, the stability of an attached instrument against the forces of a beating heart is greatly improved.

In a preferred embodiment, each of first and second platform blades 14 and 16 include mount features in the form of rails. The rails allow one or more instruments to be positioned at any desired location along the operable length of the rail. Preferably, the rails are oriented in a direction generally perpendicular to the direction of separation, in this case perpendicular to bar 15. The rails may be a recessed feature within the body of platform blades 14 and 16. More preferably, the mounting rails extend upwardly from the body of platform blades 14 and 16.

Referring to FIGS. 7–9, right platform blade 16 has rail 60 extending over at least a portion of the length of platform blade 16. Rail 60 may have a top portion and a bottom portion having a narrowed region adjacent said top portion. In one embodiment, Rail 60 preferably has a T-shaped cross-section. The T-shaped configuration has a top portion 61 and a narrowed portion 62, thus forming mounting tabs 63 and 64 which can be gripped by a number of appropriately constructed mounts.

The rail may be straight, curved, or a combination of straight and curved portions. Preferably, at least a portion of the T-shaped rail is curved in a manner which more closely follows the profile of the access or incision site (as seen, for example, see FIG. 45). In a curved rail configuration, instruments extending perpendicular to a generally central axis 67 of rail 60 will naturally point more towards a central area between the platform blades 14 and 16, and thus may require less positional adjustment or manipulation from their normal, natural or beginning position. In addition, all or a portion of top portion 61, and more specifically mounting tabs 63 and 64, may be tilted or angled inwardly at an angle 65 as shown.

Platform blade 16 may be also be provided with a number of suture holders or stays which can be used to organize or capture various sutures used in the course of a particular surgery. Since certain sutures are placed near the beginning of a CABG procedure, such as pericardial sutures used to position the heart, the placement of the suture stays in a manner which does not interfere with subsequent procedures and instruments is an important aspect of the present invention. Preferably, the suture stays are positioned such that placing and manipulating the sutures or the various instruments and instrument mounts employed during surgery can be accomplished without interfering with each other. Preferably, the location of the suture stays position the sutures below the level of the mounting tab 63 and 64 so that a mating instrument mount may traverse the entire operable length of rail 60 without interfering with the sutures.

Rail 60 may have one or more grooves, channels, slots or passageways for receiving a suture. In addition, a suture lock may be provided in the rail or elsewhere on platform blade 16 so that the suture may be fixed in place. To accommodate the use of pericardial sutures, which are often subjected to a significant amount of tension when used to position the heart, the suture locks must be adapted to hold the suture material even while under a significant amount of tensile loading.

In a preferred arrangement for organizing and locking sutures, and in particular tensioned pericardial sutures, rail 60 has at least one open slot or passageway formed therein for receiving the free end portions of a surgically placed suture. The passageways preferably extend across rail 60 and have a depth which allows the suture to lay at an elevation sufficiently below mounting tabs 63 and 64 so as not to interfere with an instrument mount sliding along rail 60. In a preferred embodiment the passageways extend through at least a portion of narrowed portion 62. Thus, the height 66 of narrowed portion 62 may be selected not only to provide sufficient space for a desired instrument mount to attach, but also to ensure that mounting tabs 63 and 64 are sufficiently raised above the surrounding features of platform blade 16 so that an instrument mount may be positioned and repositioned along rail 60 without disturbing or disrupting the sutures within the various passageways.

Figure 10:
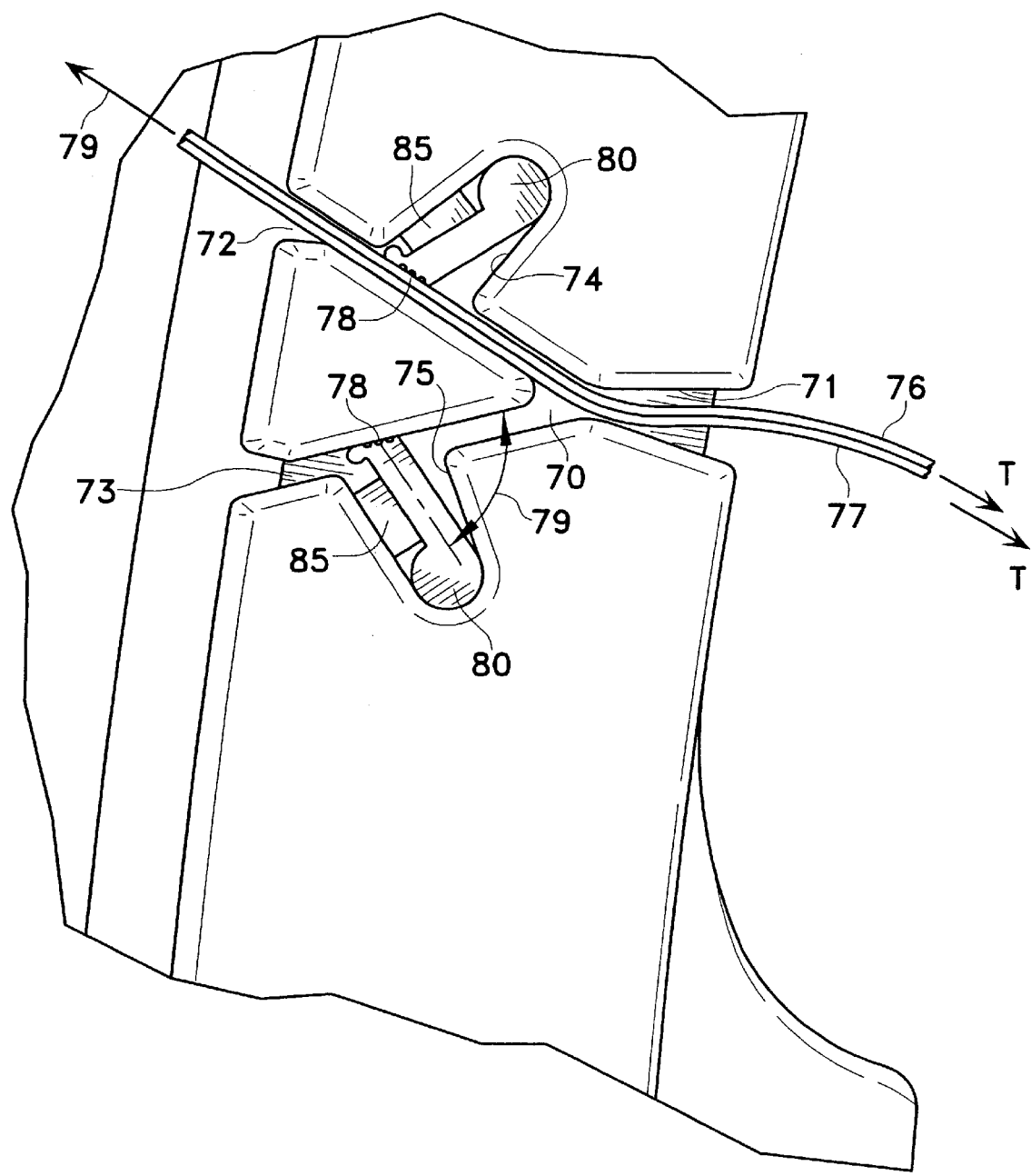
FIG. 10 is a partial top view illustrating a preferred suture stay arrangement s associated with a platform blade.

The passageways may be a single channel for receiving both free ends of a surgically placed suture or each end may have a separate channel. In a preferred embodiment, rail 60 has a number of bifurcated channels 70 at predetermined intervals along its length. Referring to FIG. 10, bifurcated channel 70 has a single entrance channel 71 which bifurcates into first and second exit channels 72 and 73. Entrance channel 71 and either one of exit channel 72 or 73 can be used in the same manner as a single channel, with both free ends 76 and 77 being routed together. Alternatively, both suture ends may be received within entrance channel 71 and then separated, one end within exit channel 72 and one end within exit channel 73.

A means for clamping the suture against movement within the suture channels may be provided on any of entrance channel 71 or exit channels 72 or 73. Preferably, suture locks are provided on each exit channel 72 and 73. This allows the surgeon to positively identify and unlock a desired suture end for further tension adjustments or other manipulation without unlocking or loosening the other end of the suture. In addition, placing each suture end 76 and 77 in separate exit channels 72 and 73, each with a dedicated suture lock, increases the maximum amount of tension that can be applied to a given suture. Exit channels 72 and 73 may have recesses 74 and 75, respectively associated therewith for receiving a suture lock adapted to secure the suture material within the channels.

A preferred suture lock 80 is illustrated in FIGS. 10 and 12. Suture lock 80 has a relatively rigid body 83 having a fixed or pivot end 81 which allows body 83 to pivot within the mating profile of recess 74 or 75. Pivoting the body 83 about pivot end 81 selectively engages and disengages free end 84 against the wall 78 of exit channel 72 or 73. Alternatively, suture lock 80 may be made from a more flexible material which, by nature of the elastic properties of the material, tends to flex about its fixed end instead of rotate. In a preferred embodiment, fixed or pivot end 81 is substantially cylindrical and recesses 74 and 75 have mating cylindrical surfaces.

Preferably, the suture lock is angled relative to the wall 78 so that it is self-locking in one direction. That is, the suture ends 76 or 77 (or both) operate on the free end 84 in such a way as to force it towards wall 78, and thus against the suture material, in proportion to the tension, T encountered by suture ends 76 or 77. Thus, within practical limits, the higher the tension the harder free end 84 will press or bite against the sutures placed therein. Conversely, when the suture ends are pulled in the direction indicated by arrow 79, the suture forces tend to pivot body 83 about pivot 81 such that free end 84 is rotated away from wall 84 allowing the suture to move relatively freely. Preferably, angle 79 between body 83 and wall 78 is nominally about 1 degree to about 30 degrees, more preferably about 5 degrees to about 15 degrees, most preferably about 10 degrees. Of course, angle 79 is greater as body 83 pivots to accept a suture placed within the suture channel.

Suture lock 80 may be biased towards the locked position, preferably using a small spring between the suture lock and the recess 75. In a preferred embodiment, a piece of resilient closed cell foam 85 is fixed to body 83 to provide the desired biasing effect. Free end 84 may optionally have a number of teeth or ridges 82 to ensure acceptable traction against the suture material.

Platform blades 14 and 16 may also be provided with soft tissue retainers to help control and retain the incised tissue and fat in the immediate vicinity of the blades. Referring to FIGS. 8 and 9, platform blade 16 includes integrally attached tissue retainer 85. Tissue retainer 85 is generally at a small distance 88 above the top of the engaging members 18. Tissue retainer 85 may be made from a flexible material, such as an elastomer, preferably a polyurethane elastomer having a durometer in the range of about 45 to about 75 Shore D, more preferably about 55 Shore D. In a preferred embodiment tissue retainer 85 is injection molded over the platform blade to form a permanent and inseparable assembly. Tissue retainer 85 may have a raised outer lip 86 and optionally having a plurality of slots 87 formed therein to receive and organize any loose suture ends. Tissue retainer 85 ensures that the tissue surrounding the access incision does not interfere with the operation of rail 60 or the suture holders and also provides a convenient location for attaching surgical drapes of the like without interfering with the operation of the retractor assembly.

Although some of the features of the present invention have been described, for illustration only, with respect to only one of the platform blades 14 and 16, it should be apparent that both platform blades 14 and 16 may have similar or identical features. Although not necessarily so, first platform blade 14 and second platform blade 16 are preferably substantially mirror images of each other.

The retractor assembly just described, provides a simplified drive mechanism for use in conjunction with multi-featured platform blades. In addition, a number of different platform blades may be provided for use with a single drive, for instance, tailored to different sized anatomy or the specifics of different surgical procedures. Thus, a number of platform blade configurations can be provided to an operating room and, based upon pertinent prevailing clinical factors, the proper configuration can be selected, mounted to drive 12, and used as described above to provide access to a desired location. Also, with the modular configuration new features and advancements can be rapidly incorporated into the platform blades and immediately introduced for use with existing simplified drives already in place in the operating rooms.

The platform blades themselves represent a surgical platform that allows instruments to be mounted and stabilized in virtually any position, even over already placed and secured sutures from the surgical site accessed by the retractor assembly. Described below are preferred instrument mounts for use in conjunction with rail 60 to secure a beating heart stabilizer or other instruments such as heart positioners, saline or medical air blowers, suction devices, surgical clamps, or vessel occluders.

The Instrument Mount

Figure 13:
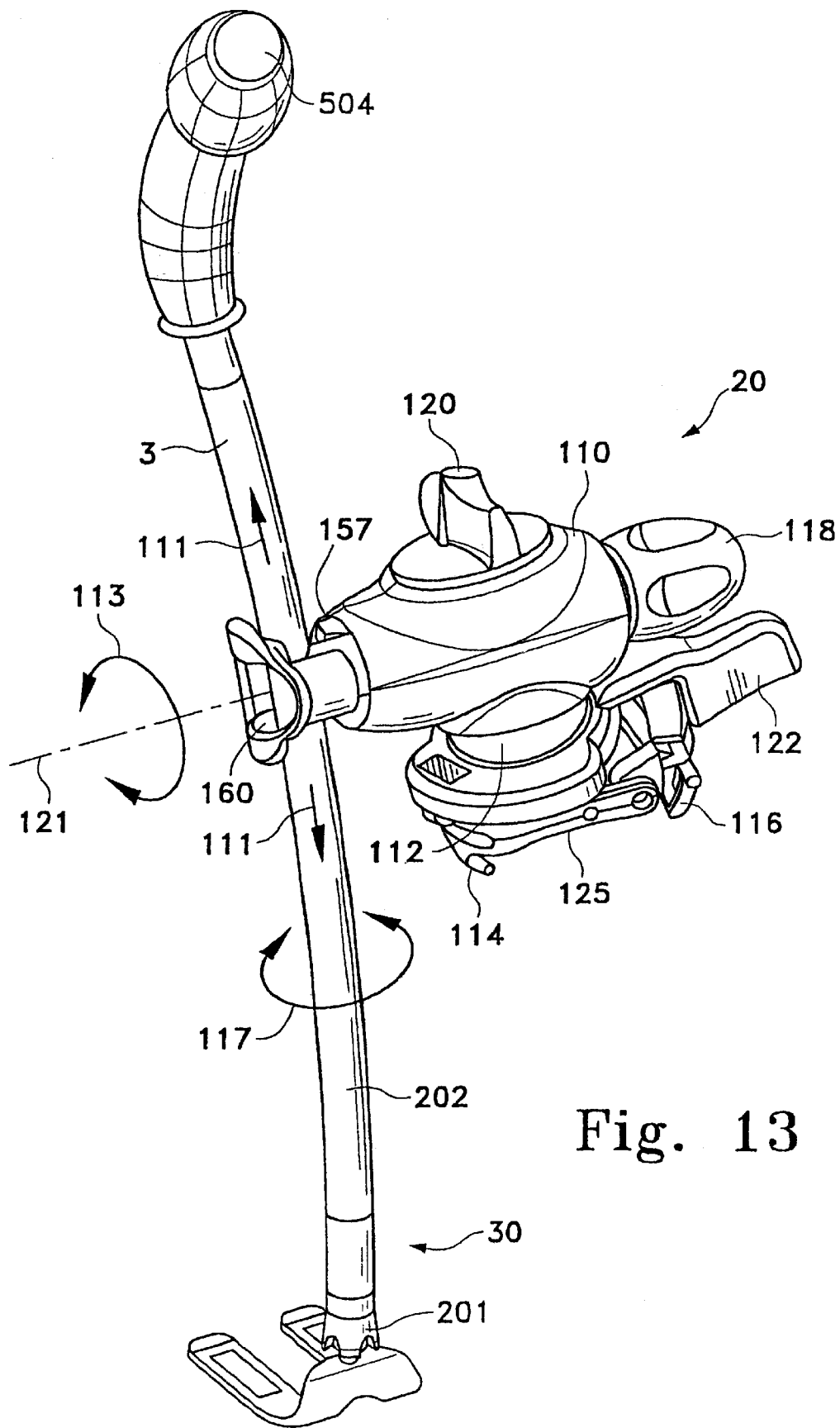
FIG. 13 is a perspective view illustrating an instrument mount assembly according to the principles of the present invention.

Referring to FIG. 13, a preferred instrument mount assembly 20 is shown for mounting an instrument, such as stabilizer assembly 30, to an instrument mounting rail such as described above with respect to rail 60 of platform blades 14 and 16. Mount assembly 20 includes mount base 115 having features to secure mount assembly 20 at a desired position on an appropriately configured mating rail or other suitable structure and includes a shaft locking mechanism for controlling and securing an instrument shaft in a desired position and orientation.

One important aspect of instrument mount assembly 20 is to provide the necessary degrees of freedom to allow the tissue stabilizer or other instrument to be easily maneuvered to whatever position may be required by a particular procedure. As discussed above, an additional aspect with respect to stabilizing the beating heart is to eliminate or minimize the flex or motion attributable to the various components and connections of instrument mount assembly 20. As will be discussed in more detail below, instrument mount assembly 20 is uniquely suited for use in stabilizing the beating heart because it allows sufficient degrees of freedom to easily manipulate the position of an instrument secured thereto, allows the degrees of freedom to be frozen or locked in place and, once locked in place, does not significantly flex or allow movement at any of the mechanical joints or connections.

Instrument mount assembly 20 provides a number of different controllable joints that, when in a released condition, allows motion in one or more predetermined directions or about one or more degrees of freedom. Although instrument mount assembly 20 may be used to secure any mounting shaft configuration from straight or curved substantially rigid shafts to multi-link or segmented ball and socket type shafts which are relatively flexible until themselves locked in some manner at each joint along the shaft length, it is most advantageously constructed to provide the joints or connections required to position an instrument having a straight or curved rigid shaft.

In a preferred embodiment, instrument mount assembly 20 has three releasable joints or connections for controlling the location and position of the instrument mount assembly and instrument attached thereto. The mount base may be positioned at a desired location along an appropriate rail and secured by rail grips 114 and 116. The position and orientation of the instrument is then determined by ball joint (or ball and socket joint) 112 between mount base 125 and mount body 110, a rotational joint 157 between mount body 110 and shaft hub assembly 160, and a shaft clamping mechanism within shaft hub assembly 160 which may allow translation, rotation, or both of shaft 3 relative to shaft hub assembly 160.

Ball joint 112 is preferably of the ball and socket type having 3 rotational degrees of freedom. Rotational joint 157 allows rotation of shaft hub assembly 160 about axis 121 as indicated by arrow 113. The shaft clamping mechanism allows translation of instrument shaft 3 as indicated by arrows 111 as well as rotation about the shaft itself as indicated by arrow 117. As will be discussed later, a further ball-joint type connection 201 may be employed between shaft 3 and the particular end-effector of the instrument.

Instrument mount assembly 20, having the particular joints and connections identified above, allows all the required areas of the heart to be conveniently and intuitively accessed by a stabilizer connected to one end of a substantially rigid shaft. certainly, instrument mount assembly 20 could be provided with more or less degrees of freedom for maneuvering a particular instrument. For example, to add additional degrees of freedom rotational joint 157 could be replaced with a ball joint and to eliminate degrees of freedom shaft 3 could be keyed within shaft hub assembly 160 or ball joint 112 could be replaced with a rotation only joint. However, it should be noted that excessive degrees of freedom may tend to make instrument adjustment increasingly difficult and cumbersome to control while too few degrees of freedom may not allow the instrument to be easily placed in the desired position or orientation.

In one embodiment, the various joints and connections are locked into a desired position by way of a series of knobs. The degrees freedom provided by ball joint 112 is locked by activation of top mount knob 120. Both rotational joint 157 and the shaft clamping mechanism of shaft hub assembly 160 is locked in place by the activation of side mount knob 118. Base 125 is locked in position on the rail by activation of mount lever 122. Ball joint 201, as will be discussed in greater detail below, may be locked in position by activation of knob 504. This particular sequence of knobs used to lock down the degrees of freedom associated with instrument mount assembly 20 tends to allow the user greater precision in positioning the instrument because degrees of freedom unnecessary to a particular desired maneuver of the instrument can be locked down. Most commonly, mount body 110 is placed at a desired angle or orientation and then fixed in place by locking ball joint 112, leaving final adjustment to take place using rotational joint 157 and the shaft movement allowed by the shaft clamping mechanism of shaft hub assembly 160.

Figure 14:
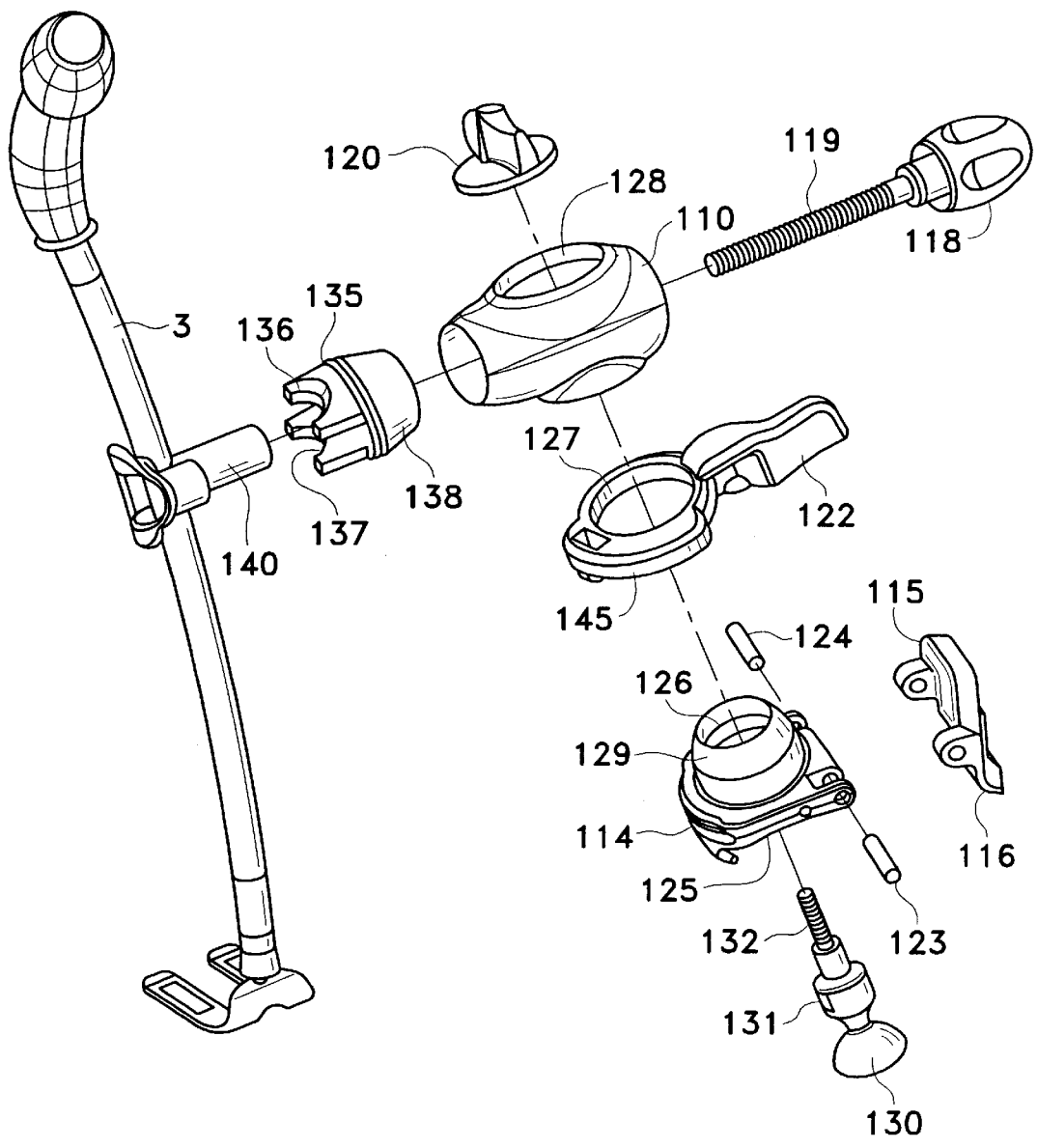
FIG. 14 is an exploded assembly illustration of the instrument mount assembly of FIG. 13.

FIGS. 14–20 show in greater detail the various mechanisms which lock and release the joints or connections associated with instrument mount assembly 20. FIG. 14 shows an exploded assembly illustration of instrument mount assembly 20. Instrument mount assembly 20, and more specifically mount base 125 to which all the other components are ultimately secured, is preferably constructed to engage and lock in position on a rail or other suitable feature.

Preferably, instrument mount assembly 20 has a fixed rail grip 114 adapted to engage mounting tab 64 of rail 60 and a moveable rail grip 116 adapted to engage mounting tab 63 or rail 60. Rail grips 114 and 116 may generally have hook-like features for gripping mounting tabs 63 and 64.

Rail grip 114 is part of mount base 125 and moveable rail grip 116 is part of articulating hinge member 115, which is pivotally attached to mount base 125 by way of hinge pins 123 and 124, or other suitable fastener. Articulation of hinge member 115 and rail grip 116 in clamping manner towards rail grip 114 on mount base 125 effectively clamps mount base 125 onto rail 60 at mounting tabs 63 and 64.

Hinge member 115 may be articulated using any suitable mechanism capable of pivoting hinge member 115 to a closed position and holding it there. In a preferred embodiment, best illustrated in FIGS. 15A-17, hinge member 115 includes follower surface 155 which may be acted upon by any suitable cam device to drive hinge member 115 about hinge pins 123 and 124, thus urging rail grip 116 towards rail grip 114.

In a preferred embodiment, hinge member 115 is articulated by action of cam 145 having cam surface 152 which acts upon follower surface 155. Cam 145 has a center, C about which cam 145 rotates. Preferably, cam 145 has bore 127, having its central axis coincident with center, C. Mount base 125 may have a cam guide 153 around which bore 127 rides for smooth rotation of cam 45 about center, C. Cam surface 152 has a varying radius, illustrated by exemplar radial lines $R_1$, $R_2$, $R_3$, $R_4$, and $R_5$. Thus as cam surface 152 is rotated past follower surface 155, from example from R1 to R2, it pushes the follower surface a greater distance away from center, C, thus causing hinge member 115 to pivot about hinge pins 123 and 124, thus causing rail grip 116 to move closer to rail grip 114.

The varying radius of cam surface 152 may be configured to place hinge member 115, and thus rail grip 116 in a variety of positions. A first portion of cam surface 152 may be configured such that follower surface 155 biased against cam surface 152 is placed in an position characterized in that rail grip 116 is sufficiently spaced apart relative to rail grip 114 to allow assembly onto a rail or other structure. A second portion of cam surface 152 has an increasing radius such that rotation of cam 145 moves rail grip 116 towards rail grip 114 to an intermediate position. In the intermediate position, rail grip 116 has been moved close enough to rail grip 114 so that it becomes captured on a rail but remains loose enough to slide along the rail. A third portion of cam surface 152 has an increasing radius such that the rotation of cam 145 moves rail grip 116 further towards rail grip 114 to a completely locked position wherein relative motion between rail grips 114, 116 and the rail is essentially no longer possible.

Cam 145 is generally provided with a handle or lever 122 to allow the user to easily turn cam 145 relative to mount base 125. Cam 145 may be captured onto mount base 125 by operation of retaining hook 150 on cam 145 which rides within exterior groove 151 on mount base 125 on one side, and projection 154 which is engaged below undercut 156 generally opposite to retaining hook 150. Projection 154 also serves to work against undercut 156 to return hinge member 115 to the open position as cam 145 is rotated in the opposite (open) direction. Hinge member 115 preferably has first and second end stops 158 and 159 between which the motion of projection 154 (and thus the rotation of cam 145) is limited. Cam 145 may also have a protective extended portion or cover 163 which shields the area of groove 151 when assembled over mount base 125.

Figure 15A:
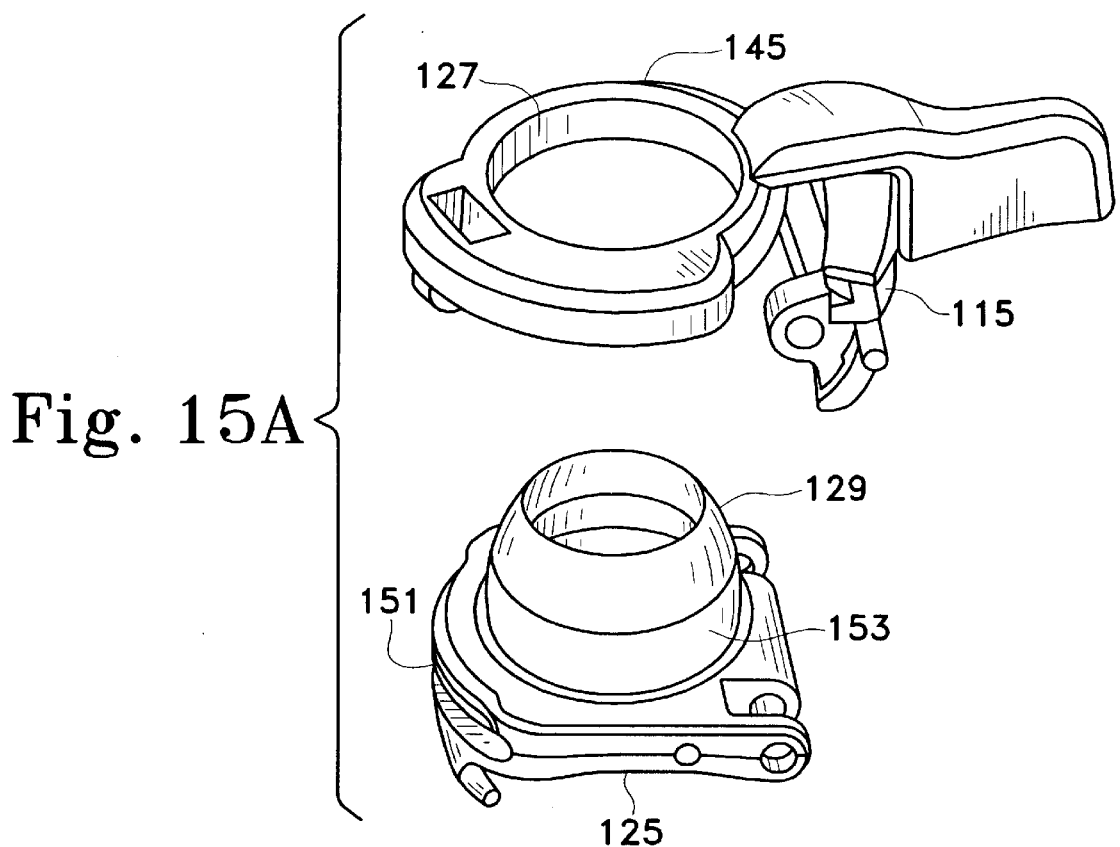
FIGS. 15A and 15B are perspective views illustrating the assembly of the mount cam to the mount base.
Figure 15B:
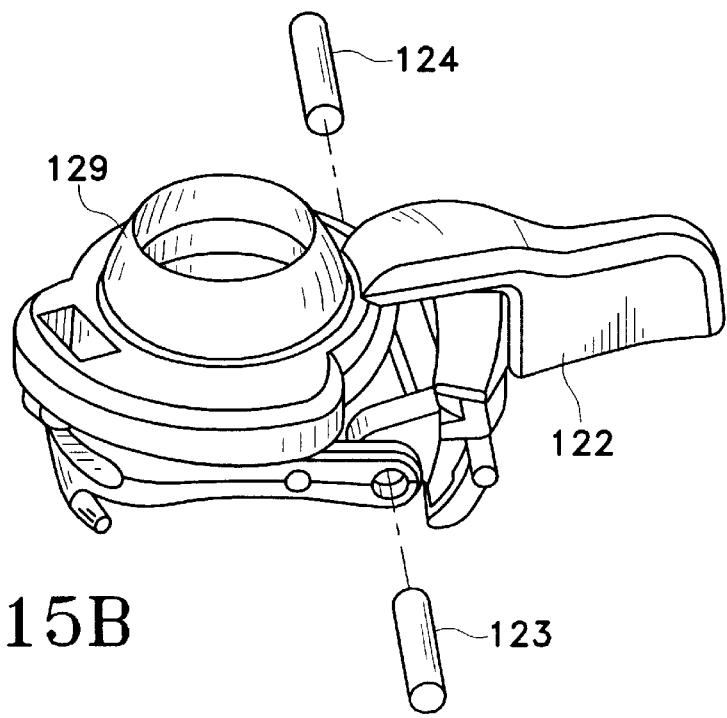
Figure 16A:
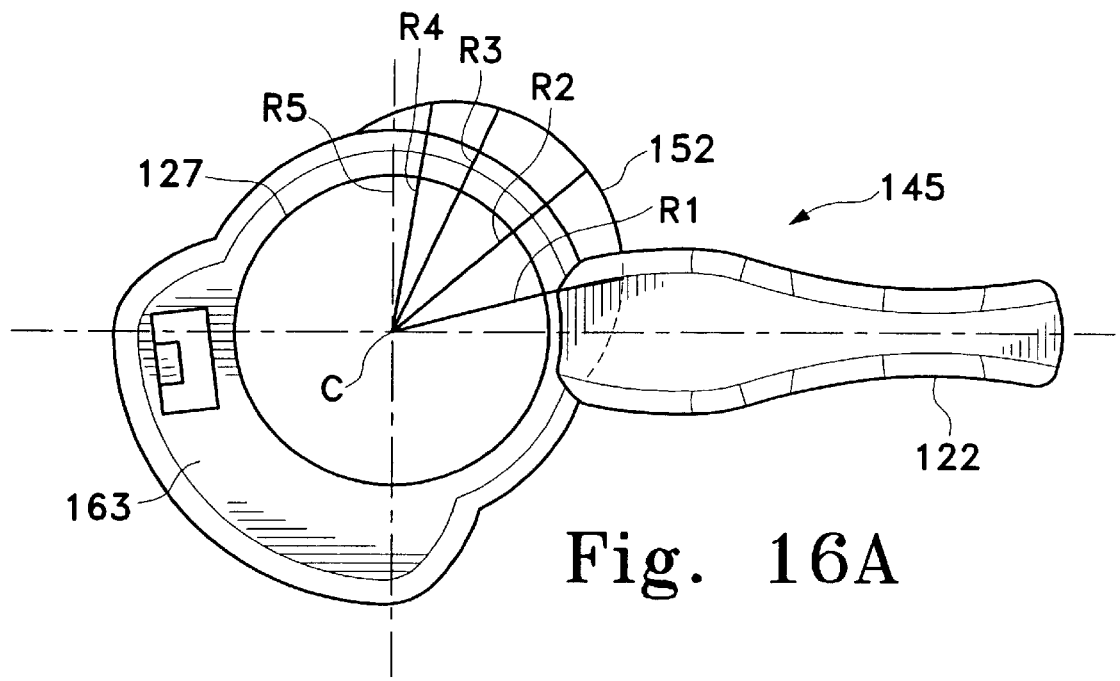
FIGS. 16A and 16B are top and front plan views, respectively, illustrating a preferred mount cam.
Figure 16B:
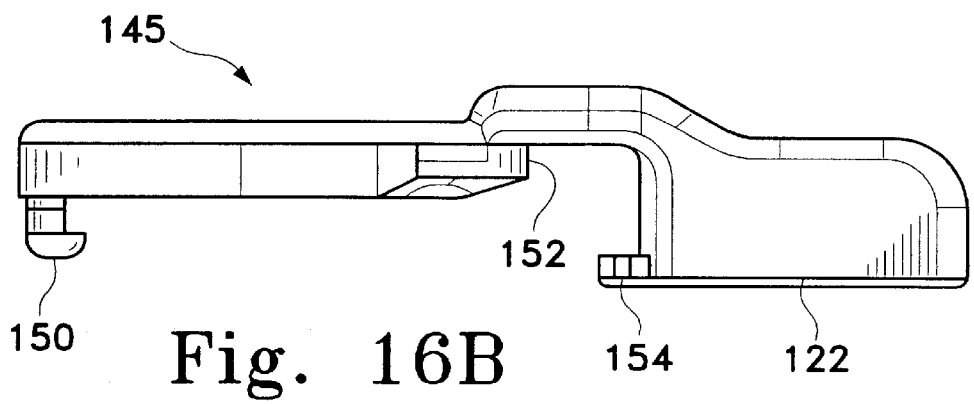
Figure 17:
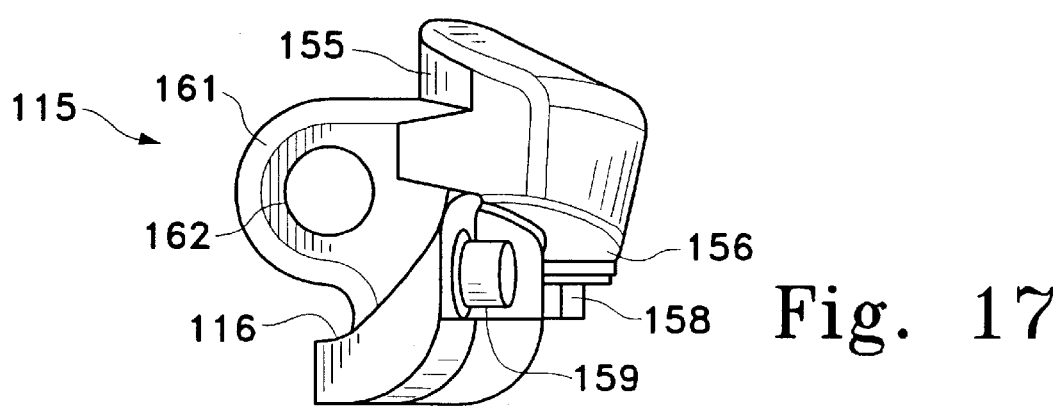
FIG. 17 is a front plan view illustrating a preferred mount hinge.
Figure 18:
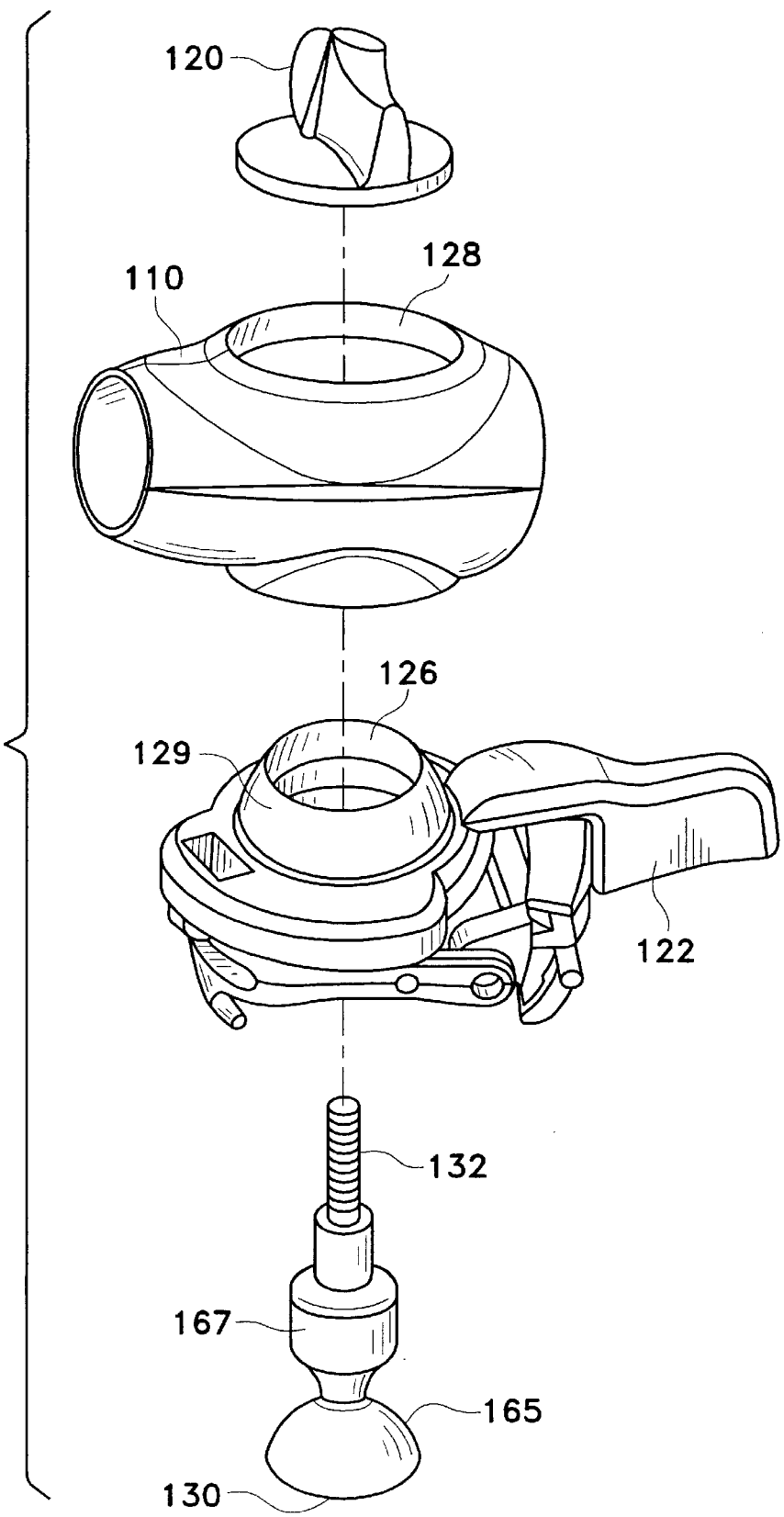
FIG. 18 is an exploded view illustrating the assembly of the mount body to the mount base.

The assembly of cam 145 and hinge member 115 to mount base 125 is illustrated in FIGS. 15A and 15B. Cam 145 is placed in position relative to hinge member 115 with projection 154 in place below undercut 156. In roughly that position, cam 145 and hinge member 115 are brought over mount base 125 until bore 127 is properly seated over cam guide 153 and retaining hook 150 is positioned within groove 151. Pins 123 and 124 are then pressed in place through holes provided in both mount base 125 and hinge member 115.

Ball joint 112 is generally created between ball 129 provided at the top of mount base 125 and a socket or mating cavity within mount body 110 adapted to receive at least a portion of ball 129. Preferably ball 129 includes a generally spherical portion, although other curved shapes providing the desired degrees of freedom may also be suitable. Base post 130 extends vertically upward through bore 126 of mount base 125 and vertical passageway 128 of mount body 110 until enlarged end portion 130 become biased against mount base 125. Top mount knob 120 may then be threaded onto threaded shaft 132 whereby mount base 125 and mount body 110, with ball 129 received within mount base 125, becomes captured between top mount knob 120 and enlarged end portion 130. Continued tightening of top mount knob 120 over threaded shaft 132 forces ball 129 harder against mount body 110 until the friction between mating surfaces on ball 129 and mount body 110 become so great as to effectively resist any relative movement, thus locking ball joint 112.

Figure 19:
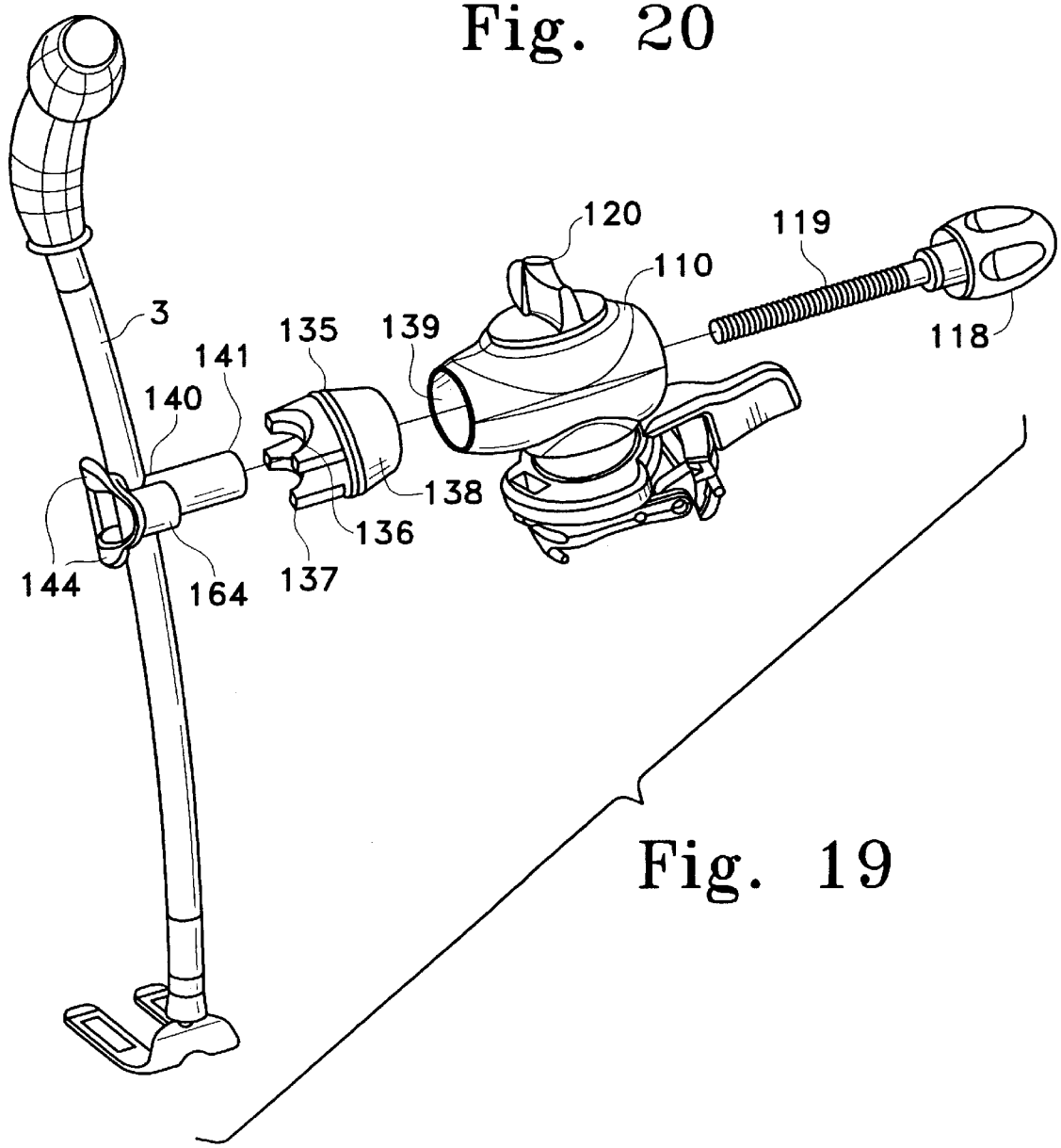
FIG. 19 is an exploded view illustrating the assembly of the instrument clamp to the mount body.

The assembly of rotational joint 157 and shaft hub assembly 160 are shown in FIG. 19. Rotational joint 157 is in the form of a conical clutch formed between frustoconical surface 138 of clutch member 135 and mating frustoconical surface 139 in mount body 110. Shaft hub assembly 160 is generally formed as upper and lower shaft locks 136 and 137 are advanced over shaft grip 140 and against instrument shaft 3 which is positioned between shaft locks 136 and 137 and outer shaft guide 144. As clutch member 135 is received over the outside diameter of grip housing 141 of shaft grip 140 tang 164 becomes engaged between upper shaft lock 136 and lower shaft lock 137 thereby preventing relative rotation between clutch member 135 and shaft grip 140.

Side mount knob 118 having threaded shaft 119 extends through mount body 110 (and consequently through transverse bore 131 in central portion 167 of base post 130), clutch member 135 and into interior threads 142 within grip housing 141 of shaft grip 140. Tightening of side mount knob 118 clamps the assembly together. Thus, translation and rotation of instrument shaft 3 is prevented as shaft grip 140 and clutch member 135 are forced together to clamp or trap instrument shaft 3 between shaft locks 136 and 137 and outer shaft guide 144. Also, relative rotation between frustoconical surface 138 of clutch member 135 and mating frustoconical surface 139 in mount body 110 is prevented as clutch member 135 is forced against mount body 110. One or both of frustoconical surface 138 and mating frustoconical surface 139 may include a number of teeth, ridges, or other features to prevent rotation when clutch member 135 is forced against mount body 110.

Figure 20:
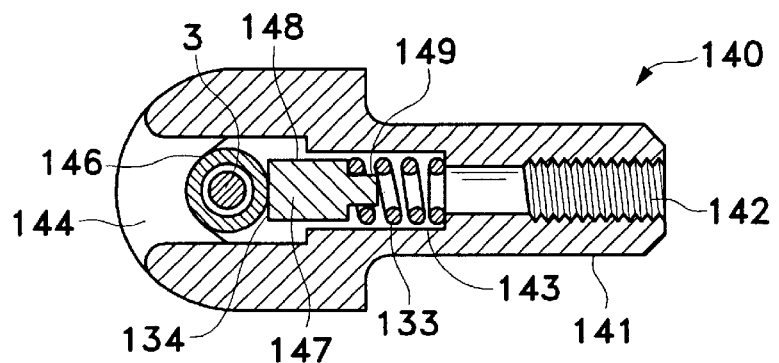
FIG. 20 is a cross-sectional view taken through a horizontal plane of the instrument shaft grip of FIG. 19.

So that the shaft does not become too loose as side mount knob 118 is loosened, a minimum amount of friction between instrument shaft 3 and the clamping surfaces 146 of outer shaft guide 144 is preferably maintained by providing a biasing load against shaft 3. Referring to FIG. 20, shaft biasing member 147 is provided within shaft grip 140 to maintains a biasing load against shaft 3. Shaft biasing member 147 has a first portion 148 which slides within counterbore 143 in shaft grip 140. Shaft biasing member 147 may optionally have a second portion 149 having external dimensions sized to be received within the inside diameter of compression spring 133. Compression spring 133 urges end 134 of shaft biasing member 147 against shaft 3 to force shaft 3 against clamping surfaces 146. The amount of force is selected to allow instrument shaft 3 to be easily positioned by hand but would generally not allow instrument shaft 3 to slide relative to shaft grip 140 under only its own weight.

Figure 21:
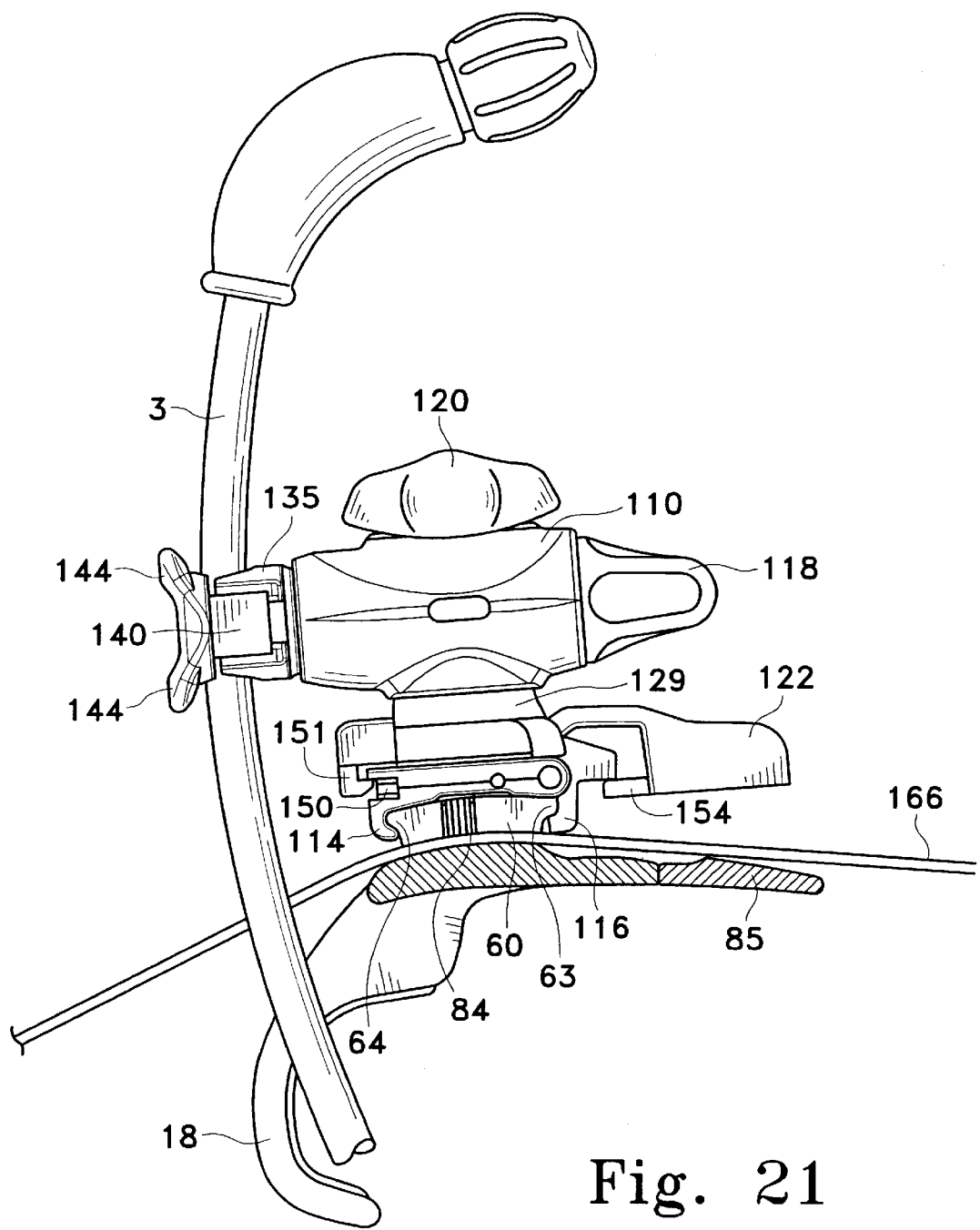
FIG. 21 is a front plan view showing an assembled instrument mount operably positioned on a platform blade according to the principles of the present invention.
Figure 22A:
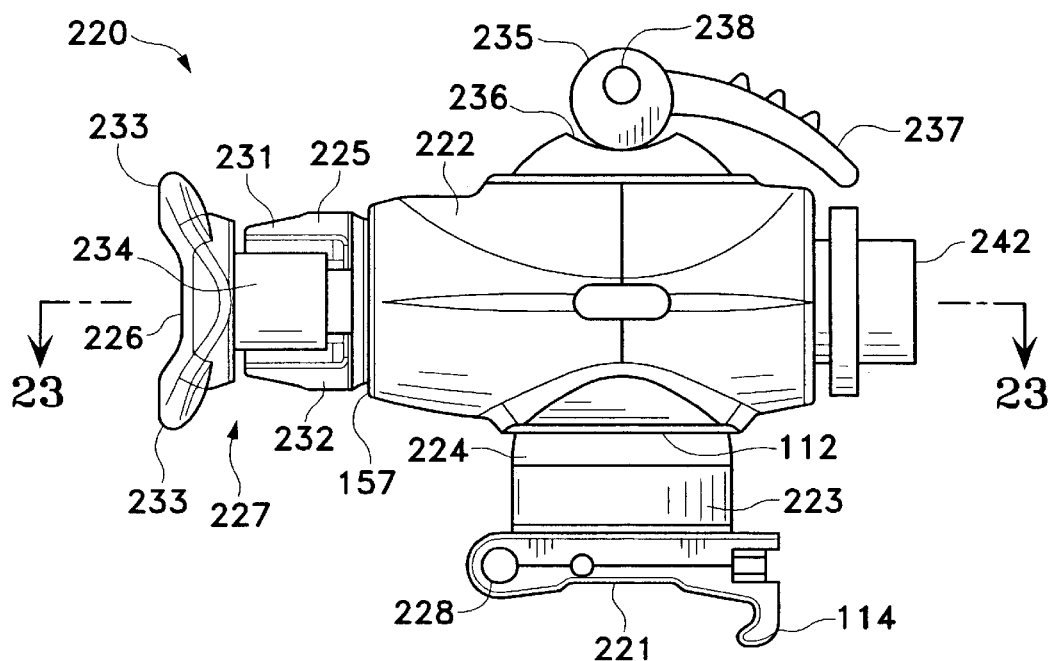
FIGS. 22A and 22B are front and top plan views, respectively, of an alternate instrument mount assembly according to the principles of the present invention.
Figure 22B:
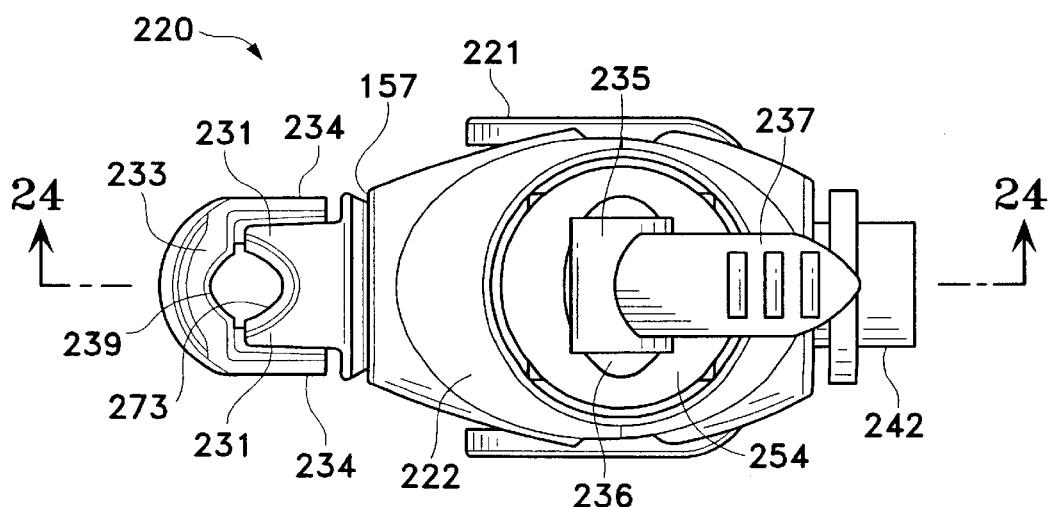
Figure 23:
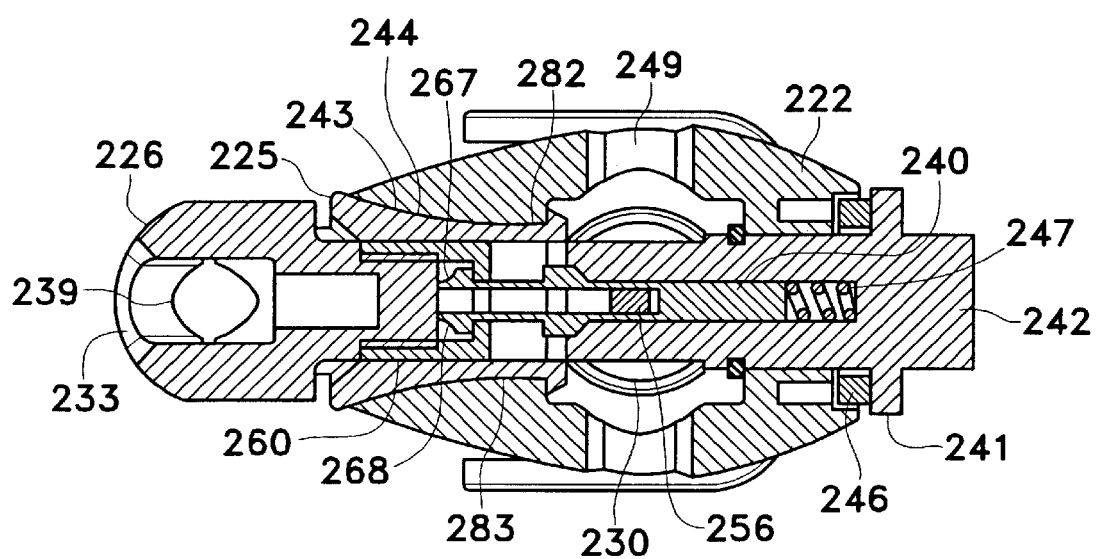
FIG. 23 is a cross-sectional view taken along line 23—23 as shown in FIG. 21.

Referring to FIG. 21 a preferred instrument mount assembly 20 is shown fixed to a preferred platform blade 16 having rail 60. As discussed above, rail 60 has mounting tabs 63 and 64 over which rail grips 114 and 116 may be secured. Instrument mount assembly 20 can be positioned, maneuvered, and removed virtually anywhere along rail 60 without disturbing suture 166 locked in place by free end 84 of suture lock 80 below the operating features of instrument mount assembly 20 within any one of the suture channels provided in platform blade 16. In addition, rail 60 is placed in close proximity to engaging member 18 and thus close to the surgical opening into the patient providing a more direct access to the heart by an instrument mounted to instrument mount assembly 20. Since the rail 60 moves in unison with platform blade 16, this relationship between rail 60 and engaging member 18 is maintained no matter how much or how little platform blades 14 and 16 have been spread to create the desired surgical opening.

FIGS. 22A–32 illustrate a preferred embodiment of an alternative instrument mount assembly 220. Preferably, the degrees of freedom available for maneuvering instrument mount 220 is substantially the same as that of instrument mount assembly 20. Instrument mount assembly 220 preferably has ball joint 112 between mount base 221 and mount body 222, a rotational joint 157 between mount body 222, and a shaft hub assembly 227 which allows rotation and translation of an instrument shaft held between shaft grip 226 and clutch member 226 of shaft hub assembly 227. Instrument mount assembly 220, however, has a different mechanism for controlling or locking the various joints and connections and may also provide a means for releasing and removing the shaft from the bulk of the remainder of instrument mount assembly 220.

As just mentioned, the joints and connections themselves are quite similar between instrument mount assemblies 20 and 220. As before, ball joint 112 is a ball and socket configuration created between generally spherical ball 224 provided at the top of mount base 221 and a mating cavity within mount body 222 adapted to receive and slide against at least a portion of ball 224. Rotational joint 157 may be in the form of a conical clutch formed between frustoconical surface 243 of clutch member 225 and mating frustoconical surface 244 in mount body 222. An instrument shaft may be clamped in place within shaft hub assembly 227 by forcing together shaft grip 226 and clutch member 225 thus closing clamp surface 239 of outer shaft guide 233 towards V-shaped channels 273 on shaft locks 231 and 232.

Instead of locking the joints and connections by way of multiple knobs as described above with respect to instrument mount assembly 20, instrument mount assembly 220 preferably uses a mechanism which releases each of ball joint 112, rotational joint 157, and the shaft clamping mechanism of shaft hub assembly 227 by activation of a single knob, lever, or other suitable manual interface. Generally speaking, this is accomplished by utilizing the clamping motion required to lock one or more of the joints or connections along a first axis to also lock the remainder of the joints or connections along remaining axes.

In a preferred embodiment, ball 224 of mount base 221 is locked in place relative to housing 222 by operation of base post 230. Base post 230 is assembled through mount base 221 and mount body 222 from the bottom until bottom flange 259 (see FIG. 27) is resisted against mount base 221. At the top of base post 230 is upper link portion 256 having pivot hole 257. Cam 235 is attached through pivot hole 257 at off-center link pivot 238 using a pin or other suitable fastener and is supported by contact surface 236 associated with mount body 222. Contact surface 236 may be an integral feature of mount body 222 or may be in a separate mount body cover 254 which may be selected to have superior wear characteristics.

Figure 24:
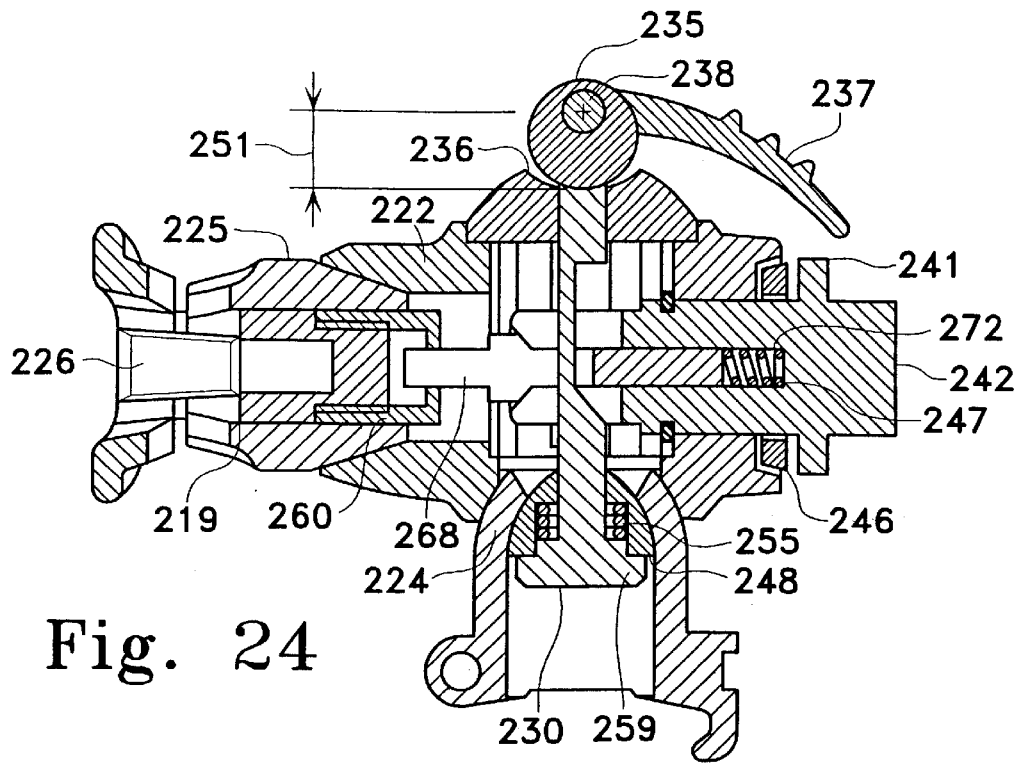
FIG. 24 is an offset cross-sectional view taken along line 24—24 as shown in FIG. 22 illustrating the mount assembly of FIGS. 21 and 22 in the closed position.

With cam 235 in a closed position, as shown in FIG. 24, link pivot 238 is drawn to its maximum distance 251 (or slightly less than the maximum if the cam is constructed to rotate over center) from contact surface 236 thus increasing the clamping force between mount body 222 and ball 224 as the assembly is clamped between cam 235 on the top and bottom flange 259 on the bottom. With cam 235 in the closed position, ball joint 112 is effectively locked.

Figure 25:
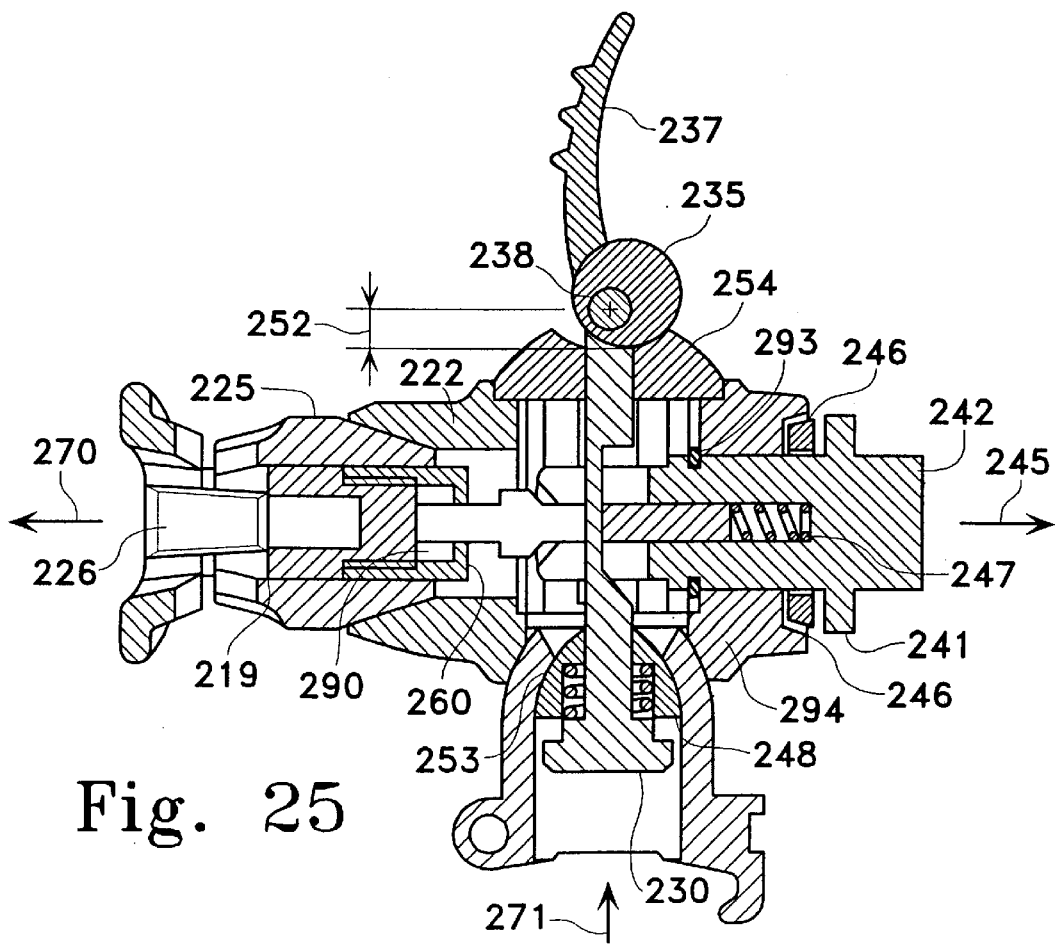
FIG. 25 is an offset cross-sectional view illustrating the mount assembly of FIGS. 21 and 22 in the open position.
Figure 30:
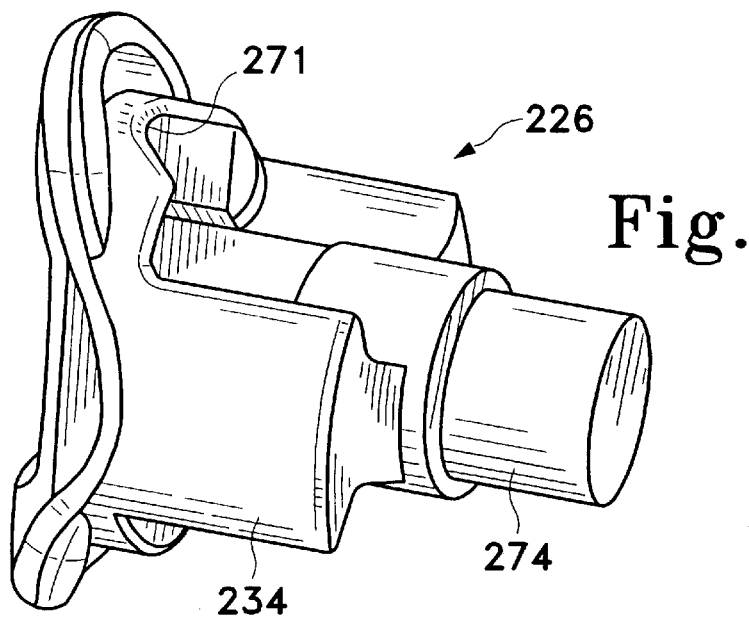
FIG. 30 is a perspective view of a preferred instrument mount shaft clamp.
Figure 32:
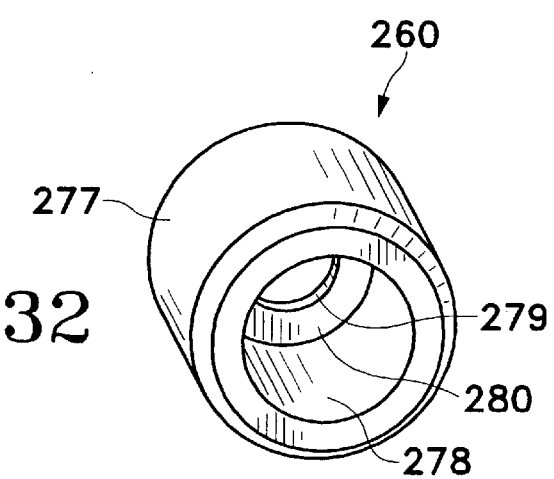
FIG. 32 is a perspective view of a threaded collar associated with the instrument mount shaft clamp.
Figure 31:
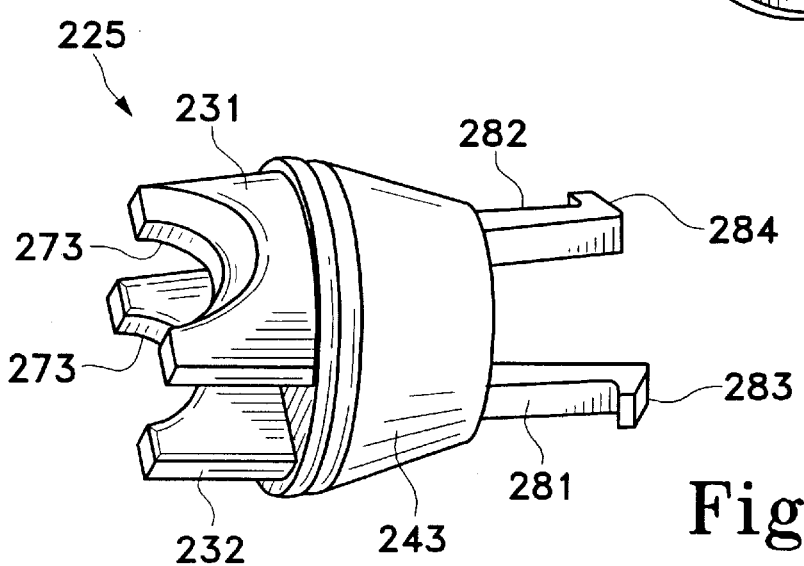
FIG. 31 is a perspective view of a preferred instrument mount conical clutch.

By rotating cam 235, by way of handle 237, to an open position as illustrated in FIG. 25, link pivot 238 is withdrawn to a position closer to contact surface 236 at a distance 252, thus reducing or relaxing the clamping forces between mount body 222 and ball 224 of mount base 221. With cam 235 in the open position, the friction at ball 224 is reduced to a level that allows the user to easily manipulate mount body 222 relative to mount base 221.

Mount base 221 may have an insert 253 secured in the bottom thereof against which bottom flange 259 is caused to seat as upper link portion 256 is drawn upwards by operation of cam 235. Preferably, insert 253 includes recess 255 for receiving compression spring 248 captured about base post 230. Compression spring 248 operates between insert 253, and thus mount base 221, and bottom flange 259 to bias base post 230 towards the unlocked position.

That same motion of base post 230, created by operation of cam 235, is preferably also used to lock both rotational joint 157 and the instrument shaft clamping mechanism of shaft hub assembly 227. Instead of using a threaded shaft to clamp instrument mount assembly along this axis as did the previous embodiment, instrument mount assembly 220 preferably utilizes tie pin 240 which is driven in the direction of arrow 245 causing shaft grip 226 and clutch member 225 to be forced together to clamp an instrument shaft placed therein and also causing frustoconical surface 243 of clutch member 225 to forced against frustoconical surface 244 in mount body 222.

Tie pin 240 preferably has a generally cylindrical back portion 261 and a front portion which is connected in some manner to shaft grip 226. Preferably, the front portion includes forward extending first and second flexible prongs 262 and 263. Cylindrical back portion 261 is slidably received within blind hole 272 of release button 242 and is preferably biased in the unlocked direction indicated by arrow 270 by compression spring 247 positioned within blind hole 272 behind tie pin 240.

Tie pin 240 is preferably driven in the direction of arrow 245 by the movement of base post 230 which is assembled in the space between first and second prongs 262 and 263 of tie pin 240. Preferably, base post 230 has an angled cam or ramp 258 that engages back wall 269 at the base of first and second prongs 262 and 263. As base post 230 is drawn upwards in the direction of arrow 271 by cam 235 from the open position of FIG. 25 to the closed position of FIG. 24, ramp 258 progressively forces back wall 269, and thus tie pin 240, in the direction of indicated by arrow 245.

Tie pin 240, connected at its front end to shaft grip 226, locks an instrument shaft in place and locks rotational joint 157 in the same manner as did threaded shaft 119 of instrument mount assembly 20. In sum, tie pin 240 urges shaft grip 226 towards clutch member 225 and mount body 222. The movement of shaft grip 226, having tang 236 engaged between upper and lower shaft locks 231 and 232 of clutch member 225, closes together in a clamping fashion surfaces 239 on shaft grip 226 and V-shaped channels 273 on clutch member 225. At the same time, shaft grip 226 pushes against clutch member 225 to force frustoconical surface 243 against mating frustoconical surface 244 with sufficient force to frictionally lock the surfaces together, thus preventing relative motion therebetween.

The operation of cam 235 has been described as generally moving between an open position, in which the various joints and connections of instrument mount assembly 220 are free to be easily manipulated about their respective degrees of freedom, and a closed position in which the joints and connections resist any relative movement and are thus effectively locked in position. However, the outer cam profile of cam 235 operating against contact surface 236 may be given a profile that has one or more intermediate positions such that link pivot 238 is placed at an intermediate distance from contact surface 236. In an intermediate position, the joints and connections may be in a stiffened or partially locked state which allows some positional and orientational manipulation with somewhat higher operator forces that the completely released condition. In addition, the action of base post 230 may be such that ball joint 112 becomes fully locked before tie pin 240 has completely locked the remaining degrees of freedom. Thus, cam 235 may have a completely released position where manipulation about all degrees of freedom is easily accomplished, an intermediate position in which only ball joint 112 is fully locked and the remaining degrees of freedom are unlocked or may be partially locked, and final closed position in which all degrees of freedom are locked.

Instrument mount assembly 220 may optionally be provided with a release mechanism allowing shaft grip 226, and thus the instrument shaft slidably assembled therein, to be released from instrument mount assembly 220 preferably by activation of release button 242. This allows instruments associated with instrument mount assembly 220 to be quickly and conveniently removed and replaced or exchanged.

In a preferred embodiment, first and second prongs 262 and 263 of tie pin 240 have first and second projections 267 and 268 which releasably attach tie pin 240 to shaft grip 226. Grip housing 274 of shaft grip 226 is covered with a sleeve having a deep counterbore 278 and small through hole 279. The depth of counterbore 278 is longer than the exterior of grip housing 274 so as to form internal space 290 (see FIG. 25) when assembled. First and second prongs 262 and 263 can be flexed to position projections 267 and 268 relatively close together for insertion through hole 279 where projections 267 and 268 can then expand apart locking projections 267 and 268 behind surface 280.

Preferably, projections 267 and 268 have lead-ins 291 and 292 which urged projections 267 and 268 together as they are advanced through hole 279 so that shaft grip 226 can simply be aligned with lead-ins 292 and 292 and then snapped into place without any further action. Alignment of hole 279 is generally quite simply accomplished as the cylindrical exterior surface 277 of sleeve 260 is slidably received in a substantially coaxial arrangement within center bore 219 of clutch member 225. Clutch member 225 may optionally have first and second flexures 281 and 282 having first and second retaining features 283 and 284 so that it may be snapped in place and thereafter retained within mount body 222.

As mentioned above, shaft grip 226 may be released from tie pin 240. To separate tie pin 240, it is necessary to flex first and second prongs 262 and 263 together so that projections 267 and 268 will again be positioned to fit through hole 280. This may be accomplished by providing a raised portion 264 having a ramp 266 on tie pin 240. A sliding member may be advanced up tie pin 240 and over ramp 266 and raised portion 264 thus flexing prongs 262 and 263 inwards. Preferably, the sliding member is a tip portion 289 of release button 242. Tie pin 240 is slidably received within blind hole 272 of release button 242. The internal diameter of blind hole 272 is small enough so that when it is advanced over ramp 266 and/or raised portion 264, prongs 262 and 263 are flexed inwards. Preferably, the entrance to blind hole 272 has an internal chamfer 288 so that ramp 266 is smoothly engaged as release button 242 is advanced.

Release button 242 preferably has a generally cylindrical body 285 which is slidably received within mating bore 294 (see FIG. 25) of mount body 222. Release button 242 is retained in place, and its sliding travel limited, by release button flange 241 on one end and spring clip or e-clip 293 assembled within e-clip groove 286 on the other end. Spring material 246, such as a wave spring washer or foam material, may be disposed between release button flange 241 and mount body 222 to bias release button 242 outwards. Transverse to blind hole 272 tip portion 289 also has a clearance slot 287 through which base post 230 passes.

For clarity only, FIGS. 22A–25 have illustrated instrument mount assembly 220 without hinge member 115 and cam 145 attached. However, hinge member 115 having rail grip 116 is preferably pivotally mounted, with cam 145 in place, by way of pins or the like at hinge mount 228 as described above with reference to instrument mount assembly 20. As discussed above, cam 145 may be rotated about cam guide 223 using base lever 122 to secure the instrument mount to a rail or other suitable structure.

The retractor and instrument mounts described above can be used to mount and stabilize a great number of instruments for use during surgery. Preferably, the retractor and instrument mounts are used to mount a mechanical stabilizer for stabilizing at least a portion of the beating heart during CABG surgery or the like. Described below are a number of mechanical stabilizer embodiments that are particularly beneficial for stabilizing the beating heart, especially when used in conjunction with the retractors and instrument mounts described above.

Tissue Stabilizers

Once access to the heart is achieved, and the heart is positioned if necessary, a means for stabilizing the beating heart is introduced through the opening created and at least one component of the stabilizing device of the present invention is brought into contact with the beating heart. The surgeon then applies a stabilizing force to the beating heart via the stabilizing means which may then be fixed in place by attachment to a fixed support. When a retractor or platform is fixed in an open position to expose the heart, the retractor platform may also provide the stable support structure to which the stabilizing means is affixed. When the position of the stabilizing means is fixed by attachment to a stable support or to the retractor platform, the stabilizing force is maintained for the duration of the procedure.

The structure of the portion of the stabilizing means which contacts the heart may include one or more contact members which exert a stabilizing force on the heart proximate to the site of the anastomosis. A pair of contact members may be plates or rectangular members which are placed on either side of the target coronary artery at the site of the anastomosis and which may have friction means or tissue spreading or compressing apparatus associated therewith. The contact members may also be provided by a platform which may be substantially planar or which may be contoured to fit conformingly on the surface of the heart. The stabilizing means may also include a shaft means having several alternative embodiments to facilitate adjusting the position and orientation of the instrument. For example, the shaft means may have an adjustable length and the axis of the shaft means may have at least one ball joint disposed within its length such that the orientation of the shaft means relative to another structure such as the contact members or stable support may be continuously varied. As is apparent from the description of the several embodiments, each of the individual embodiments described and illustrated herein has discrete components and features which may be readily separated from or combined with the features of any of the other several embodiments.

Referring to FIGS. 33–37, a preferred stabilizer assembly for stabilizing the beating heart is comprised of a foot or base portion 553 attached to a rigid or semi-rigid shaft means or connecting shaft 3. Base portion 553 typically has one or more contact members 1 adapted to contact the heart adjacent the site desired to be stabilized. The contact members 1 may be substantially planar, may be slightly curved to conform to the shape of the heart, or may be a non-conforming curve to establish contact between only a portion of the contact member 1 and the beating heart. The shape of the contact members may be varied depending on the clinical assessment by the surgeon, the design of the other features of the stabilizing means, or the design of other instruments used to complete the anastomosis. In some embodiments the contact members 1 may have apertures, openings or attachments to facilitate connection with sutures or other devices to achieve the requisite stabilization, occlusion of the target vessel, or exposure of the target vessel. Examples of suitable base portions and contact members can be found, for example, in co-pending U.S. patent application Ser. No. 08/931,158 filed on Sep. 16, 1997, entitled "SURGICAL INSTRUMENTS AND PROCEDURES FOR STABILIZING THE BEATING HEART DURING CORONARY ARTERY BYPASS GRAFT SURGERY", the entirety of which is herein incorporated by reference.

Figures 33, 34:
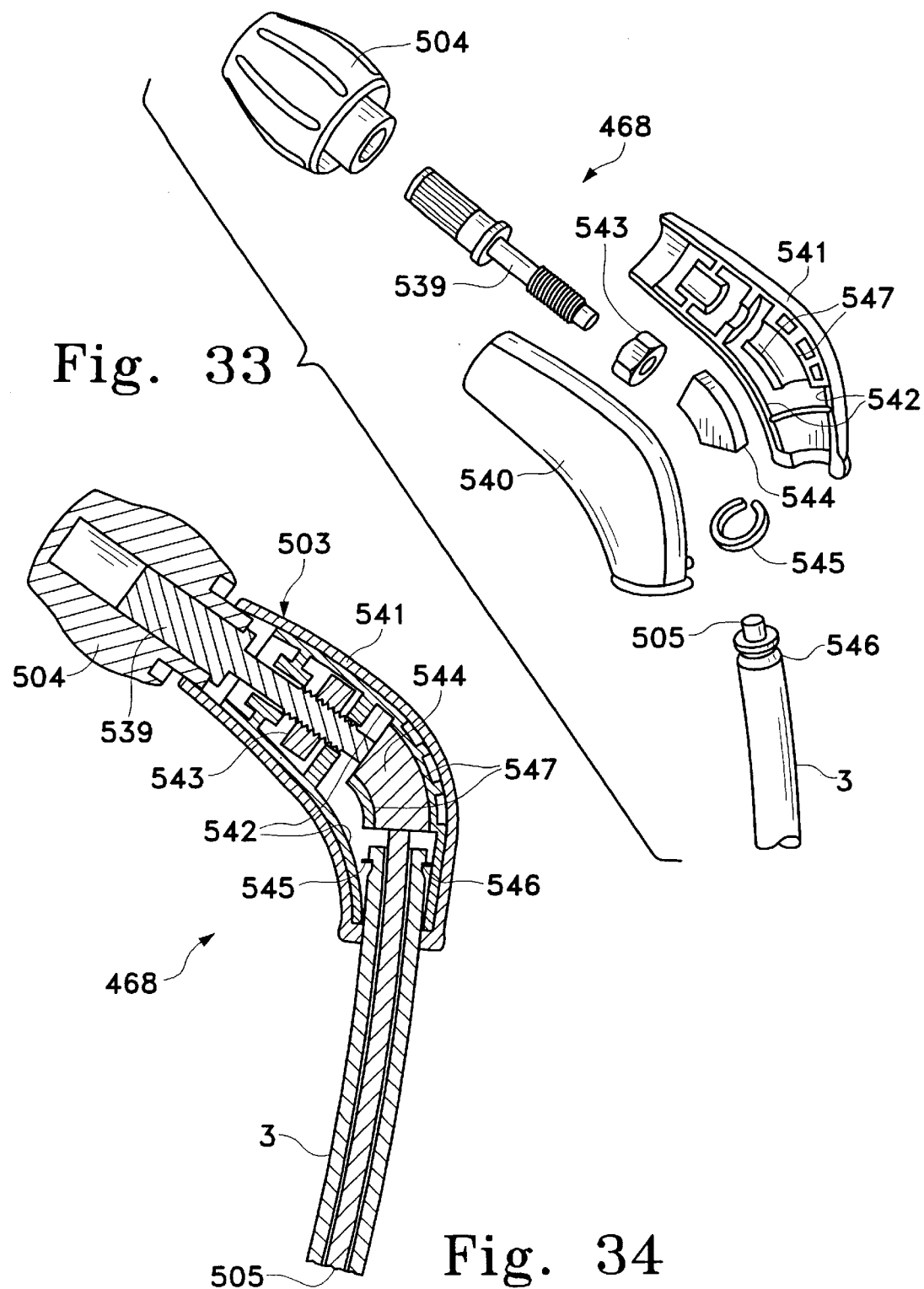
FIGS. 33 and 34 are exploded perspective and cross-sectional views respectively of a handle mechanism of a preferred tissue stabilizer.

Referring to FIGS. 33 and 34, the proximal end of connecting shaft 3 has handle mechanism 468 assembled thereto which, among other things, provided the user with a means for locking an end effector operably attached to the distal end of connecting shaft 3. The mechanism 468 is rotatably secured to the proximal end of the shaft means 3 and is formed at a selected angle to the shaft means to permit a surgeon to swivel the mechanism to a preferred position where the knob 504 is more readily accessible to allow quickly locking the shaft means 3 in the orientation selected. In addition, the angled axis of the knob 504 relative to the shaft means 3 reduces the tendency of the shaft means 3 to rotate about its axis when a surgeon applies torque to the knob 504 to lock the associated locking mechanism. The knob 504 is secured to a screw 539 by suitable means such as press fitting, bonding, etc. Right and left handle covers 540,541 comprise the handle 503 and provide the support for the handle mechanism. When assembled, the covers define generally a cylinder formed with a selected curvature. A secondary inner molding, generally indicated at 542, includes various integrally formed annular walls and shoulders for supporting and containing the knob 504 and screw 539, as well as a cooperating nut 543, and arcuate wedge 544, a shaft retaining ring 545, the proximal end of the shaft means 3, and a proximal end of the translatable pushrod 505. The proximal end of the shaft means 3 includes an annular retaining ring slot 546 which secures the proximal end of the shaft means 3 within suitable annular walls in the corresponding end of the handle covers 540, 541 when the retaining ring 545, confined by shoulders in the inner molding 542, is snapped into the slot 546 and the covers are assembled. The nut 543 is confined by shoulders in the inner molding 542, and the arcuate wedge 544 is slidably confined by correspondingly arcuate walls 547 also formed in the inner molding.

As may be seen, rotation of the threaded screw 539 within the confined threaded nut 543, causes translation of the screw, pivoting and thus translation of the translatable wedge 544 which abuts the screw, and translation of the pushrod 505 which abuts the translatable wedge. As is further described relative to FIGS. 35–37, any tightening or loosening of the screw 539, however slight, will cause a corresponding translation of the pushrod 505 into or out of the shaft means 3.

As depicted in the Figures, the shaft means 3 and thus the pushrod 505, are formed with a slight arcuate configuration, which permits additional degrees of freedom and movement and orientation of the distal end of the shaft means 3 and thus of the heart contact member 1. Rotation of the shaft means 3 about the axis of confinement within the shaft grip 495 or 495a, moves the distal end of the shaft means 3 through a circular path while changing the angles through which the contact member 1 can be oriented. This allows a surgeon to conveniently achieve a wider range of positions and orientations of the contact member relative to the patient's heart, while keeping the proximal end of the shaft means 3 and handle mechanism 468 out of the way as much as possible.

FIGS. 35–37 illustrate an associated mechanism for maneuverably supporting the various embodiments of the contact member 1 and for cooperatively assisting in the quick locking of the contact member by a partial rotation of the knob 504 once the member is positioned. To this end, the distal end of the shaft means 3 is provided with exterior threads matching interior threads in a ball/socket 548. The distal end of ball/socket 548 is provided with slots 549, whereby the remaining material comprises short extended tips 550 which, when bent in or inwardly formed, form a socket. A ball/post 551 includes a ball at one end and a post at the other. When the mechanism is assembled, the ball/post 551 is inserted into place within the ball/socket 548 with the ball in the socket and the post protruding from the ball socket. A mechanism for providing a preloaded source, such as a compression spring 552, is coupled to the ball/socket 548 abutting the ball. The spring 552 is urged by the distal end of the shaft means 3 to exert a preloaded or constant minimum force against the ball of the ball/post 551. The post of the ball/post 551 is solidly fixed as by pressing fitting, welding, etc., to the contact member 1. The distal end of the pushrod 505 passes through the spring 552 to abut the ball of the ball/post 551. Thus when the screw 539 is not tightened, the distal end of the pushrod 505 exerts a slight pressure against the ball, however the spring 552 maintains a preloaded force against the ball sufficient to maintain the contact member 1 at any orientation set by a surgeon. When the screw 539 is tightened, the pushrod 505 is forced against the ball to prevent any further movement of the contact member 1. As may be seen, the contact member 1 can be tilted to assume many orientations since the narrow center of the post can tilt into any of the four slots in the ball/socket 548. In addition, simultaneous rotation of the curved shaft means 3 provides a surgeon with an even greater variety of orientations of the contact member relative to a patient's heart.

The contact member 1 includes a preferred configuration which improves the size of the area of the heart which is visible to a surgeon while still providing the required suppression of heart movement necessary to enable the efficient construction of the anastomosis. More particularly, the pair of spaced-apart contact members 1 extend from a common base portion 553, which uniquely first extends back away from the tips of the contact members at the point of attachment to the post, as shown at reference number 554. The spaced contact members 1 then curve downward away form the common base portion 553 and back past the post and away from the shaft means 3. As may be seen in the FIGS. 35–37, the contact member 1 of this embodiment uniquely is attached to the post on the same surface as the surface that bears against the surface of the beating heart. Since the members 1 separate at the base portion 553 at a point 555 behind the distal end of the shaft means 3, a surgeon has an unobstructed and thus optimum view of the heart even below the distal end of the shaft means 3.

The contact members preferably include friction means 556 selectively secured to the bottom surfaces thereof to more securely engage a beating heart. In addition, the tips of the contact members are bent upward in the form of "ski tips" to lessen their impact when the contact members are firmly pressed against a beating heart to suppress the anastomotic site.

Although screw means 539/504/543 is illustrated herein as a locking mechanism of the handle mechanism 468, it is to be understood that other mechanisms may be employed. For example, a cam/lever mechanism may be attached to a rod which in turn imparts a pivoting movement or translation to a suitable bellcrank or pivotable member, which in turn imparts translation to pushrod 505 of the shaft means 3. Thus, locking mechanisms other than those specifically described herein may be used.

The basic configuration as just described with reference to base portion 553 provides the maneuverability necessary to access and stabilized any desired vessel on the surface of the beating heart. However, the exact manner and position in which the stabilizer may be placed relative to the vessel and the surgical techniques preferred by an individual surgeon may vary significantly. Accordingly, there is some potential that certain combinations of stabilizer positioning may interfere somewhat with the preferred surgical technique of a particular surgeon. The embodiments illustrated below with respect to FIGS. 38–40B alleviate any such problems.

Figure 38:
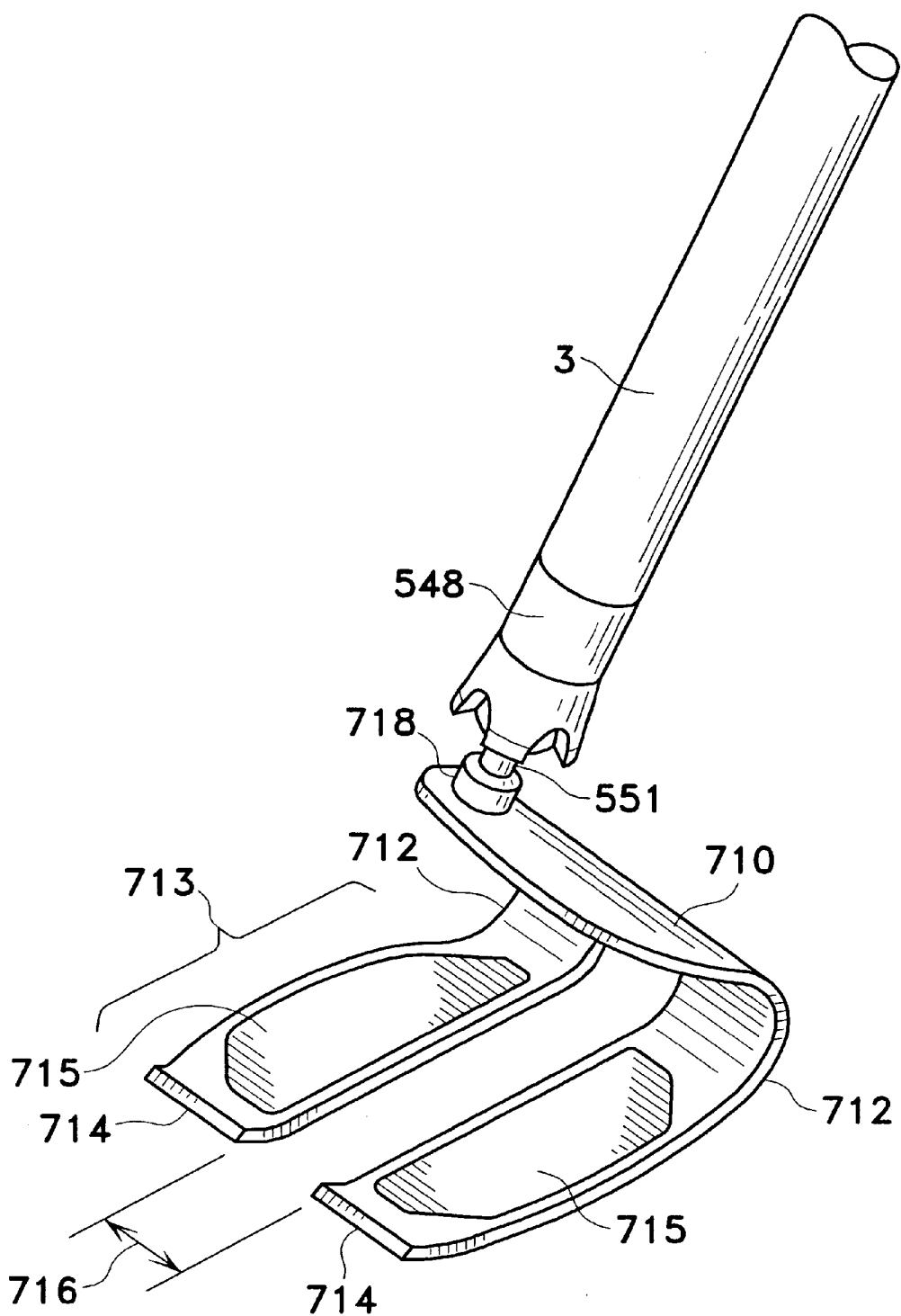
FIG. 38 is a perspective view illustrating a stabilizer base embodiment having an offset shaft connection.

One useful variation, as illustrated in FIG. 38, connects connecting shaft 3 to the base portion of the stabilizer at a position which is generally offset from the center or off-center. Base portion 710 is again typically formed of a unitary piece of sheet material and has a curved back portion in which connecting shaft 3 is attached to an extension of S the same surface which carries the contacting members, except that the connecting point 718, to which ball/post 551 is attached is positioned away from the center and therefore away from the space between contact members 712 where the anastomosis would be performed. This configuration tends to ensure that connecting shaft 3 will not interfere with the surgical access to the center area of the base portion. Of course, the connection can be offset from the central region in either direction.

In addition, base portion 710 illustrates a number of features for improving the traction and vessel presentation during a CABG procedure on a beating heart. Contact members 712 of base member 710 have portions 713 having an increased width and which are preferably substantially flat or slightly curved to conform to the heart. This configuration provides a larger area for coined regions 715, which represent indentations on the bottom surface for receiving a traction material, thus providing greater traction against the surface of the heart.

Further, base portion 710 provides a smaller open space between contact members 712. In a preferred embodiment, the spacing 716 between contact members 712 is less than about 0.350 inches, more preferably less than about 0.300 inches, and most preferably about 0.25 inches. This minimized spacing provides stabilization closer to the vessel and, in some instances, the compressive forces applied through contact members 712 actually tend to present the vessel upwards between contact members 712 in a more favorably pronounced manner. The tip portions 714 of contact members 712 are angled upwards from the surface of the heart to minimize any possible trauma to the heart during use.

As just discussed, the base portions (550 or 710) can be manipulated or oriented relative to the end of the connecting shaft 3 by virtue of the ball and socket joint between base portion 553 and connecting shaft 3. The amount of angular manipulation or travel available is somewhat limited as ball/post 551 eventually bottoms out or stops against either the bottom of slots 549 or extended tips 550. Thus, the contact members have a limited range of movement relative to connecting shaft 3 based upon the nominal mounting relationship between the contact members and the ball/post. Accordingly, for some procedures, it may be desirable to have a different nominal relationship between the contact members and the ball/post to shaft connection.

Figure 39:
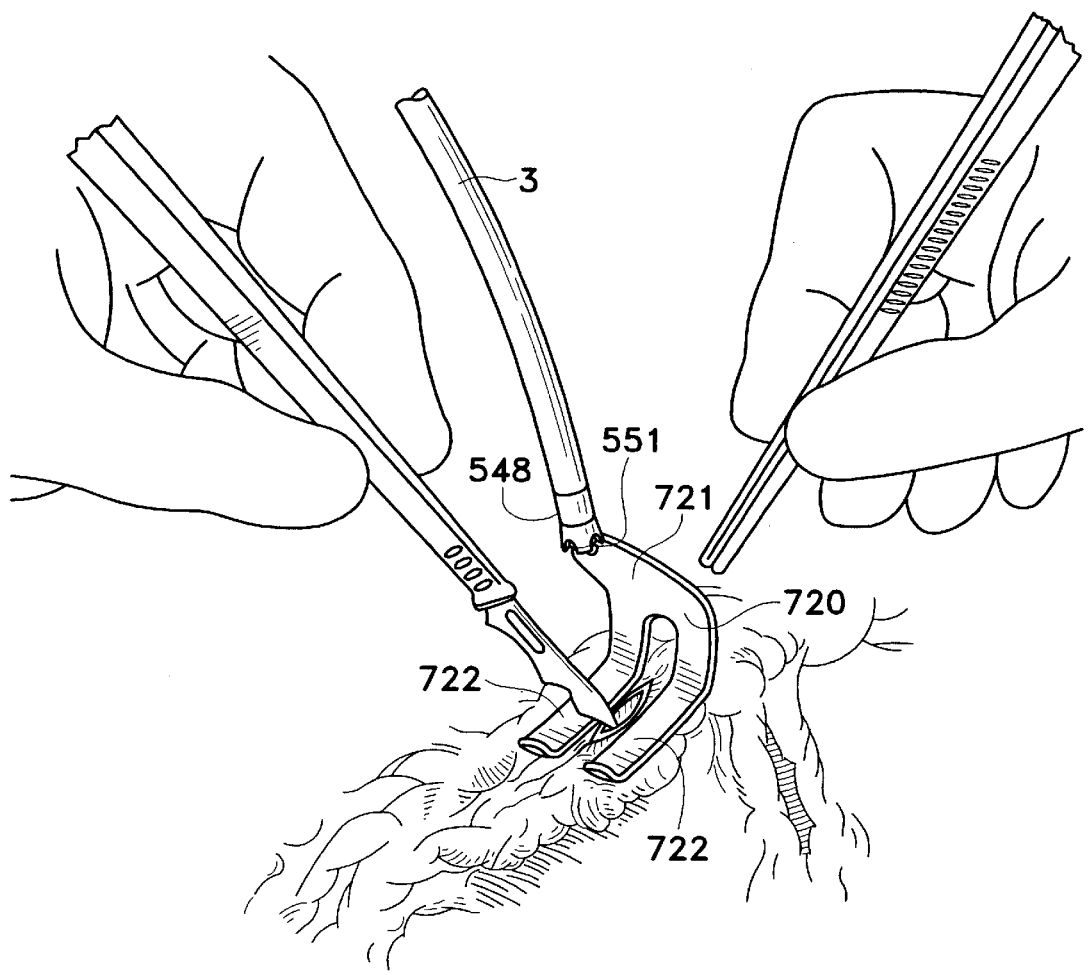
FIG. 39 is a perspective view illustrating an alternative offset stabilizer base in use over a target vessel.
Figure 40A:
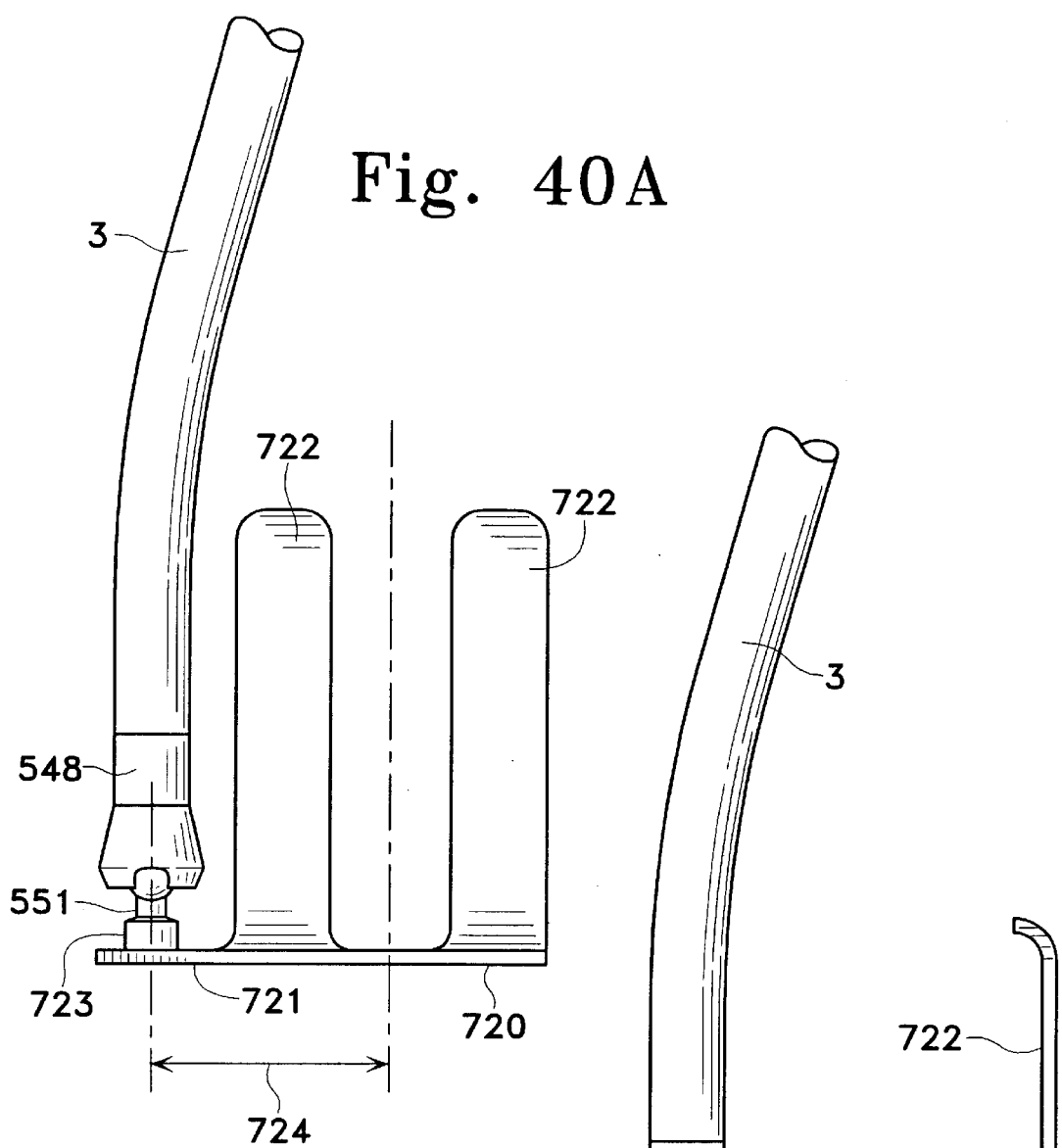
FIGS. 40A and 40B are respectively front and side plan views of the offset stabilizer base embodiment of FIG. 39.
Figure 40B:
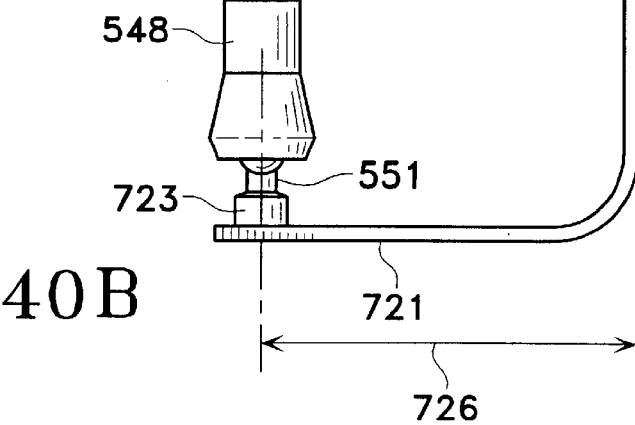
Figure 41:
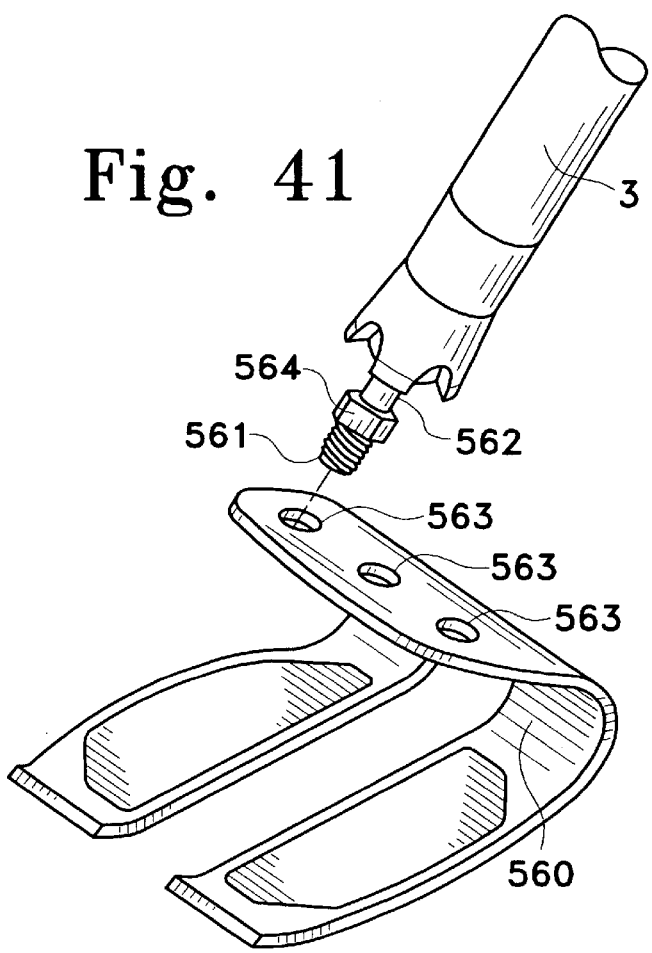
FIG. 41 is a perspective view of a tissue stabilizer having a moveable ball/post.

Referring to FIGS. 39–40B, base member 720 illustrates an alternative orientation of ball/post 551. Instead of being angled away from the contact members, base member 720 has a back portion 721 which allows ball/socket 551 to be mounted generally parallel to contact members 722. Ball/post 551 preferably extend towards contact members 722 as shown, but may also extend the opposite direction away from the contact members. The connecting point 723 is preferably offset a distance 724 from the central area between the contact members 722. The connecting point 723 is also off set a greater distance 726 from the contacting place of contact members 722. In nominal position of base portion 722 relative to ball/post 551, this configuration tends to keep the connecting shaft 3 clear from the central portion between contact members 722. Furthermore, relative to connecting shaft 3, contact members 722 can be maneuvered through a range of motion different from base member 553 due to the initial orientation of ball/post 551.

Because the preferred location of the attachment of the connecting shaft 3 to the base portion may be different from surgeon to surgeon and from procedure to procedure, it may be desirable to have the ball/post moveable to more than one location. In one embodiment shown in FIG. 41, for example, ball/post 562 has threaded end 561 which may be threaded into any desired threaded receiving hole 563 provided in stabilizer base 560. Ball post 564 is preferably provided with one or more flats 564 on the exterior thereof to facilitate tightening or loosening of the threaded connection. In the embodiment shown, stabilizer base 560 has threaded receiving holes 563 to provide center, offset right, and offset left connecting positions.

Figure 42:
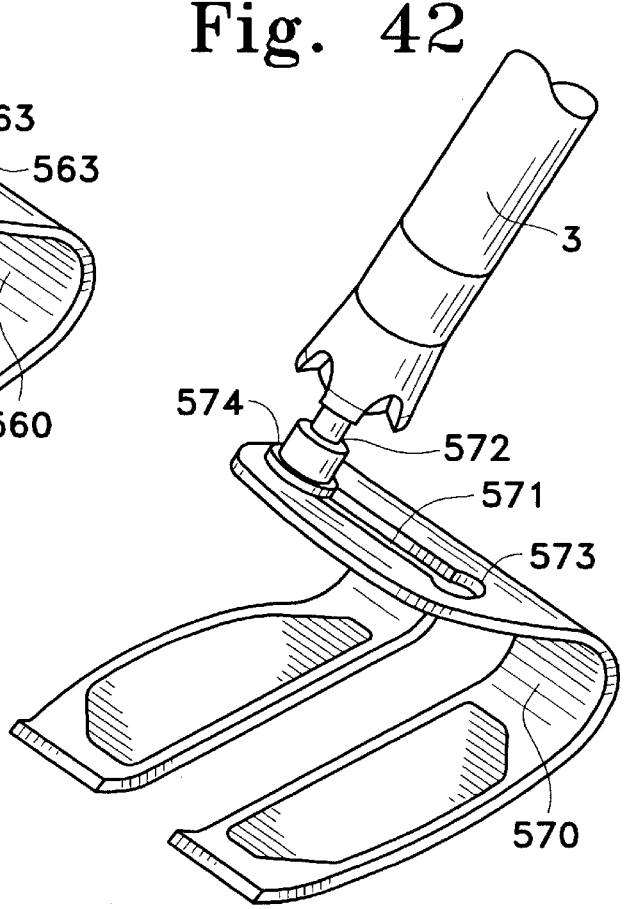
FIG. 42 is a perspective view illustrating another tissue stabilizer embodiment having a moveable ball/post.
Figure 43:
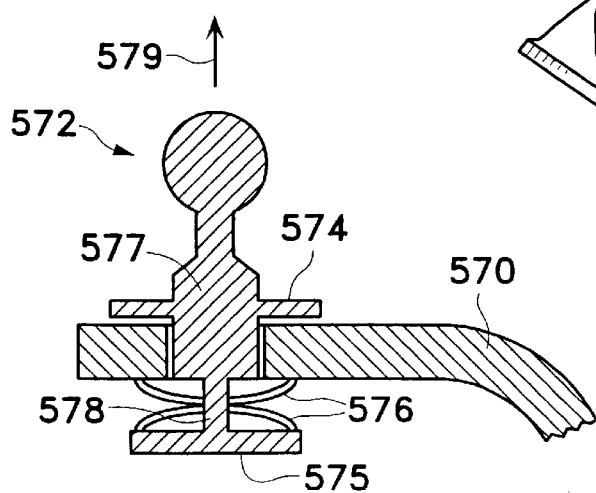
FIG. 43 is a partial cross-section taken through the ball/post of FIG. 42 showing a spring biased ball/post.
Figure 44:
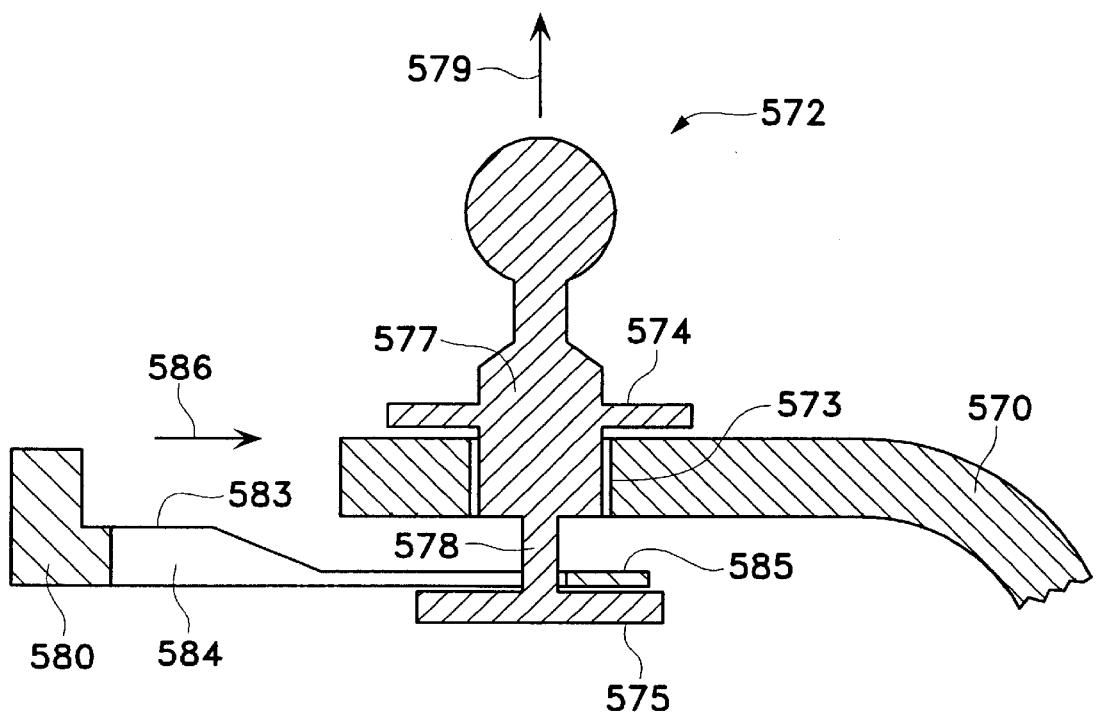
FIG. 44 is a partial cross-section showing the ball/post of FIG. 43 utilizing a locking clip to secure the ball/post.

Referring to FIGS. 42 and 43, ball/post 572 may be captured within slot 571 formed in stabilizer base 570. Slot 571 preferably has two or more positions where the ball/post can be positively locked. In a preferred embodiment, slot 571 preferably has two or more key-hole openings 573. Key openings 573 are sized to receive first post portion 577 having an outside diameter which closely matches the inside dimension of key opening 573. First post portion 577 of ball/post 572 is released from key hole 573 by pulling ball post in the direction indicated by arrow 579 until second post portion 578 is positioned within keyhole 573. Second post portion 578 is sized to have an outside diameter small enough to fit and traverse through slot 571. Ball/post 572 may then be traversed along the path defined by slot 571 until the next desired key hole is reached, which may then be engaged by first post portion 577 to secure ball/post 572 in position on stabilizer base 570.

First post portion 577 may be kept in engagement with keyholes 573 by any convenient manner. For example, ball/post 572 may be spring biased in the locked position between upper flange 574 and lower flange 575, preferably using spring washers 576 as shown. Ball/post 572 may also be locked into operating position within keyholes 573 by using a retaining or locking clip, such as locking clip 580 illustrated with reference to FIGS. 44 and 45. Locking clip 580 has slot 584 adapted to slide over second post portion 578. Locking clip 580 includes a thin portion 585, a thick portion 583, a transition ramp 582 between thin portion 585 and thick portion 583, and a grip or handle portion 581. With locking clip 580 in the open position shown in FIG. 44, ball post 572 is free to move upwards in the direction of arrow 579, thus releasing first post portion 577 from key hole 573. When locking clip 580 is moved in the direction indicated by arrow 586, the outer thickness of thick portion 583 is wedged between lower flange 575 and stabilizer base 570, thus locking ball/post 572 in place within keyhole 573.

Figure 46:
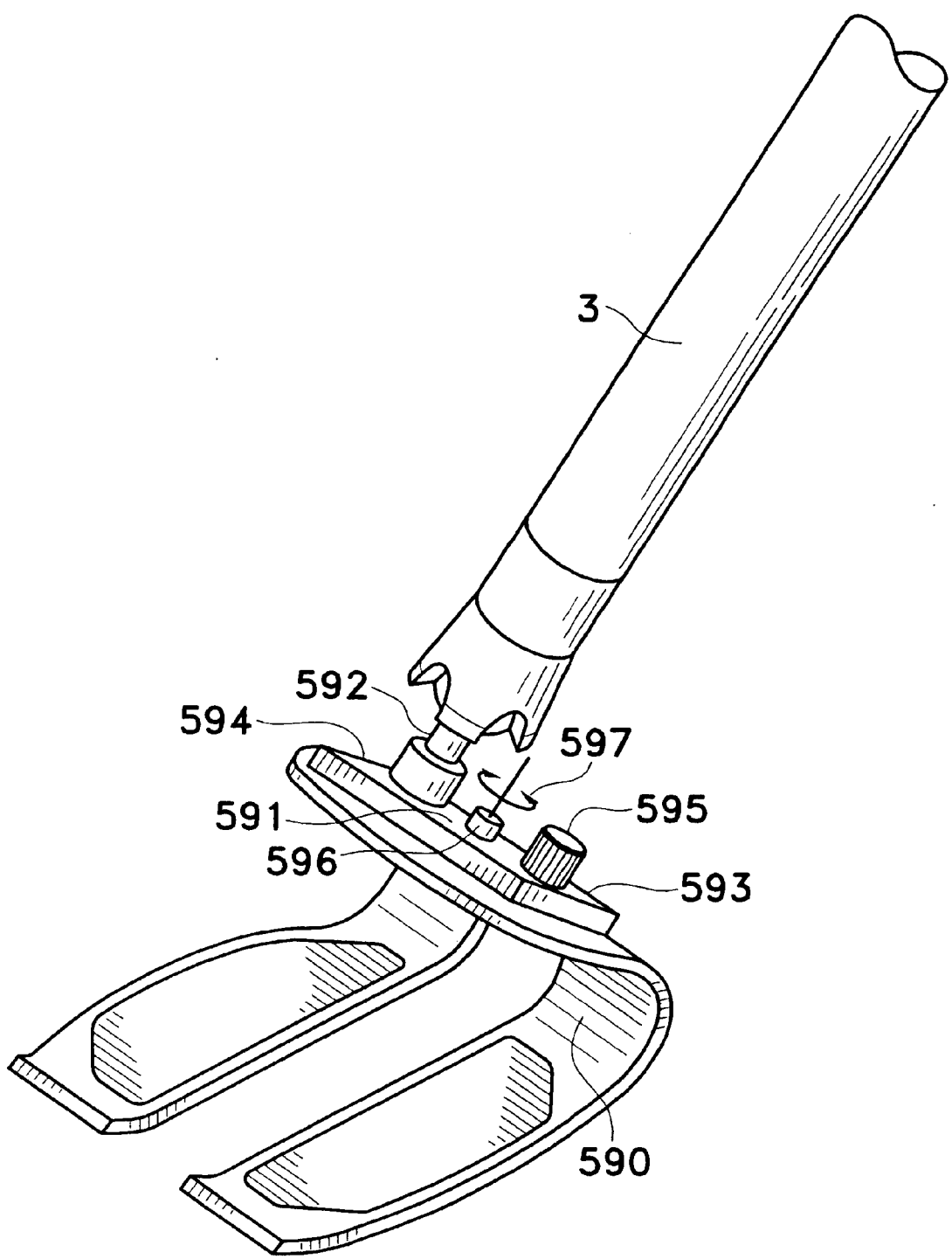
FIG. 46 is a perspective view illustrating another moveable ball/post stabilizer embodiment.
Figure 48:
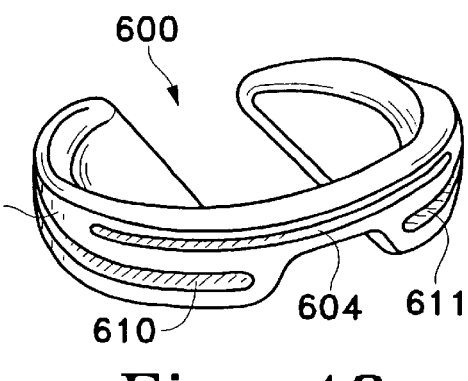
FIG. 48 is a rear perspective view of the stabilizer base of FIG. 47.
Figure 47:
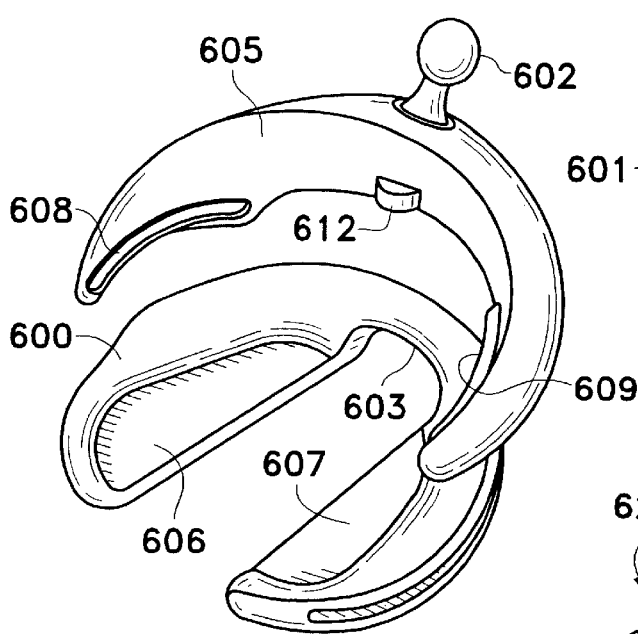
FIG. 47 is a front perspective exploded view of a stabilizer base assembly having an adjustable ball/post position.
Figure 49B:
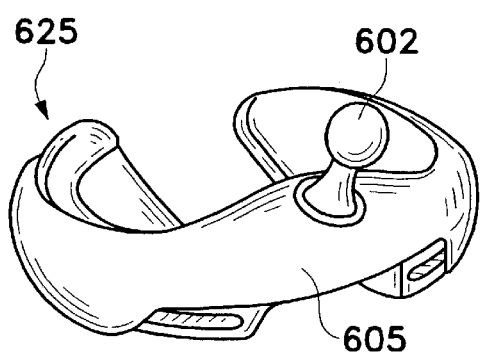
FIGS. 49A and 49B are front and rear perspective views of the stabilizer base assembly of FIG. 47.
Figure 49A:
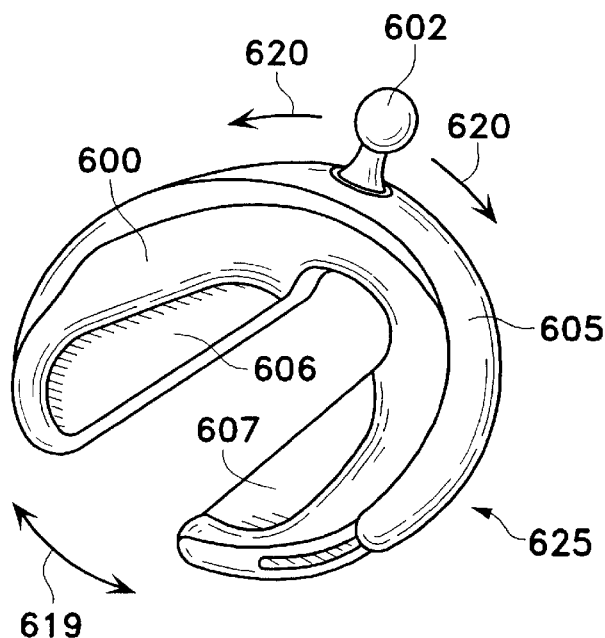
Figure 50:
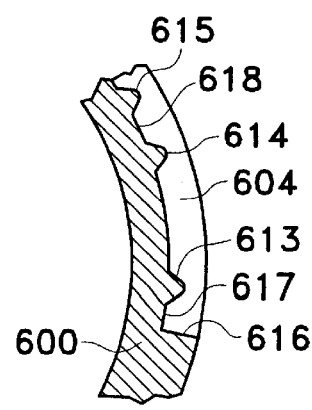
FIG. 50 is a partial cross-sectional view through a portion of the rear guide slot of the stabilizer base of FIG. 47.

Stabilizer base 590 in FIG. 46 has ball/post 592 mounted to an articulating member which is moveable between two or more positions. Preferably, ball/post 592 is mounted on first end 594 of pivoting link 591 which is pivotably attached to stabilizer base 590 at pivot pin 596. Preferably, pivot pin 596 is centrally located on pivoting link 591. At second end 593 of pivoting link 591, a locking knob 595 may be provided to engage stabilizer base 590. Preferably, locking knob 595 has a threaded shaft or other such fastening or locking feature which engages mating threaded holes (typically one positioned under locking knob 595 and one under ball/post 592) in stabilizer base 590. The ball/post 592 and locking knob 595 are preferably spaced equal distances from pivot pin 596 such that when pivoting link 591 is rotated as indicated by arrow 597, the position of ball/post 592 and locking knob 595 are reversed.

Another embodiment of a tissue stabilizer having an adjustable attachment position of the connecting shaft is illustrated in FIGS. 47–50. Stabilizer base assembly 625 includes top member 605 and stabilizer base 600, having contact members 606 and 607 and notch or relief 603 under which a vessel may safely pass without being occluded. At least a portion of stabilizer base 600 has outer profile 601 which is generally curved or circular at a predetermined radius. Top member 605 has a mating interior curvature such that stabilizer base 600 and top member 605 concentrically rotate relative to each other, preferably about a common center point. Ball/post 602 may be attached at a convenient position, typically centered, on top member 605. Rotation of top member 605 relative to stabilizer base 600, as indicated by arrows 620 and 619, thus adjusts the position of ball/post 602 along an arcuate path relative to contact members 606 and 607.

To facilitate the secure attachment and smooth rotation of top member 605 relative to stabilizer base 600, top member 605 may be provided with one or more projections adapted to be received within guide slots provided in stabilizer base 600. In a preferred embodiment, top member 605 has side projections or rails 608 and 609 which snap into lower slots or channels 611 and 610 in stabilizer base 600 as top member 605 is urged into a concentric position over stabilizer base 600. Rails 608 and 609 slide within channel 611 and 610 to maintain a secure attachment and controlled rotation of top member 605 and stabilizer base 600. Top member 605 may optionally have tab 612 adapted to be received within upper slot 604 on stabilizer base 600. Upper slot 604 may have a plurality of detents or teeth which form a desired number of detented positions as tab 612 is rotated around the path of upper slot 604. In a preferred embodiment, detented position 617 is formed between tooth 613 and slot end 616 and detented position 618 is formed between tooth 614 and tooth 615. Of course, detented positions may be created at any desired location using a variety of alternate constructions. Preferably, the detent action of tab 612 allows the operator to manually select a position of ball/post 602, but then holds the position of top member 605 relative to stabilizer base 600 against movement during use to ensure effective stabilization of a target vessel on the beating heart.

In addition to the critical function of stabilizing the beating heart, it is also important for the tissue stabilizer to present the stabilized coronary artery in a manner which allows sutures to be easily placed around the mouth of the arteriotomy as required to create the anastomosis. FIGS. 51A–54 illustrate a tissue stabilizer embodiment involving a base portion having a single contacting surface for stabilizing a target vessel on the beating heart and a mechanical bail element to facilitate optimal vessel presentation.

Figure 51A:
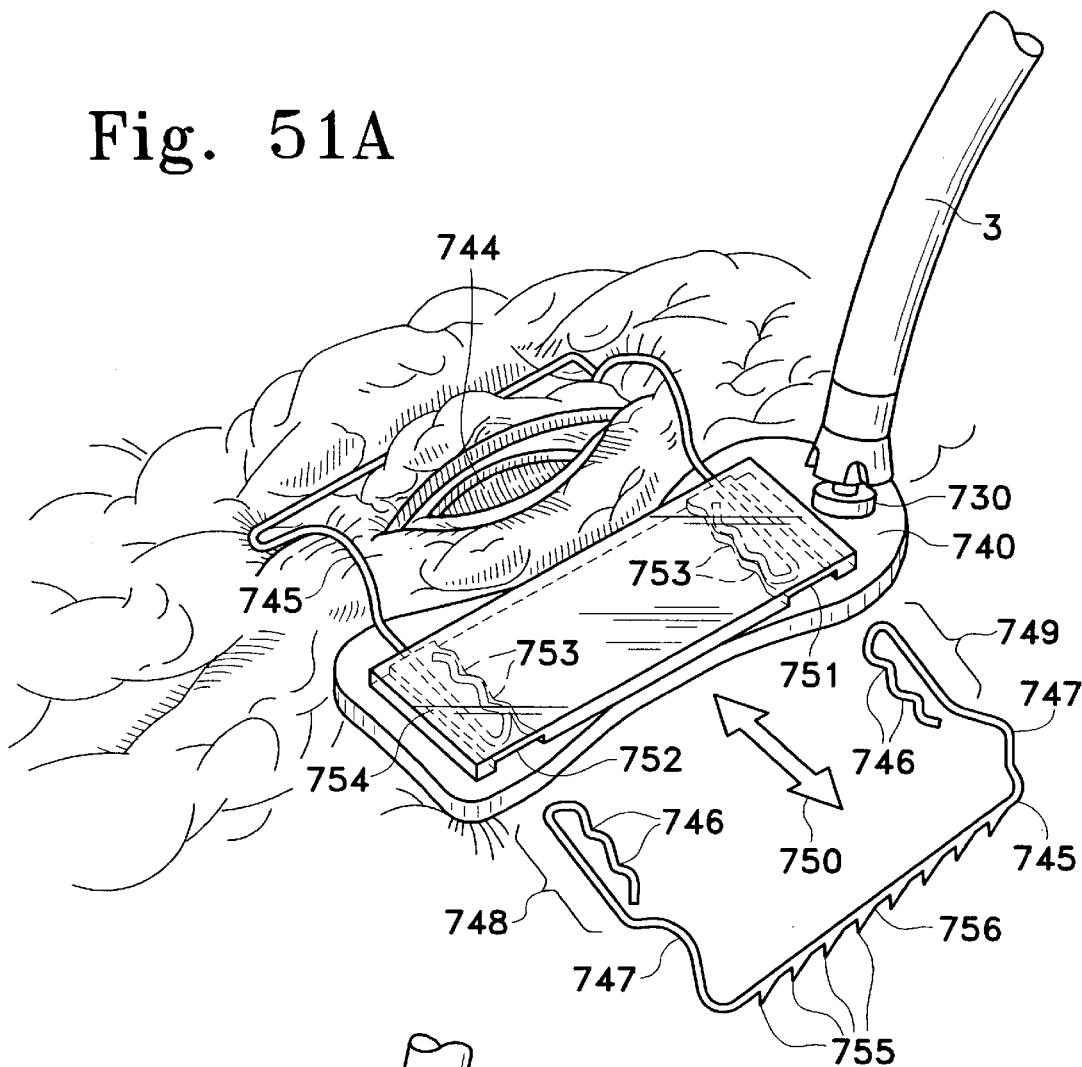
FIG. 51A is a perspective view of a stabilizer base embodiment having a single contact member and bail construction.
Figure 51B:
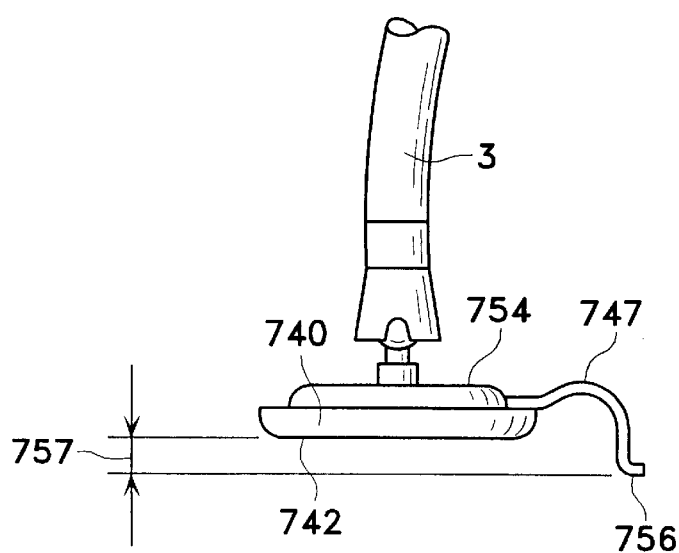
FIG. 51B is an end plan view of the stabilizer embodiment of FIG. 51A.

Referring to FIGS. 51A and 51B stabilizer base 740 is shown attached to connecting shaft 3 using ball/post 730. Connecting shaft 3 is shown connected generally to the center of stabilizer base 740 at approximately a right angle, however, as discussed above, the ball/post 730 could be connected at any desired offset or orientation or the position of ball/post 730 could be adjustable. Stabilizer base 740 preferably has a single contacting surface 742 which may be flat or curved to at least partially conform to the surface of the heart. Contacting surface 742 is sized to provide sufficient contacting area such that sufficient compressive force can be applied to the beating heart to achieve effective immobilization or stabilization of a target coronary artery.

Stablizer base 740 preferably has an extending frame member or bail 745 attached thereto. Bail 745 may be a thin, round or square cross-sectioned member, and is preferably a stainless steel wire. Bail 740 has a bail portion 756 which is generally parallel to stabilizer base 740 and may have relieved sections 747 formed therein so as not to occlude the vessel during use. Bail portion 756 may have tissue gripping features, such as teeth 755. In an optional embodiment, bail portion 756 may be provided with rotating cover or a spiral wound thread (not shown) so that bail portion may be more easily repositioned, under a stabilizing load, over the surface of the heart as discussed below.

In a preferred embodiment, bail 745 is moveable relative to stabilizer base 740. Bail 745 can be moved in or out in the direction indicated by arrow 750 to cause bail section 756, which is generally parallel with stabilizer base 740, to compress tissue towards stabilizer base 740 or stretch tissue away from stabilizer base 740. Thus, bail 745 can be moved in and out to compress or stretch the tissue surrounding a coronary artery until the optimum presentation for performing the anastomosis is achieved. The generally parallel portion may be vertically offset from contacting surface 742 by a distance 757 which is typically about 0.050 inches to about 0.200 inches.

Although bail 745 may be attached in a number of ways, bail 745 is preferably formed with first and second end portions 748 and 749 having detents or teeth 746. Stabilizer base 740 preferably has channels 751 and 752 for receiving end portions 749 and 748 respectively. Channels 751 and 752 preferably have internal mating teeth 753 for engaging teeth 746. End portions 748 and 749 can be incrementally advanced into channels 752 and 751 as teeth 746 deflect and release from a mated position relative to teeth 753 and then successively engage the next mated position. Stabilizer base 740 may include cover 754 over channels 751 and 752. So that the stabilizer can be removed from around a completed anastomosis, at least one end of bail 745 is detachable from stabilizer base 740. In a preferred embodiment, stabilizer base 740 is substantially symmetrical allowing bail 745 to be assembled from either side in a right or left handed configuration.

Bail 745 is preferably flexible or semi-flexible relative to stabilizer base 740. As a result of its inherent flexibility, bail 745 applies a predetermined force against the heart that, under operating conditions, may be generally independent of the stabilizing force applied to stabilizer base 740 to stabilize the beating heart. That is, once stabilizer base 740 is forced against the surface of the heart, the force applied by bail 745 is a function of its mechanical spring rate relative to stabilizer base 740.

Figures 52A, 52B:
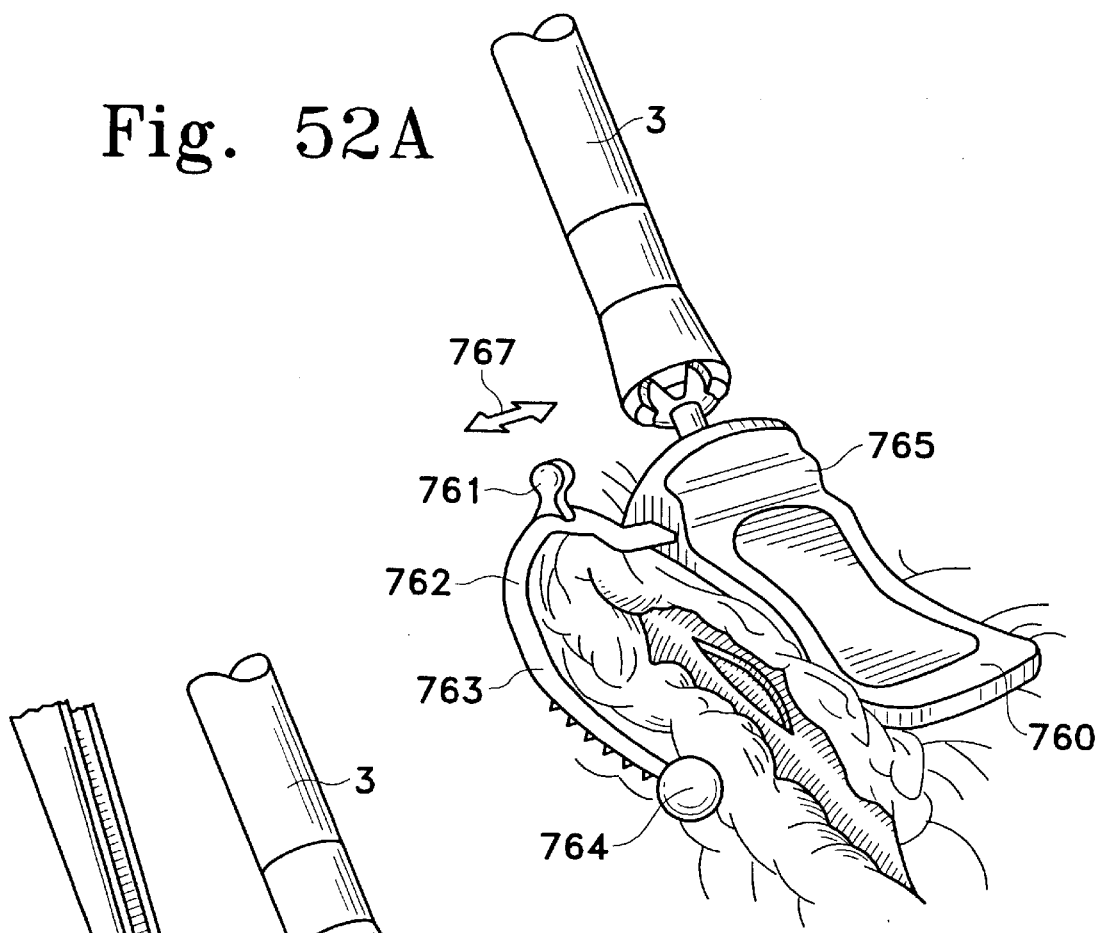
FIG. 52A and 52B are perspective views illustrating another stabilizer base embodiment having a single contact member and bail construction.

FIGS. 52A and 52B illustrate another single contact stabilizer base having a bail 762 which is secured at only one end. Stabilizer base 760 may have a housing 765 having a series of internal teeth (not shown). Bail 762 has a toothed end 766 which is received within housing 765 to engage with the mating teeth provided therein. As with the embodiment above, bail 762 has a generally parallel portion 763 which is moveable relative to stabilizer base 760 in the direction generally indicated by arrow 767 to stretch or compress the surrounding tissue for optimum vessel presentation. Bail 762 may have tab 761 to facilitate grasping by an instrument, such as for example forceps 761. The free end 764 of bail 762 is preferably rounded or somewhat bulbous so as to be atraumatic. Because bail 762 attaches only at one end, the stabilizer can be easily removed from the completed anastomosis without removing bail 762 from stabilizer base 760.

Figure 53:
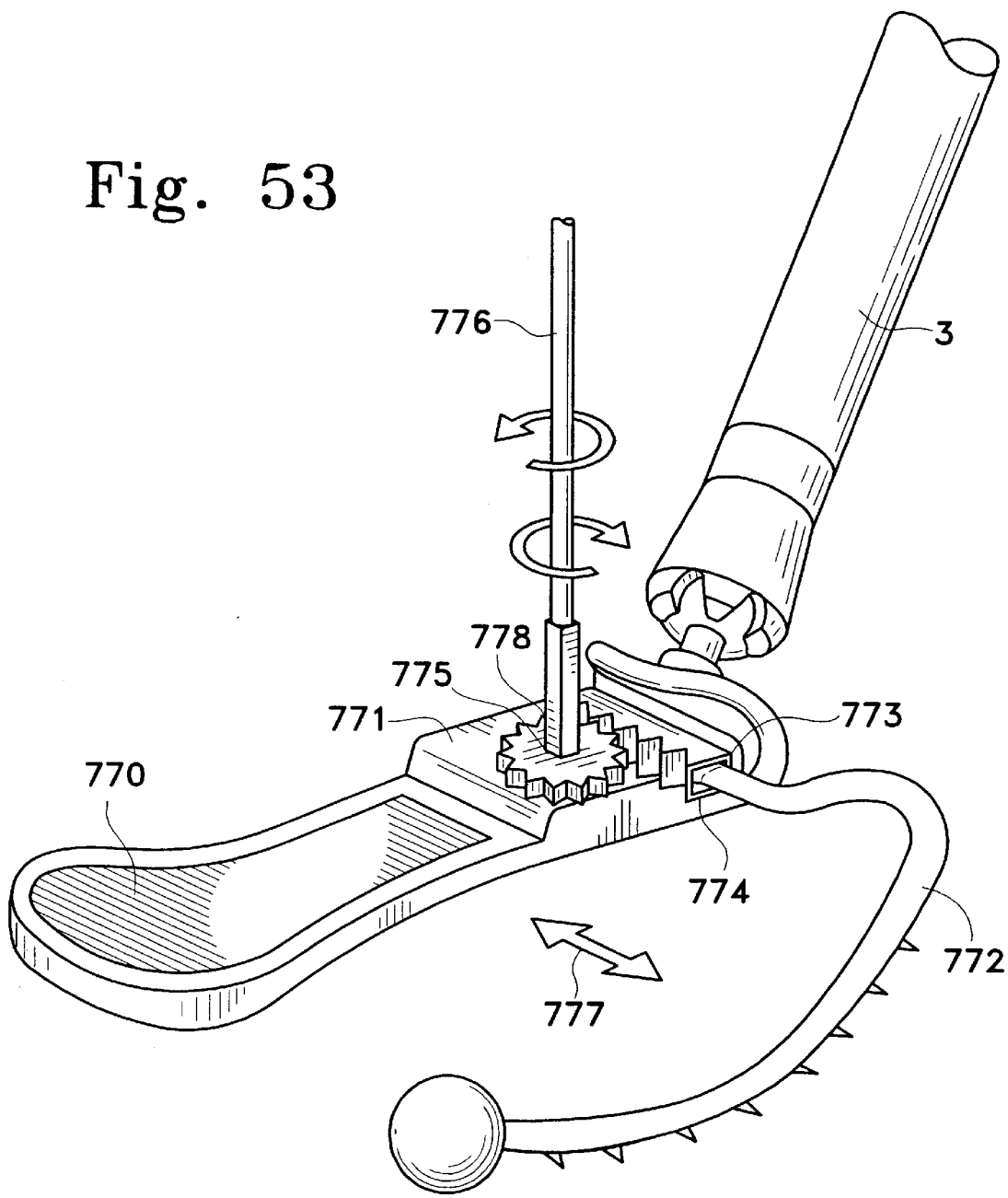
FIGS. 53 and 54 are perspective views illustrating stabilizer base embodiments having a single contact member and a bail having a mechanical drive.

In another embodiment of the stabilizer, the wire frame member or bail may have a drive mechanism for moving the bail relative to the stabilizer base. Referring to FIG. 53 stabilizer base 770 has housing 771 which is constructed with guide channel 774 having gear 775 mounted for rotation therein. Bail 772 has a toothed end 773 which may be assembled within guide channel 774 such that rotation of gear 775 causes bail 772 to be moved in and out in the direction indicated by arrow 43. Gear 775 may be driven by any suitable tool, for example, gear 775 may have a drive hole 778 for engagement by a suitable drive tool 771.

Figure 54:
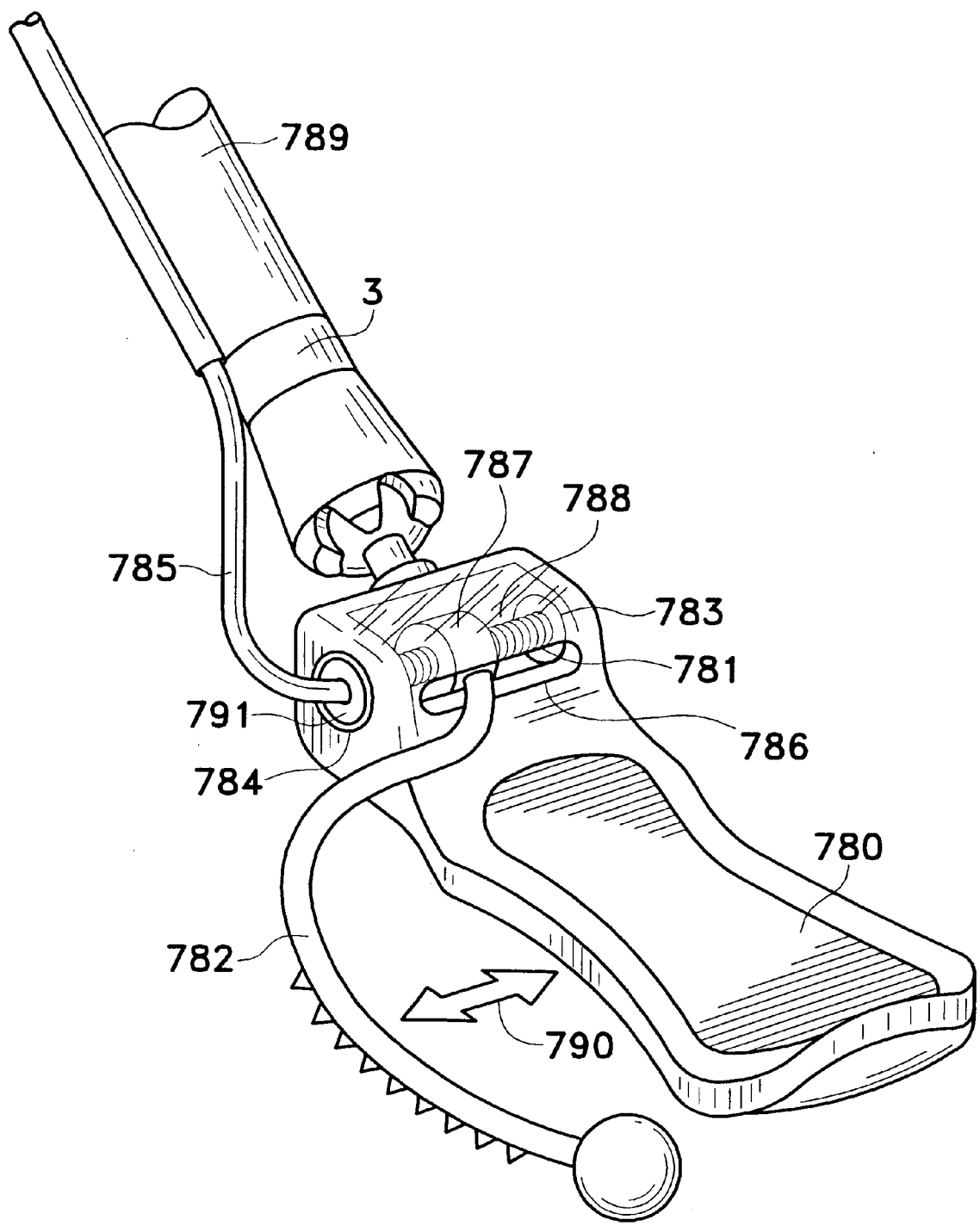

Another driven bail stabilizer is shown in FIG. 54. In this embodiment, stabilizer base 780 has threaded shaft 781 preferably supported at its end portions by bushings or bearings 783 and 784. One end of the threaded shaft is connected to a flexible drive 785 through a flexible or universal joint 791. The flexible drive may be routed up connecting shaft 3. Preferably flexible drive 785 is secured to connecting shaft 3 by way of a thin polymeric coating. Bail 782 is connected to threaded collar 787 which cooperates with threaded shaft 781 to move bail in and out relative to stabilizer base 780 in the general direction indicated by arrow 790. The screw and collar drive mechanism is preferably concealed by housing 788 which has only a small slotted opening 786 allowing passage of bail 782.

With each of the flexible bail embodiments described above, stabilization and vessel presentation are relatively independent. First, the beating heart is typically stabilized using a compressive force delivered by way of the single contacting surface provided by the stabilizer base. The bail may then be manipulated in or out to obtain the optimum presentation of the vessel for whatever surgical procedure is underway. For example, one bail position may be optimal for creating the arteriotomy, another bail position for insertion of a shunt or like device (should one be used), another bail position for creating the anastomosis, and so on. All the while, the stabilization of the beating heart itself remains optimized by the contacting surface of the stabilizer base.

The Stabilization System

Figure 55:
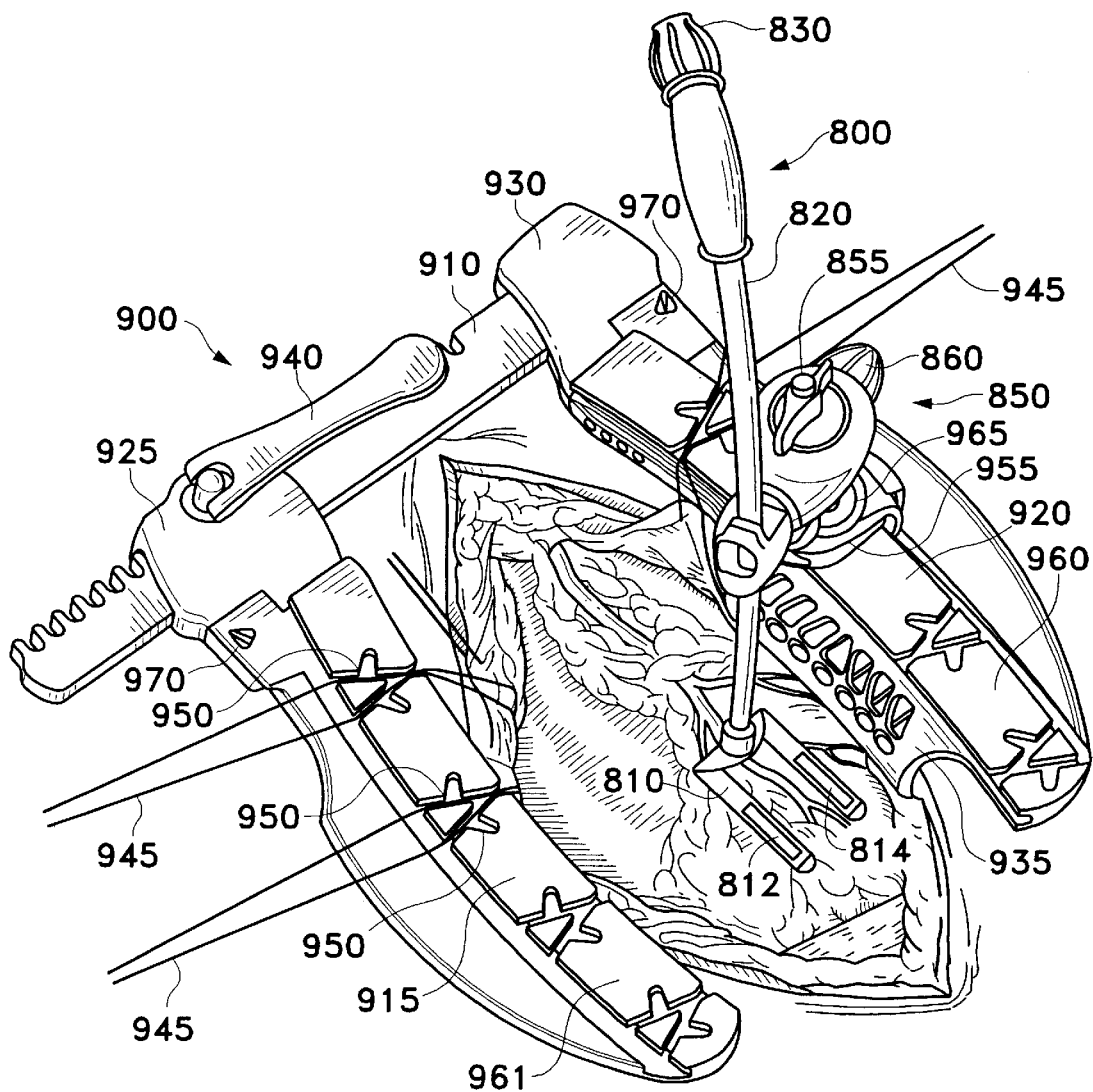
FIG. 55 is a perspective view of a preferred cardiac surgery system during operation according to the principles of the present invention.

Preferred embodiments for each of the retractor, the instrument mount and the tissue stabilizers have been discussed in detail above. While each component may be utilized separately, superior access and stabilization can be achieved when the multiple components are used together for performing a minimally invasive cardiac surgery, preferably through a sternotomy approach. Referring to FIG. 55, retractor assembly 900, including drive mechanism 910 and first and second platform blades 915 and 920, may be used to spread the sternum, providing access and direct visualization to the thoracic cavity. Retractor assembly 900 also allows sutures to be fixed or organized. Stabilizer assembly 800 isolates and provides local immobilization of the target vessel on the beating heart. Instrument mount assembly 850 facilitates precise maneuvering of the stabilizer and ensures a stable, motion free mount at the desired position and orientation.

To begin a typical beating heart CABG procedure using the preferred stabilization system illustrated in FIG. 55, drive mechanism 910 is preferably placed in the fully closed position with moveable housing 925 positioned against or adjacent fixed housing 930. First platform blade 915 is then assembled to moveable housing 925 and a second platform blade 920 is assembled to fixed housing 930. After ensuring that platform blades 915 and 920 are fully and securely attached to drive mechanism 910, engaging members 935 of platform blades 915 and 920 are securely seated on the incised sternum created using standard surgical procedures. Drive handle 940 may then be rotated clockwise to separate platform blades 915 and 920, thus creating the desired opening for accessing the beating heart.

If positioning the heart using sutures to position the heart, the sutures may be placed through the tissue at the desired location and secured to platform blades 915 and 920. Sutures 945 may be slid into suture holder slots 950 to engage the suture. To ensure proper a proper hold, only one suture strand is preferably engaged within each suture holder slot 950. Sutures 945 are released from platform blades 915 and 920 by concurrently pulling back and up on suture 945 while pulling the suture through the suture holder slot 950.

With the heart positioned as desired, instrument mount assembly 850 may be assembled to platform blade 920 (or 915) by hooking stabilizer mount base 955 onto rail 960 (or 961) at the desired location and moving the base lever (not visible in this view) clockwise to the closed position to secure instrument mount assembly 850 onto rail 960. Mount body 110 may be oriented to the desired angle by way of ball joint 965 and locked into place by turning the top mount knob 855 clockwise.

Stabilizer base 810, having contact members 812 and 814, may then be positioned on the epicardium of the beating heart by gently lowering connecting shaft 820 using one hand to guide stabilizer base 810 onto the target area on the heart. Incremental pressure is applied to stabilizer base 810 situated on the epicardium until the desired immobilization or stabilization is achieved. Connecting shaft 820 is secured in the desired position by turning side mount knob 860 clockwise and stabilizer base 810 is secured in the desired position relative to connecting shaft 820 by turning the stabilizer shaft knob 830 clockwise. With the beating heart stabilized the anastomosis, or other desired procedure, is completed.

To remove stabilizer base 810, connecting shaft 820 is held with one hand while side mount knob 860 is loosened with the other hand. Stabilizer base 810 is then carefully removed from the anastomotic site. The base lever is moved to the open position to release instrument mount assembly 850, and stabilizer assembly 800 mounted thereto, from rail 960 on platform blade 920. When the entire bypass procedure is completed, drive handle 940 is rotated in the counter clockwise direction to close drive mechanism 910 and platform blades 915 and 920. Retractor assembly 900 may then be gently removed from the access incision. To remove platform blades 915 and 920 from moveable housing 925 and fixed housing 930, respectively, release latches 970 are manually activated and platform blades 915 and 920 may be pulled generally straight away from drive mechanism 910. Drive mechanism 910 may then be sterilized and prepared for use in a subsequent procedure.

While certain embodiments are illustrated in the drawings and have just been described herein, it will be apparent to those skilled in the art that many modifications can be made to the embodiments without departing from the inventive concepts described. For purposes of illustration only, the principles of the present invention has been generally described with reference to a coronary artery bypass procedure, but may readily be applied to other types surgical procedures not specifically described. Many other uses are well-known in the art, and the concepts described herein are equally applicable to those other uses. Further, the different components of the various exemplar embodiments described above can be combined in any desirable construction. Accordingly, the invention is not to be restricted except by the claims which follow.

What is claimed is:

1. An apparatus for stabilizing a localized portion of a beating heart, comprising:
a substantially rigid base member having at least one contact area adapted to frictionally engage the surface of the beating heart adjacent a first side of a target vessel; and
a wire frame coupled to said base member, said wire frame having a frame portion adapted to engage the beating heart adjacent a second side of said target vessel opposite to said first side and at least one leg portion, said leg portion connecting said frame portion to said base member.

2. The apparatus of claim 1 further comprising a shaft having a proximal end and a distal end, said base member being operably connected to said distal end.

3. The apparatus of claim 2 wherein said shaft is substantially rigid.

4. The apparatus of claim 3 wherein said shaft is curved.

5. The apparatus of claim 1 wherein said leg portion is substantially perpendicular to said frame portion.

6. The apparatus of claim 1 wherein said wire frame is moveable relative to said base member.

7. The apparatus of claim 6 wherein said base member further comprises a channel for slidably receiving at least a portion of said leg portion.

8. The apparatus of claim 7 wherein said leg portion has a plurality of detented positions within said channel.

9. The apparatus of claim 8 wherein said channel further comprises a plurality of teeth and said leg portion further comprises a plurality of mating teeth adapted to engage said teeth.

10. The apparatus of claim 1 wherein said leg portion is substantially flexible relative to said base member.

11. The apparatus of claim 10 wherein said wire frame is formed from a unitary length of wire material.

12. The apparatus of claim 11 wherein the wire material is selected from the group consisting of stainless steel and titanium.

13. The apparatus of claim 1 wherein said frame portion has a first end and a second end and said wire frame comprises a first leg portion attached to said first end and a second leg portion attached to said second end, said first and second leg portions being coupled to said base member.

14. The apparatus of claim 13 wherein said base portion further comprises a first channel and a second channel for slidably receiving said first leg portion and said second leg portion respectively.

15. The apparatus of claim 6 wherein said base member further comprises a pinion gear having a plurality of gear teeth and said leg portion further comprising a rack having a plurality of mating teeth adapted to engage said gear teeth.

16. The apparatus of claim 6 wherein said base member further comprises a threaded shaft rotatably coupled to said base member, and said leg portion further comprises a collar having a threaded interior adapted to receive said threaded shaft.

17. The apparatus of claim 1 wherein said frame portion is vertically offset from said at least one contact area.

18. The apparatus of claim 17 wherein said vertical offset is between about 0.05 inches to about 0.2 inches.

19. The apparatus of claim 17 wherein said at least one contact area is substantially planar.

20. The apparatus of claim 1 wherein said at least one leg portion further comprises a vertically relieved portion.

* * * * *

UNITED STATES PATENT AND TRADEMARK OFFICE
CERTIFICATE OF CORRECTION

PATENT NO.    : 6,290,644 B1
DATED         : September 18, 2001
INVENTOR(S)   : Green II et al.

It is certified that error appears in the above-identified patent and that said Letters Patent is hereby corrected as shown below:

Column 1,
Line 14, "5,894,743" with -- 5,894,843 --.

Signed and Sealed this

Seventeenth Day of December, 2002

JAMES E. ROGAN
*Director of the United States Patent and Trademark Office*